(12) United States Patent
Perrow et al.

(10) Patent No.: US 8,623,019 B2
(45) Date of Patent: Jan. 7, 2014

(54) BONE PLATE SYSTEM

(75) Inventors: Scott J. Perrow, Ishpeming, MI (US); Brad Fredin, Negaunee, MI (US); Craig Filizetti, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 684 days.

(21) Appl. No.: 12/167,666

(22) Filed: Jul. 3, 2008

(65) Prior Publication Data

US 2009/0012571 A1 Jan. 8, 2009

Related U.S. Application Data

(60) Provisional application No. 60/947,873, filed on Jul. 3, 2007, provisional application No. 61/024,287, filed on Jan. 29, 2008.

(51) Int. Cl.
- *A61B 17/56* (2006.01)
- *A61B 17/58* (2006.01)
- *A61B 17/80* (2006.01)
- *A61F 2/30* (2006.01)

(52) U.S. Cl.
USPC ............... 606/70; 606/280; 606/71; 606/286; 606/289; 606/279

(58) Field of Classification Search
USPC ............... 606/69, 70, 71, 73, 280–299, 72
See application file for complete search history.

(56) References Cited

U.S. PATENT DOCUMENTS

| | | |
|---|---|---|
| 434,503 A | 8/1890 | Corry |
| 556,642 A | 3/1896 | Reessing |
| 872,897 A | 12/1907 | Chapman et al. |
| 951,800 A | 3/1910 | Center |
| 1,084,680 A | 1/1914 | Wegener |

(Continued)

FOREIGN PATENT DOCUMENTS

| | | |
|---|---|---|
| DE | 251246 | 12/1911 |
| DE | 1949923 | 4/1971 |

(Continued)

OTHER PUBLICATIONS

International Search Report dated Nov. 18, 2008, from the International Searching Authority in corresponding International (PCT) Application No. PCT/US2008/069221.

(Continued)

*Primary Examiner* — Sameh Boles
*Assistant Examiner* — Samuel Hanna
(74) *Attorney, Agent, or Firm* — Fitch, Even, Tabin & Flannery LLP

(57) ABSTRACT

Bone plate systems are provided for surgical implants and bone repair. The bone plate is multi-tiered for receiving bone anchors screws for securing a plurality of bones or bone fragments in a desired relationship. The plate members include throughbores for receiving a pivot base therein, with head ends of the bone anchors being secured in the pivot bases. The throughbores may permit and define a translation path for the pivot base and the bone anchor secured therein relative to the plate. Pivot members extending between the pivot base and the plate member facilitate pivoting and optional translation of the pivot base relative to the plate. With the bone anchor seated within the pivot base, an apparatus for inhibiting screw back out is employed.

43 Claims, 65 Drawing Sheets

(56) References Cited

U.S. PATENT DOCUMENTS

| | | |
|---|---|---|
| 1,087,797 A | 2/1914 | Lowe |
| 1,385,780 A | 7/1921 | Dodds |
| 1,409,157 A | 3/1922 | Dodds |
| 1,756,239 A | 4/1930 | Chojnacki et al. |
| 1,907,506 A | 5/1933 | Coburn |
| 1,980,336 A | 11/1934 | Hoagland |
| 2,248,054 A | 7/1941 | Becker |
| 2,376,768 A | 5/1945 | Glumer |
| 2,401,856 A | 6/1946 | Brock |
| 2,580,821 A | 1/1952 | Nicola |
| 2,628,838 A | 2/1953 | Smalley |
| 2,780,223 A | 2/1957 | Haggland |
| 2,877,792 A | 3/1959 | Tybus |
| 3,100,516 A | 8/1963 | Naab |
| 3,244,170 A | 4/1966 | McElvenny |
| 3,426,364 A | 2/1969 | Lumb |
| 3,534,731 A | 10/1970 | Mueller |
| 3,596,656 A | 8/1971 | Kaute |
| 3,599,977 A | 8/1971 | Glass et al. |
| 3,659,595 A | 5/1972 | Haboush |
| 3,695,259 A | 10/1972 | Yost |
| 3,741,205 A | 6/1973 | Markolf et al. |
| 3,842,825 A | 10/1974 | Wagner |
| RE28,841 E | 6/1976 | Allgower et al. |
| 4,003,376 A | 1/1977 | McKay et al. |
| 4,029,091 A | 6/1977 | von Bezold et al. |
| 4,334,599 A | 6/1982 | Ritsema et al. |
| RE31,040 E | 9/1982 | Possis |
| 4,361,141 A | 11/1982 | Tanner |
| 4,388,921 A | 6/1983 | Sutter et al. |
| RE31,628 E | 7/1984 | Allgower et al. |
| 4,473,068 A | 9/1984 | Oh |
| 4,484,570 A | 11/1984 | Sutter et al. |
| 4,488,543 A | 12/1984 | Tornier |
| 4,493,317 A | 1/1985 | Klaue |
| 4,503,848 A | 3/1985 | Caspar et al. |
| 4,599,086 A | 7/1986 | Doty |
| 4,762,122 A | 8/1988 | Slocum |
| 4,771,767 A | 9/1988 | Steffee |
| 4,776,330 A | 10/1988 | Chapman et al. |
| 4,794,918 A | 1/1989 | Wolter |
| 4,890,845 A | 1/1990 | Gatewood |
| 4,892,545 A | 1/1990 | Day et al. |
| 4,904,261 A | 2/1990 | Dove et al. |
| 4,905,679 A | 3/1990 | Morgan |
| 4,943,292 A | 7/1990 | Foux |
| 4,955,908 A | 9/1990 | Frey et al. |
| 4,957,497 A | 9/1990 | Hoogland et al. |
| 4,964,403 A | 10/1990 | Karas et al. |
| 5,002,544 A | 3/1991 | Klaue et al. |
| 5,041,113 A | 8/1991 | Biedermann et al. |
| 5,041,114 A | 8/1991 | Chapman et al. |
| 5,053,036 A | 10/1991 | Perren et al. |
| 5,057,111 A | 10/1991 | Park |
| 5,085,660 A | 2/1992 | Lin |
| 5,092,320 A | 3/1992 | Maurer |
| 5,108,395 A | 4/1992 | Laurain |
| 5,113,685 A | 5/1992 | Asher et al. |
| 5,127,912 A | 7/1992 | Ray et al. |
| 5,127,914 A | 7/1992 | Calderale et al. |
| 5,129,899 A | 7/1992 | Small et al. |
| 5,129,903 A | 7/1992 | Luhr et al. |
| 5,139,498 A | 8/1992 | Astudillo Ley |
| 5,147,360 A | 9/1992 | Dubousset |
| 5,147,361 A | 9/1992 | Ojima et al. |
| 5,151,103 A | 9/1992 | Tepic et al. |
| 5,180,381 A | 1/1993 | Aust et al. |
| 5,190,544 A | 3/1993 | Chapman et al. |
| 5,234,431 A | 8/1993 | Keller |
| 5,261,910 A | 11/1993 | Warden et al. |
| 5,269,784 A | 12/1993 | Mast |
| 5,275,601 A | 1/1994 | Gogolewski et al. |
| 5,304,179 A | 4/1994 | Wagner |
| 5,324,290 A | 6/1994 | Zdeblick et al. |
| 5,326,206 A | 7/1994 | Moore |
| 5,330,535 A | 7/1994 | Moser et al. |
| 5,344,421 A | 9/1994 | Crook |
| 5,346,492 A | 9/1994 | Morgan |
| 5,364,399 A | 11/1994 | Lowery et al. |
| 5,380,323 A | 1/1995 | Howland |
| 5,380,327 A | 1/1995 | Eggers et al. |
| 5,382,248 A | 1/1995 | Jacobson et al. |
| 5,397,363 A | 3/1995 | Gelbard |
| 5,397,364 A | 3/1995 | Kozak et al. |
| 5,415,661 A | 5/1995 | Holmes |
| 5,423,826 A | 6/1995 | Coates et al. |
| 5,454,769 A | 10/1995 | Chen |
| 5,458,641 A | 10/1995 | Ramirez Jimenez |
| 5,468,242 A | 11/1995 | Reisberg |
| 5,478,342 A | 12/1995 | Kohrs |
| 5,486,176 A | 1/1996 | Hildebrand et al. |
| 5,501,684 A | 3/1996 | Schlapfer et al. |
| 5,520,690 A | 5/1996 | Errico et al. |
| 5,520,696 A | 5/1996 | Wenstrom, Jr. |
| 5,522,899 A | 6/1996 | Michelson |
| 5,527,311 A | 6/1996 | Procter et al. |
| 5,531,746 A | 7/1996 | Errico et al. |
| 5,534,027 A | 7/1996 | Hodorek |
| 5,534,032 A | 7/1996 | Hodorek |
| 5,549,612 A | 8/1996 | Yapp et al. |
| 5,569,247 A | 10/1996 | Morrison |
| 5,571,109 A | 11/1996 | Bertagnoli |
| 5,578,034 A | 11/1996 | Estes |
| 5,601,553 A | 2/1997 | Trebing |
| 5,603,713 A | 2/1997 | Aust et al. |
| 5,607,426 A | 3/1997 | Ralph et al. |
| 5,607,428 A | 3/1997 | Lin |
| 5,616,144 A | 4/1997 | Yapp et al. |
| 5,620,443 A | 4/1997 | Gertzbein et al. |
| 5,626,449 A | 5/1997 | McKinlay |
| 5,643,265 A | 7/1997 | Errico et al. |
| 5,647,872 A | 7/1997 | Gilbert et al. |
| 5,651,651 A | 7/1997 | Spencer |
| 5,653,708 A | 8/1997 | Howland |
| 5,667,513 A | 9/1997 | Torrie et al. |
| 5,676,666 A | 10/1997 | Oxland et al. |
| 5,676,703 A | 10/1997 | Gelbard |
| 5,681,311 A | 10/1997 | Foley et al. |
| 5,681,312 A | 10/1997 | Yuan et al. |
| 5,683,465 A | 11/1997 | Shinn et al. |
| 5,690,631 A | 11/1997 | Duncan et al. |
| 5,704,936 A | 1/1998 | Mazel |
| 5,707,372 A | 1/1998 | Errico et al. |
| 5,709,686 A | 1/1998 | Talos et al. |
| 5,713,900 A | 2/1998 | Benzel et al. |
| 5,725,588 A | 3/1998 | Errico et al. |
| 5,731,275 A | 3/1998 | Prevost et al. |
| 5,735,850 A | 4/1998 | Baumgartner et al. |
| 5,735,853 A * | 4/1998 | Olerud ............ 606/71 |
| 5,735,899 A | 4/1998 | Schwartz et al. |
| 5,741,258 A | 4/1998 | Klaue et al. |
| 5,766,176 A | 6/1998 | Duncan |
| 5,766,254 A | 6/1998 | Gelbard |
| 5,797,912 A * | 8/1998 | Runciman et al. ........... 606/286 |
| 5,800,433 A | 9/1998 | Benzel et al. |
| 5,807,396 A | 9/1998 | Raveh |
| 5,810,823 A | 9/1998 | Klaue et al. |
| 5,814,048 A | 9/1998 | Morgan |
| 5,827,285 A | 10/1998 | Bramlet |
| 5,840,078 A | 11/1998 | Yerys |
| 5,843,082 A | 12/1998 | Yuan et al. |
| 5,876,402 A | 3/1999 | Errico et al. |
| 5,879,389 A | 3/1999 | Koshino |
| 5,888,221 A | 3/1999 | Gelbard |
| 5,904,683 A | 5/1999 | Pohndorf et al. |
| 5,916,200 A | 6/1999 | Eppley et al. |
| 5,951,557 A | 9/1999 | Luter |
| 5,951,558 A | 9/1999 | Fiz |
| 5,954,722 A | 9/1999 | Bono |
| 5,964,762 A | 10/1999 | Biedermann et al. |
| 5,976,141 A | 11/1999 | Haag et al. |
| 5,980,540 A | 11/1999 | Bruce |
| 5,984,924 A | 11/1999 | Asher et al. |
| 6,017,345 A * | 1/2000 | Richelsoph ............ 606/70 |

(56) References Cited

U.S. PATENT DOCUMENTS

| | | |
|---|---|---|
| 6,022,350 A | 2/2000 | Ganem |
| 6,030,389 A | 2/2000 | Wagner et al. |
| 6,036,693 A | 3/2000 | Yuan et al. |
| 6,039,740 A | 3/2000 | Olerud |
| 6,090,111 A | 7/2000 | Nichols |
| 6,106,557 A | 8/2000 | Robioneck et al. |
| 6,117,173 A | 9/2000 | Taddia et al. |
| 6,129,730 A | 10/2000 | Bono et al. |
| 6,132,434 A | 10/2000 | Sherman et al. |
| 6,139,550 A | 10/2000 | Michelson |
| 6,152,927 A | 11/2000 | Farris et al. |
| 6,159,213 A | 12/2000 | Rogozinski |
| 6,183,476 B1 | 2/2001 | Gerhardt et al. |
| 6,189,422 B1 | 2/2001 | Stihl |
| 6,193,720 B1 | 2/2001 | Yuan |
| 6,193,721 B1 | 2/2001 | Michelson |
| 6,206,881 B1 | 3/2001 | Frigg et al. |
| 6,206,882 B1 | 3/2001 | Cohen |
| 6,214,005 B1 | 4/2001 | Benzel et al. |
| 6,224,602 B1 | 5/2001 | Hayes |
| 6,228,085 B1 | 5/2001 | Theken et al. |
| 6,235,032 B1 | 5/2001 | Link |
| 6,235,033 B1 * | 5/2001 | Brace et al. ............... 606/288 |
| 6,235,034 B1 | 5/2001 | Bray |
| 6,241,731 B1 | 6/2001 | Fiz |
| 6,254,603 B1 | 7/2001 | Gertzbein et al. |
| 6,257,593 B1 | 7/2001 | White |
| 6,258,089 B1 | 7/2001 | Campbell et al. |
| 6,261,042 B1 | 7/2001 | Pratt |
| 6,261,291 B1 | 7/2001 | Talaber et al. |
| 6,273,889 B1 | 8/2001 | Richelsoph |
| 6,280,445 B1 | 8/2001 | Morrison et al. |
| 6,290,703 B1 | 9/2001 | Ganem |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,315,779 B1 | 11/2001 | Morrison et al. |
| 6,322,562 B1 | 11/2001 | Wolter |
| 6,328,738 B1 | 12/2001 | Suddaby |
| 6,331,179 B1 | 12/2001 | Freid et al. |
| 6,332,887 B1 | 12/2001 | Knox |
| 6,342,055 B1 | 1/2002 | Eisermann et al. |
| 6,342,057 B1 | 1/2002 | Brace et al. |
| 6,361,537 B1 | 3/2002 | Anderson |
| 6,364,880 B1 | 4/2002 | Michelson |
| 6,379,364 B1 | 4/2002 | Brace et al. |
| 6,381,806 B1 | 5/2002 | Stanesic et al. |
| 6,383,186 B1 | 5/2002 | Michelson |
| 6,398,783 B1 | 6/2002 | Michelson |
| 6,402,206 B1 | 6/2002 | Simmons et al. |
| 6,402,755 B1 | 6/2002 | Pisharodi |
| 6,402,756 B1 | 6/2002 | Ralph et al. |
| 6,402,759 B1 | 6/2002 | Strong et al. |
| 6,406,478 B1 | 6/2002 | Kuo |
| 6,413,259 B1 | 7/2002 | Lyons et al. |
| 6,416,528 B1 | 7/2002 | Michelson |
| 6,423,068 B1 | 7/2002 | Reisberg et al. |
| 6,428,542 B1 | 8/2002 | Michelson |
| 6,454,711 B1 | 9/2002 | Michelson |
| 6,454,769 B2 | 9/2002 | Wagner et al. |
| 6,454,771 B1 | 9/2002 | Michelson |
| 6,458,133 B1 | 10/2002 | Lin |
| 6,471,704 B2 | 10/2002 | Gertzbein et al. |
| 6,478,797 B1 | 11/2002 | Paul |
| 6,503,250 B2 | 1/2003 | Paul |
| 6,527,776 B1 | 3/2003 | Michelson |
| 6,533,786 B1 | 3/2003 | Needham et al. |
| 6,572,619 B2 | 6/2003 | Santilli |
| 6,575,975 B2 | 6/2003 | Brace et al. |
| 6,579,290 B1 | 6/2003 | Hardcastle et al. |
| 6,585,769 B1 | 7/2003 | Muhanna et al. |
| 6,592,586 B1 | 7/2003 | Michelson |
| 6,595,993 B2 | 7/2003 | Donno |
| 6,599,290 B2 | 7/2003 | Bailey et al. |
| 6,602,255 B1 | 8/2003 | Campbell et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 * | 9/2003 | Collins et al. ............... 606/293 |
| 6,613,728 B1 | 9/2003 | Sirianni et al. |
| 6,616,666 B1 | 9/2003 | Michelson |
| 6,620,163 B1 | 9/2003 | Michelson |
| 6,623,486 B1 | 9/2003 | Weaver et al. |
| 6,626,907 B2 | 9/2003 | Campbell et al. |
| 6,627,590 B1 | 9/2003 | Sherry et al. |
| 6,652,525 B1 | 11/2003 | Assaker et al. |
| 6,663,632 B1 * | 12/2003 | Frigg ............... 606/246 |
| 6,669,700 B1 | 12/2003 | Farris et al. |
| 6,692,503 B2 | 2/2004 | Foley et al. |
| 6,695,846 B2 | 2/2004 | Richelsoph et al. |
| 6,755,833 B1 | 6/2004 | Paul et al. |
| D501,231 S | 1/2005 | Rom |
| 6,860,883 B2 * | 3/2005 | Janowski et al. ............... 606/56 |
| 6,890,334 B2 | 5/2005 | Brace et al. |
| 6,916,320 B2 | 7/2005 | Michelson |
| 6,964,664 B2 | 11/2005 | Freid et al. |
| 6,966,735 B1 | 11/2005 | Yamazaki |
| 7,048,739 B2 | 5/2006 | Konieczynski et al. |
| 7,074,221 B2 | 7/2006 | Michelson |
| 7,273,481 B2 | 9/2007 | Lombardo et al. |
| 7,410,496 B2 | 8/2008 | Derouet |
| 7,452,370 B2 | 11/2008 | Anderson |
| 7,476,239 B2 | 1/2009 | Jackson |
| 7,618,443 B2 | 11/2009 | Abdou |
| 7,635,366 B2 | 12/2009 | Abdou |
| 7,662,175 B2 | 2/2010 | Jackson |
| 7,666,185 B2 | 2/2010 | Ryan et al. |
| 7,682,379 B2 | 3/2010 | Mathieu et al. |
| 7,766,915 B2 | 8/2010 | Jackson |
| 7,780,706 B2 | 8/2010 | Marino et al. |
| 7,794,482 B2 | 9/2010 | Mathieu et al. |
| 7,854,752 B2 | 12/2010 | Colleran et al. |
| 7,857,836 B2 | 12/2010 | Huebner et al. |
| 7,862,591 B2 | 1/2011 | Dewey et al. |
| 7,875,065 B2 | 1/2011 | Jackson |
| 7,887,569 B2 * | 2/2011 | Frigg ............... 606/280 |
| 7,901,437 B2 | 3/2011 | Jackson |
| 7,909,852 B2 | 3/2011 | Boomer et al. |
| 7,927,359 B2 | 4/2011 | Trautwein et al. |
| 7,935,126 B2 | 5/2011 | Orbay et al. |
| 7,942,909 B2 | 5/2011 | Hammill, Sr. et al. |
| 7,942,910 B2 | 5/2011 | Doubler et al. |
| 7,942,911 B2 | 5/2011 | Doubler et al. |
| 7,947,065 B2 | 5/2011 | Hammill, Sr. et al. |
| 7,951,170 B2 | 5/2011 | Jackson |
| 7,951,173 B2 | 5/2011 | Hammill, Sr. et al. |
| 7,951,179 B2 | 5/2011 | Matityahu |
| 7,967,850 B2 | 6/2011 | Jackson |
| 8,012,177 B2 | 9/2011 | Jackson |
| 8,025,681 B2 | 9/2011 | Colleran et al. |
| 2001/0014807 A1 | 8/2001 | Wagner et al. |
| 2001/0021851 A1 | 9/2001 | Eberlein et al. |
| 2001/0037112 A1 | 11/2001 | Brace et al. |
| 2001/0041894 A1 | 11/2001 | Campbell et al. |
| 2001/0047172 A1 | 11/2001 | Foley et al. |
| 2001/0047174 A1 | 11/2001 | Donno et al. |
| 2002/0013586 A1 | 1/2002 | Justis et al. |
| 2002/0016595 A1 | 2/2002 | Michelson |
| 2002/0022843 A1 | 2/2002 | Michelson |
| 2002/0029040 A1 * | 3/2002 | Morrison et al. ............... 606/61 |
| 2002/0045896 A1 | 4/2002 | Michelson |
| 2002/0045898 A1 | 4/2002 | Freid et al. |
| 2002/0045899 A1 | 4/2002 | Errico et al. |
| 2002/0049444 A1 | 4/2002 | Knox |
| 2002/0058939 A1 | 5/2002 | Wagner et al. |
| 2002/0065517 A1 | 5/2002 | Paul |
| 2002/0068938 A1 | 6/2002 | Jackson |
| 2002/0077630 A1 | 6/2002 | Lin |
| 2002/0111630 A1 | 8/2002 | Ralph et al. |
| 2002/0120268 A1 | 8/2002 | Berger |
| 2002/0120271 A1 | 8/2002 | Dixon et al. |
| 2002/0120272 A1 | 8/2002 | Yuan et al. |
| 2002/0120273 A1 | 8/2002 | Needham et al. |

(56) References Cited

U.S. PATENT DOCUMENTS

| | | |
|---|---|---|
| 2002/0128654 A1 | 9/2002 | Steger et al. |
| 2002/0128655 A1 | 9/2002 | Michelson |
| 2002/0151893 A1 | 10/2002 | Santilli |
| 2002/0151899 A1 | 10/2002 | Bailey et al. |
| 2002/0151900 A1 | 10/2002 | Glascott |
| 2002/0156474 A1 | 10/2002 | Wack et al. |
| 2002/0161370 A1 | 10/2002 | Frigg et al. |
| 2002/0173790 A1 | 11/2002 | Chang et al. |
| 2002/0183747 A1 | 12/2002 | Jao et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023242 A1 | 1/2003 | Harrington, Jr. |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0078583 A1* | 4/2003 | Biedermann et al. ............ 606/69 |
| 2003/0093082 A1 | 5/2003 | Campbell et al. |
| 2003/0105462 A1 | 6/2003 | Haider |
| 2003/0130661 A1 | 7/2003 | Osman |
| 2003/0149434 A1 | 8/2003 | Paul |
| 2003/0153920 A1 | 8/2003 | Ralph et al. |
| 2003/0167058 A1* | 9/2003 | Shluzas ............................ 606/61 |
| 2003/0181912 A1 | 9/2003 | Michelson |
| 2003/0187440 A1 | 10/2003 | Richelsoph et al. |
| 2003/0187441 A1 | 10/2003 | Bolger et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey |
| 2003/0225409 A1 | 12/2003 | Freid et al. |
| 2004/0019353 A1 | 1/2004 | Freid et al. |
| 2004/0030338 A1 | 2/2004 | Paul |
| 2004/0068319 A1* | 4/2004 | Cordaro ...................... 623/17.11 |
| 2004/0087951 A1 | 5/2004 | Khalili |
| 2004/0092938 A1* | 5/2004 | Carli ............................... 606/73 |
| 2004/0097934 A1 | 5/2004 | Farris et al. |
| 2004/0097935 A1 | 5/2004 | Richelsoph et al. |
| 2004/0097950 A1 | 5/2004 | Foley et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0158246 A1 | 8/2004 | Assaker et al. |
| 2004/0186482 A1 | 9/2004 | Kolb et al. |
| 2004/0204710 A1 | 10/2004 | Patel et al. |
| 2004/0204716 A1 | 10/2004 | Fanger et al. |
| 2004/0204717 A1 | 10/2004 | Fanger et al. |
| 2004/0220570 A1* | 11/2004 | Frigg ............................... 606/69 |
| 2004/0220571 A1 | 11/2004 | Assaker et al. |
| 2004/0236334 A1 | 11/2004 | Michelson |
| 2005/0033298 A1* | 2/2005 | Hawkes et al. ................. 606/61 |
| 2005/0038436 A1 | 2/2005 | Michelson |
| 2005/0049593 A1 | 3/2005 | Duong et al. |
| 2005/0192577 A1* | 9/2005 | Mosca et al. .................... 606/69 |
| 2005/0234456 A1 | 10/2005 | Malandain |
| 2006/0079900 A1 | 4/2006 | Mathieu et al. |
| 2006/0106387 A1 | 5/2006 | Fanger et al. |
| 2006/0122602 A1 | 6/2006 | Konieczynski et al. |
| 2006/0122604 A1 | 6/2006 | Gorhan et al. |
| 2006/0149256 A1 | 7/2006 | Wagner et al. |
| 2006/0161157 A1 | 7/2006 | Mosca et al. |
| 2006/0167457 A1* | 7/2006 | Suddaby ......................... 606/69 |
| 2006/0200147 A1 | 9/2006 | Ensign et al. |
| 2006/0217725 A1 | 9/2006 | Suh |
| 2006/0235399 A1 | 10/2006 | Carls et al. |
| 2006/0241616 A1 | 10/2006 | Konieczynski et al. |
| 2007/0010817 A1 | 1/2007 | de Connick |
| 2007/0055251 A1* | 3/2007 | Huebner et al. ................. 606/69 |
| 2007/0123879 A1 | 5/2007 | Songer et al. |
| 2007/0162016 A1* | 7/2007 | Matityahu ....................... 606/69 |
| 2008/0027439 A1* | 1/2008 | Sasing ............................. 606/69 |
| 2008/0177330 A1* | 7/2008 | Ralph et al. .................... 606/290 |
| 2009/0024170 A1 | 1/2009 | Kirschman |
| 2009/0062862 A1* | 3/2009 | Perrow et al. ................. 606/280 |
| 2011/0112584 A1 | 5/2011 | Frigg |

FOREIGN PATENT DOCUMENTS

| | | |
|---|---|---|
| DE | 2933141 | 4/1980 |
| DE | 4409833 | 10/1995 |
| DE | 19548395 | 9/1997 |
| EP | 0 179 695 A1 | 4/1986 |
| EP | 0 201 024 B1 | 11/1986 |
| EP | 0 242 842 B1 | 10/1987 |
| EP | 0 251 583 A2 | 1/1988 |
| EP | 0251583 | 1/1988 |
| EP | 0 410 309 A1 | 1/1991 |
| EP | 0 455 255 A1 | 11/1991 |
| EP | 0 471 418 A1 | 2/1992 |
| EP | 0471418 | 2/1992 |
| EP | 0502815 | 9/1992 |
| EP | 0599640 A1 | 6/1994 |
| EP | 0 699 057 B1 | 3/1996 |
| EP | 0 809 972 A3 | 12/1997 |
| EP | 0 897 697 A1 | 2/1999 |
| EP | 0897697 | 2/1999 |
| EP | 0 903 113 A2 | 3/1999 |
| EP | 0988833 A2 | 3/2000 |
| EP | 0995404 A1 | 4/2000 |
| EP | 0 999 796 B1 | 5/2000 |
| EP | 0 767 631 B1 | 12/2000 |
| EP | 1 106 144 A1 | 6/2001 |
| EP | 1169971 A2 | 1/2002 |
| EP | 1 185 210 | 3/2002 |
| EP | 1 220 645 B1 | 7/2002 |
| EP | 1 306 058 A2 | 7/2002 |
| EP | 1285632 | 2/2003 |
| EP | 0 874 595 B1 | 3/2003 |
| EP | 0 809 971 B1 | 4/2003 |
| EP | 0876128 | 5/2003 |
| EP | 1336383 | 8/2003 |
| EP | 0828459 | 9/2003 |
| EP | 1340468 A2 | 9/2003 |
| EP | 1346697 | 9/2003 |
| EP | 1364623 | 11/2003 |
| EP | 1169971 | 10/2004 |
| FR | 2435243 | 4/1980 |
| FR | 2519857 | 7/1983 |
| FR | 2556583 | 6/1985 |
| FR | 2726461 | 5/1996 |
| FR | 2740321 | 4/1997 |
| FR | 2794963 | 12/2000 |
| FR | 2810532 | 12/2001 |
| SU | 1424824 | 9/1988 |
| WO | 8803781 A1 | 6/1988 |
| WO | WO 88/03781 | 6/1988 |
| WO | WO 91/03994 | 4/1991 |
| WO | 9417744 A1 | 8/1994 |
| WO | WO 95/25474 | 9/1995 |
| WO | WO 95/31941 | 11/1995 |
| WO | WO 96/00530 | 1/1996 |
| WO | 96/05778 | 2/1996 |
| WO | WO 96/08206 | 3/1996 |
| WO | WO 96/29948 | 10/1996 |
| WO | 96/39975 | 12/1996 |
| WO | WO 97/22306 | 6/1997 |
| WO | 98/34553 | 8/1998 |
| WO | 98/34556 | 8/1998 |
| WO | 98/51226 | 11/1998 |
| WO | WO 99/04718 | 2/1999 |
| WO | 99/21502 | 5/1999 |
| WO | 9956653 A1 | 11/1999 |
| WO | WO 99/56653 | 11/1999 |
| WO | WO 99/59492 | 11/1999 |
| WO | 0003653 A2 | 1/2000 |
| WO | WO 00/25689 | 5/2000 |
| WO | 0066011 A1 | 11/2000 |
| WO | WO 00/78238 | 12/2000 |

(56) References Cited

FOREIGN PATENT DOCUMENTS

| WO | 01/01874 | 1/2001 |
|---|---|---|
| WO | 01/26566 | 4/2001 |
| WO | WO 01/26567 | 4/2001 |
| WO | 01/49191 | 7/2001 |
| WO | 0164144 A2 | 9/2001 |
| WO | 01/82804 | 11/2001 |
| WO | 01/82805 | 11/2001 |
| WO | WO 01/82804 | 11/2001 |
| WO | WO 01/82805 | 11/2001 |
| WO | WO 01/89400 | 11/2001 |
| WO | WO 01/89428 | 11/2001 |
| WO | 02/076317 | 10/2002 |
| WO | 02076317 A1 | 10/2002 |
| WO | 02080789 A1 | 10/2002 |
| WO | WO 02/080789 | 10/2002 |
| WO | 02/098277 | 12/2002 |
| WO | 02098276 A2 | 12/2002 |
| WO | 02098277 A2 | 12/2002 |
| WO | WO 02/098276 | 12/2002 |
| WO | WO 02/098277 | 12/2002 |
| WO | 03/007826 | 1/2003 |
| WO | 03007826 A1 | 1/2003 |
| WO | 03017856 A1 | 3/2003 |
| WO | 03/053262 | 7/2003 |
| WO | 03/063714 | 8/2003 |
| WO | WO 03/071966 | 9/2003 |

OTHER PUBLICATIONS

Written Opinion dated Nov. 18, 2008, from the International Searching Authority in corresponding International (PCT) Application No. PCT/US2008/069221.

Moftakhar, Roham, MD; Trost, Gregory, MD. Anterior Cervical Plates: A Historical Perspective. Neurosurgical Focus, vol. 16, No. 1. Jan. 2004. American Association of Neurological Surgeons; Charlottesville, VA, USA. 5 pages.

Omeis et al., "History of Instrumentation for Stabilization of the Subaxial Cervical Spine," Neurosurg Focus 16 (1): Article 10, 2004.

Chang, J.H.; Chang, G.L.; Hsu, A.T.. Kinematic Study of Cervical Vertebrae Adjacent to Fixation Procedures. 1999 Bioengineering Conference, Big Sky, Montana, USA. Jun. 1999. 2 pages.

Tippets, Richard H., MD; Apfelbaum, Ronald I., MD. Anterior Cervical Fusion with the Caspar Instrumentation System. Neurosurgery, vol. 22, No. 6, Part 1. Jun. 1998. 6 pages. Lippincott Williams & Wilkins; Hagerstown, MD, USA.

Benzel, Edward, MD; Leon, Steven, MD. Enhancing Cervical Spine Fusion, www.medscape.com. Mar. 2001. 31 pages.

Paramour, Christoper, MD; Dickman, Curtis, MD; Sonntag, Volker, MD. Radiographic and Clinical Follow-Up Review of Caspar Plates in 49 Patents. Journal of Neurosurgery, vol. 84, No. 6. Jun. 1996. 5 pages. American Association of Neurological Surgeons; Rolling Meadows, IL, USA.

Clausen, John; Tyken, Timothy, MD; Traynelis, Vincent, MD; Sawin, Paul, MD; Dexter, Franklin, MD; Goel, Vijay. Biomechanical Evaluation of Caspar and Cervical Spine Locking Plate Systems in a Cadaveric Model. Journal of Neurosurgery, vol. 84, No. 6. Jun. 1996. 9 pages. American Association of Neurological Surgeons; Rolling Meadows, IL, USA.

Bose, Bikash, MD. Anterior Cervical Fusion Using Caspar Plating: Analysis of Results and Review of the Literature. Surgical Neurology, vol. 29, No. 1. Jan. 1998. 8 pages. Elsevier Biomedical; New York, NY, USA.

Pitzen, T.; Steudel, W.; Oxland, T. The Effect of Posterior Element Injury on Cervical Spine Flexibility While Using Anterior Plates With and Without Posterior Fixation. An In Vitro Trauma Model. $52^{nd}$ Annual Meeting of the German Society of Neurosurgery, Bielefeld, Germany. May 2001. 1 page.

Caspar, W; Barbier, DD; Klara, PM. Anterior Cervical Fusion and Caspar Plate Stabilization for Cervical Trauma. Neurosurgery, vol. 25, No. 4. Oct. 1989. Lippincott Williams & Wilkins; Hagerstown, MD, USA. 1 page.

Armstrong, Gordon; Chow, Donald. The Contoured Anterior Spinal Plate. Spinal Instrumentation. 1992. Williams & Wilkins; Baltimore, MD, USA.

Zdeblick, Thomas, MD; Ghanayem, Alexander, MD; Rapoff, Andrew, MS; Swain, Carol, MS; Bassett, Tim, MD; Cooke, Mary, MS; Markel, Mark, DVM. Cervical Interbody Fusion Cages: An Animal Model With and Without Bone Morphogenetic Protein. Spine, vol. 23, No. 7. Apr. 1998. Lippincott Williams & Wilkins; Hagerstown, MD, USA. 8 pages.

Takahashi, Toshiyuki; Tominaga, Teiji; Yoshimoto, Takashi; Koshu, Keiji; Tokobori, A. Toshimitsu; Aizawa, Yoichi. Biomechanical Evaluation of Hydroxyapatite Intervertebral Graft and Anterior Cervical Plating in a Porcine Cadaveric Model. Bio-medical Materials and Engineering, vol. 7, No. 2. 1997. IOS Press; Amsterdam, Netherlands. 7 pages.

Chen, Ing-Ho; Yang, Rong-Sen; Chen, Po-Quang. Plate Fixation for Anterior Cervical Interbody Fusion. Journal of the Formosan Medical Association, vol. 90, No. 2. Feb. 1991. Scientific Communications International; Hong Kong, China. 4 pages.

Non-Final Office Action dated Feb. 16, 2012 in related U.S. Appl. No. 12/199,321, 15 pages.

* cited by examiner

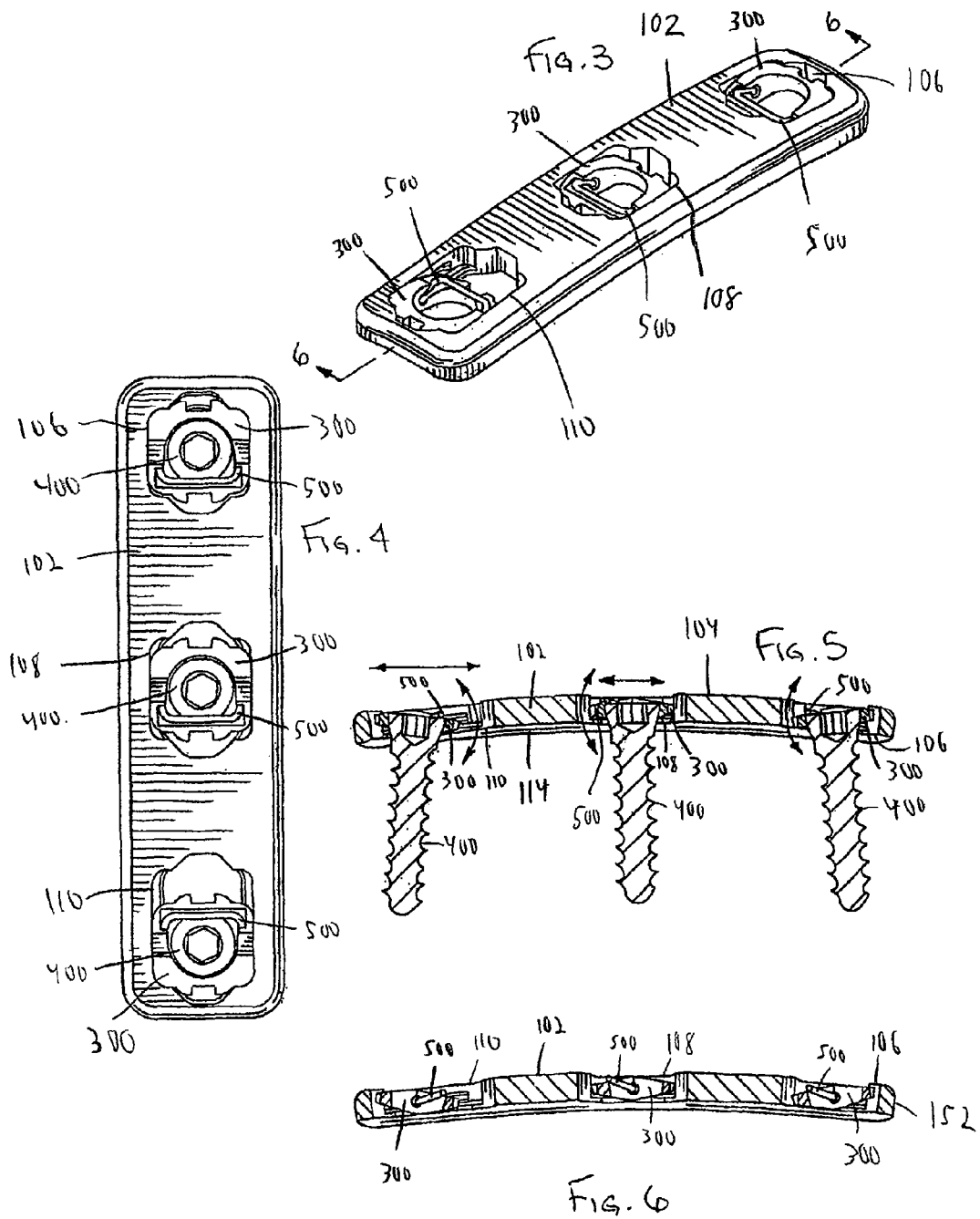

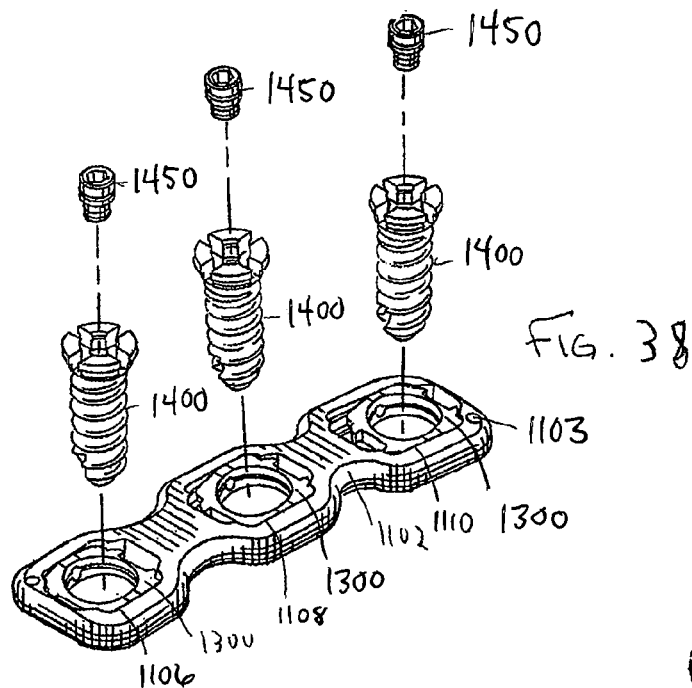
FIG. 38
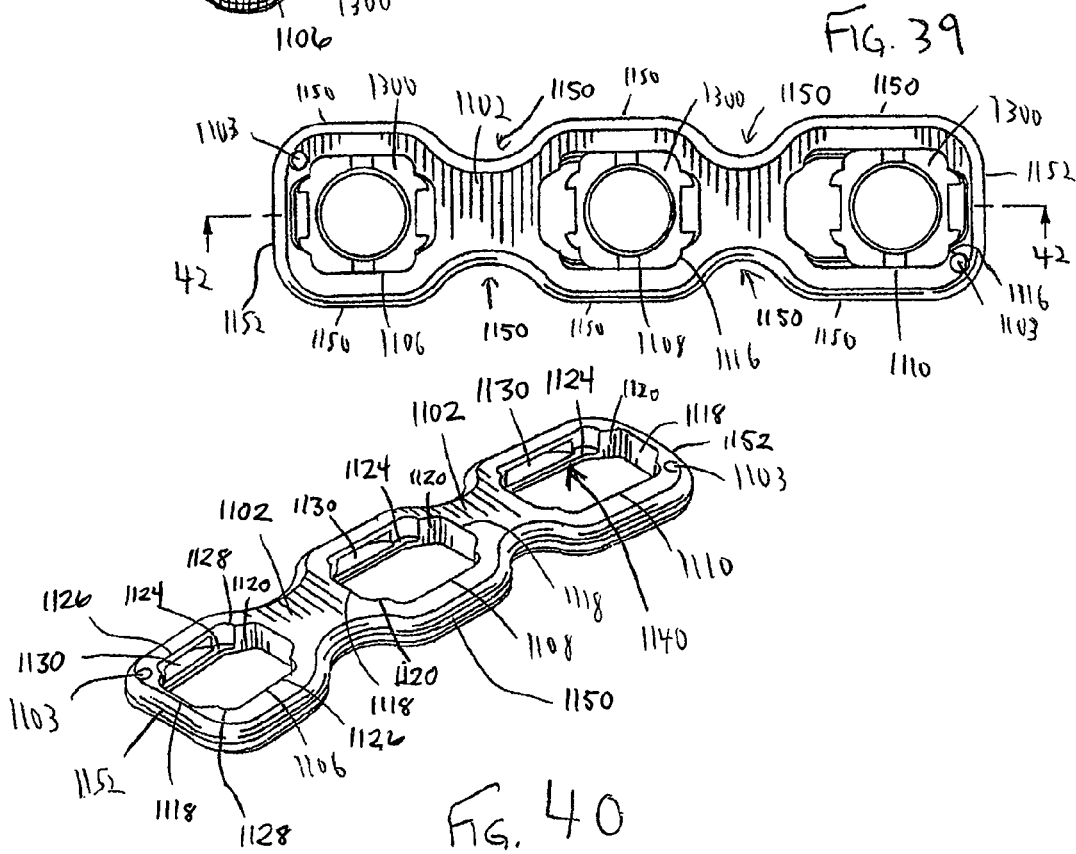
FIG. 39
FIG. 40

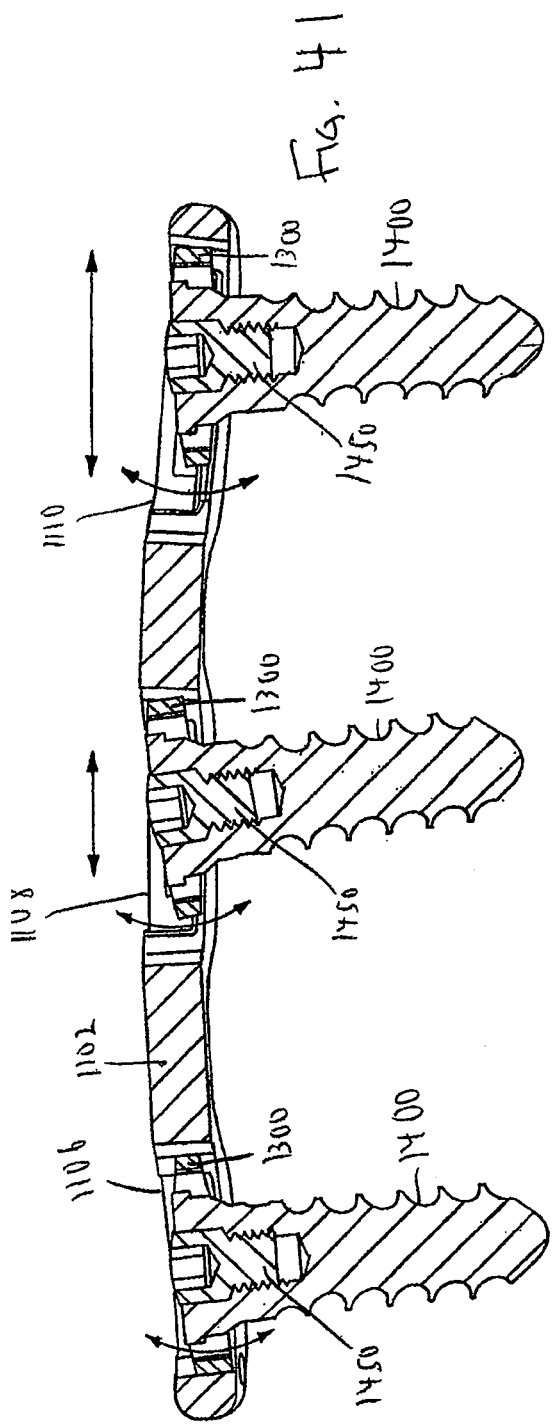
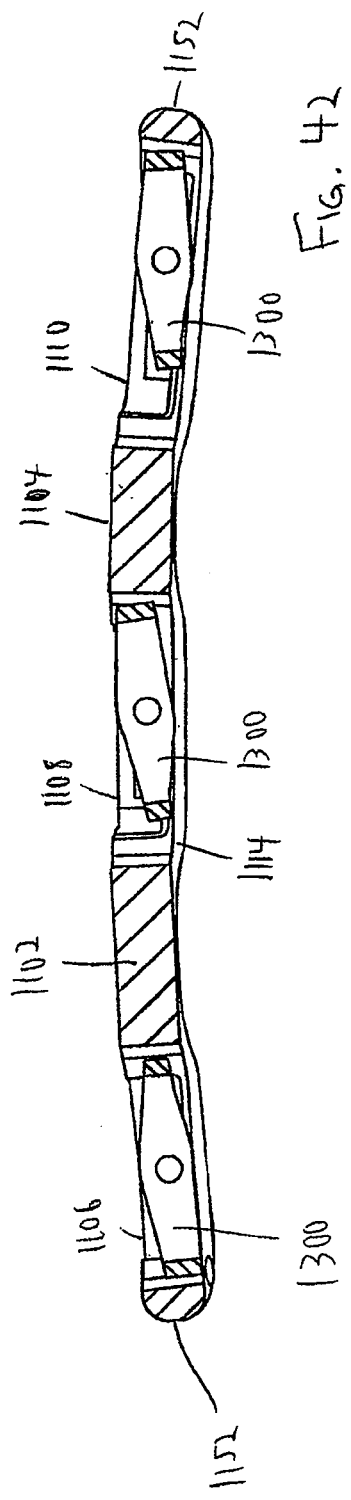

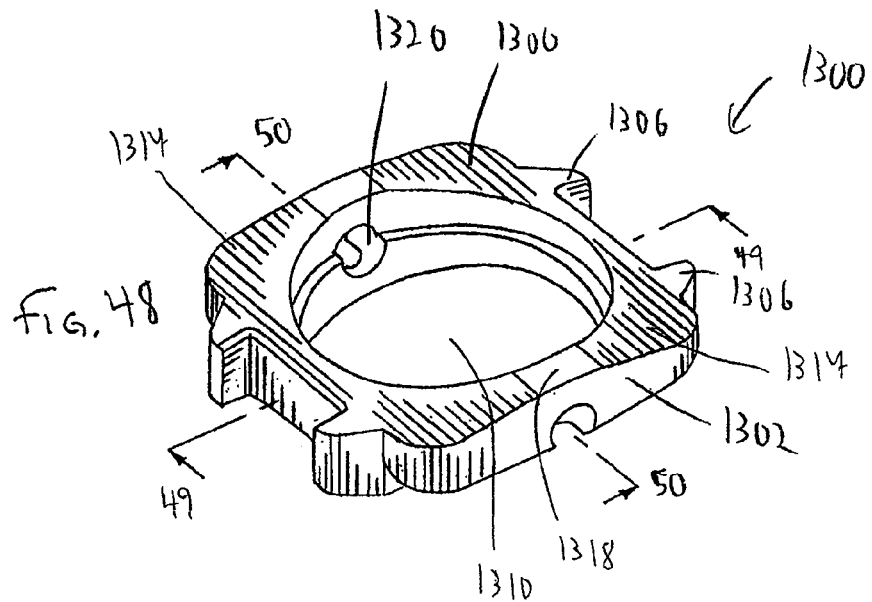
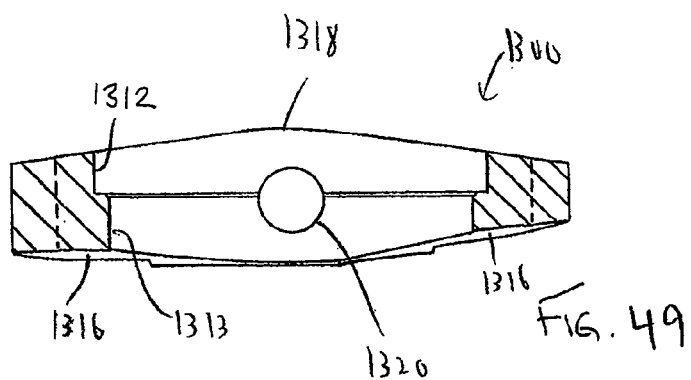
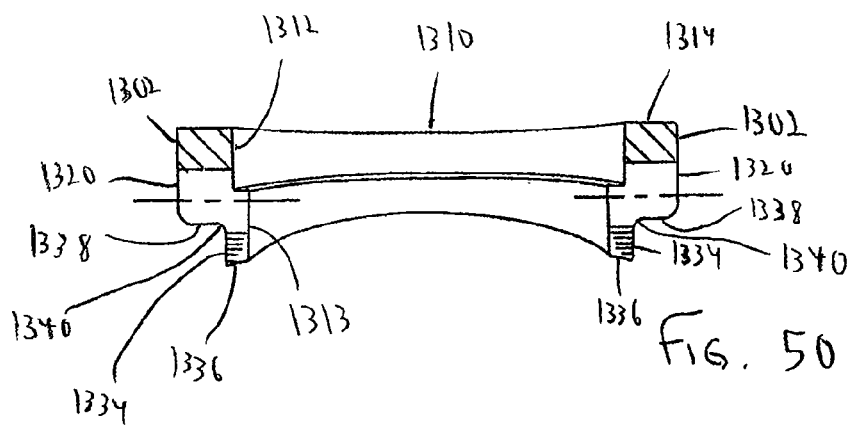

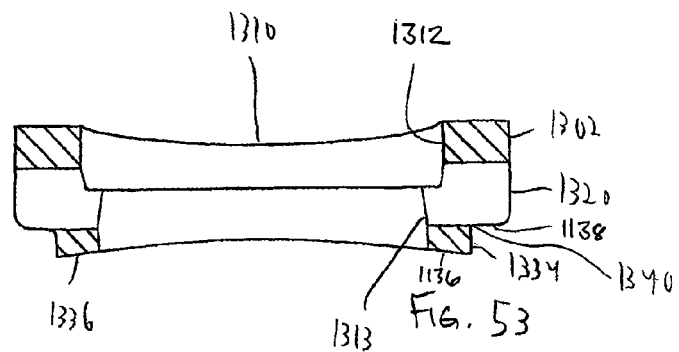
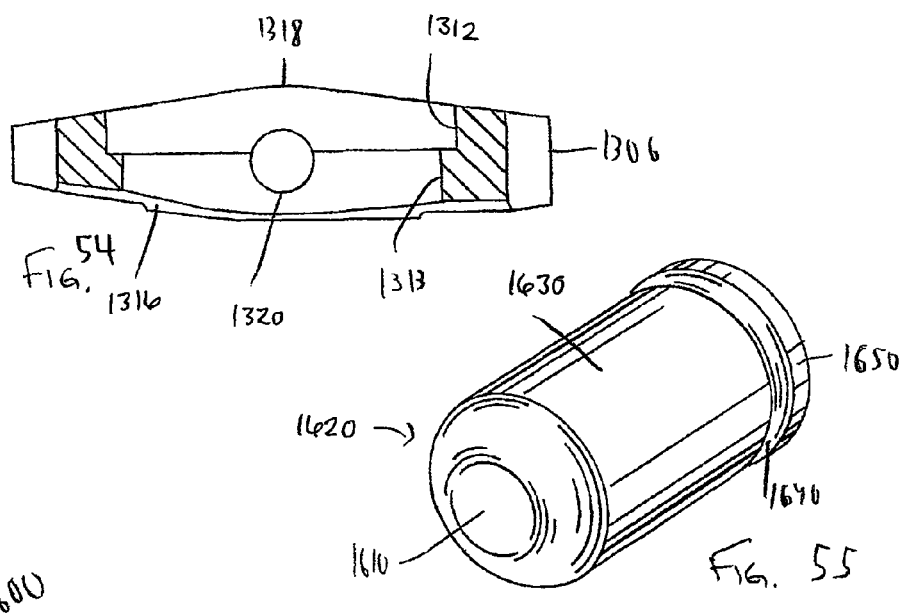
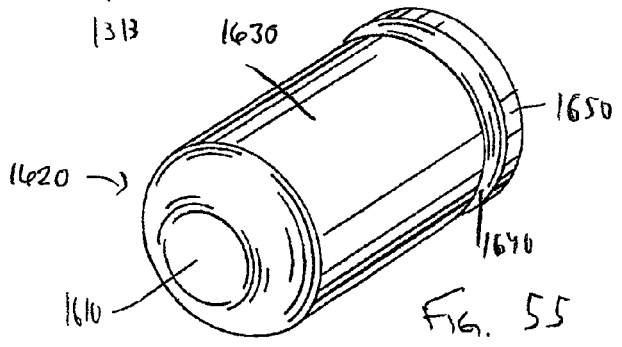
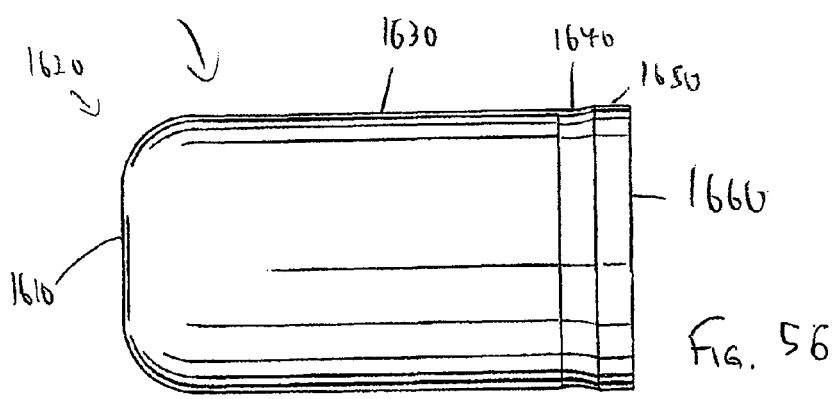

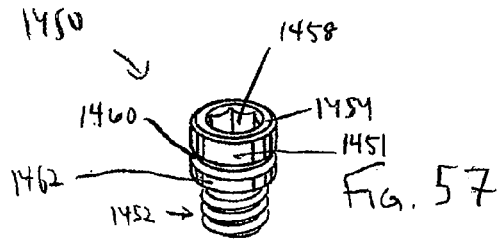
Fig. 57
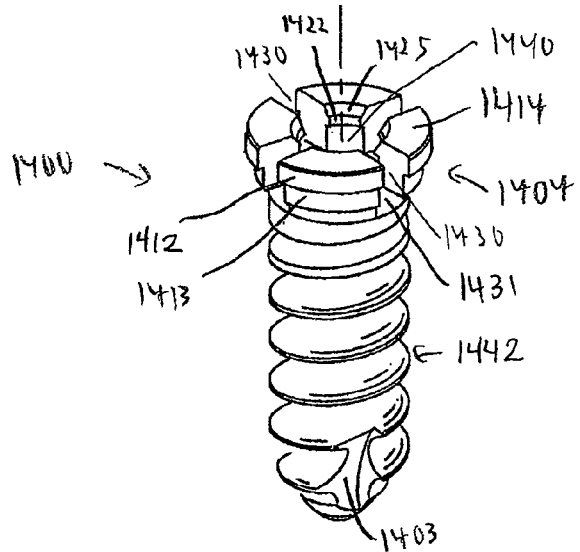
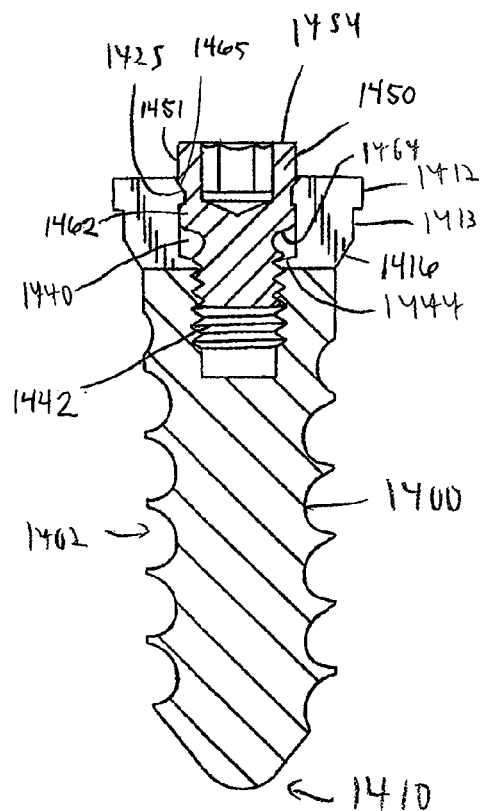
Fig. 58
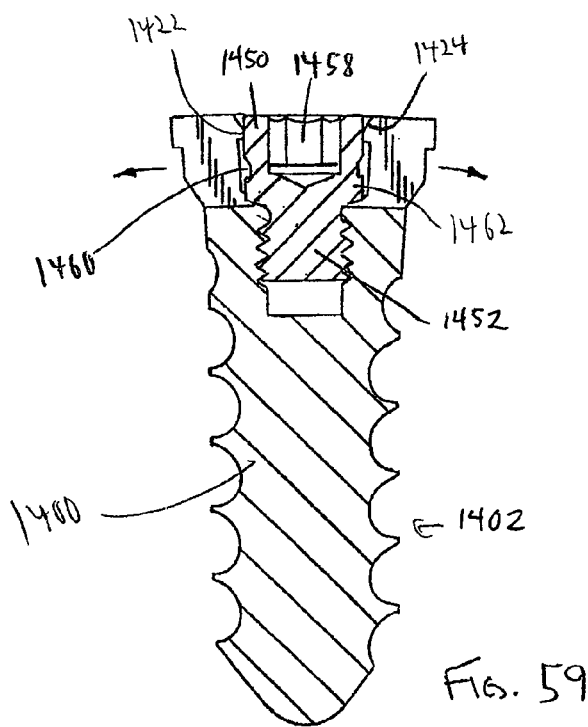
Fig. 59

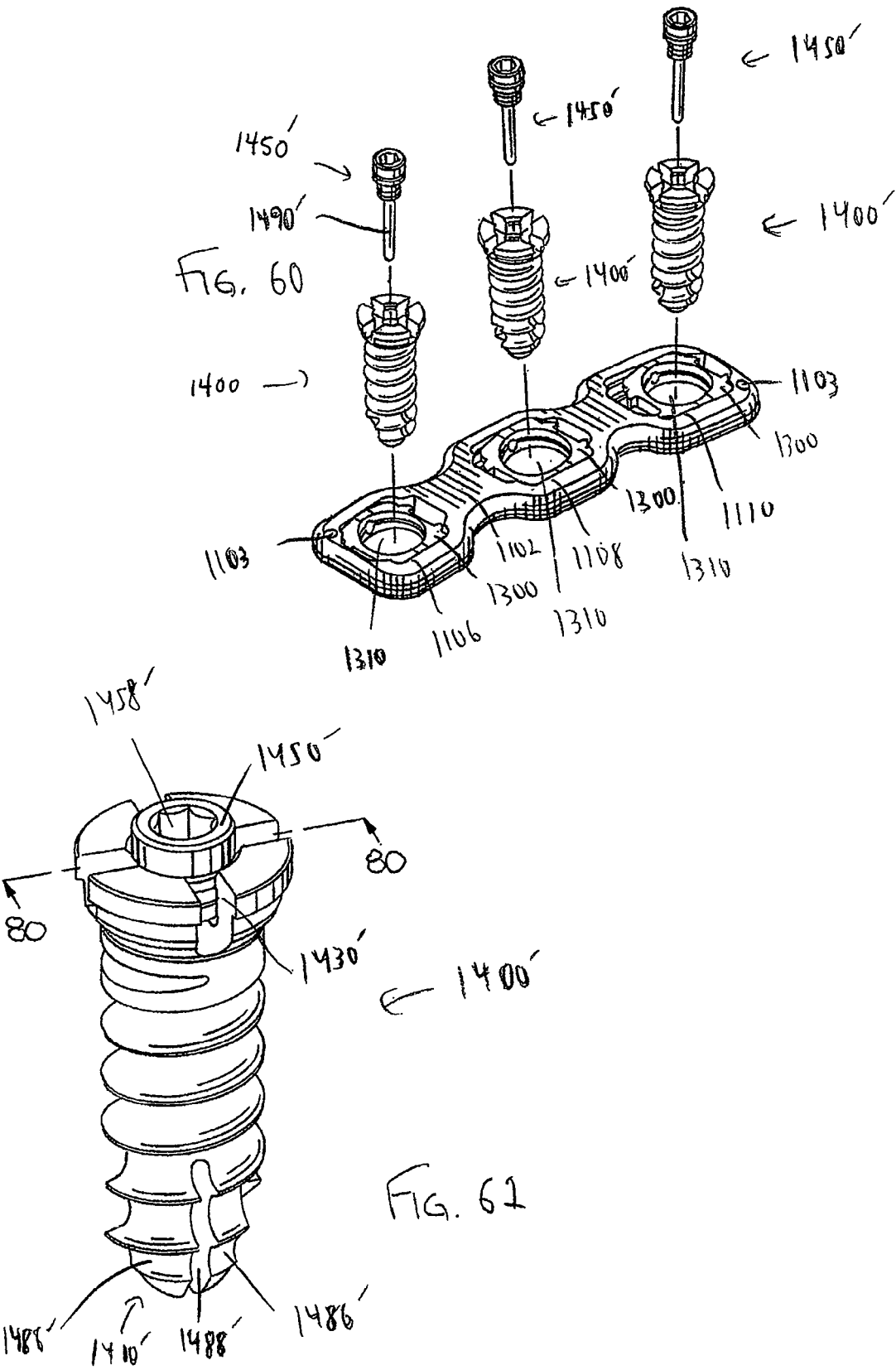

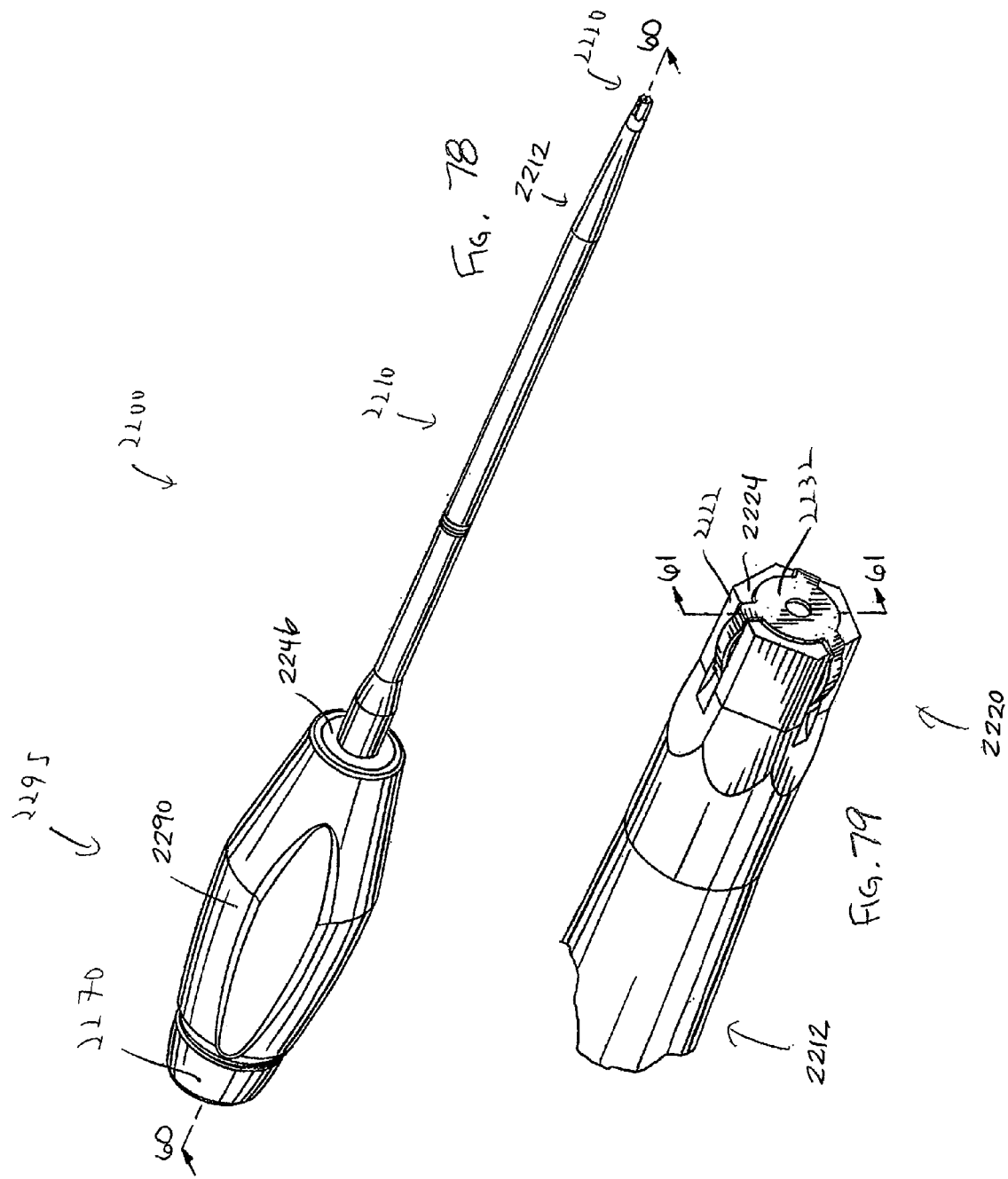

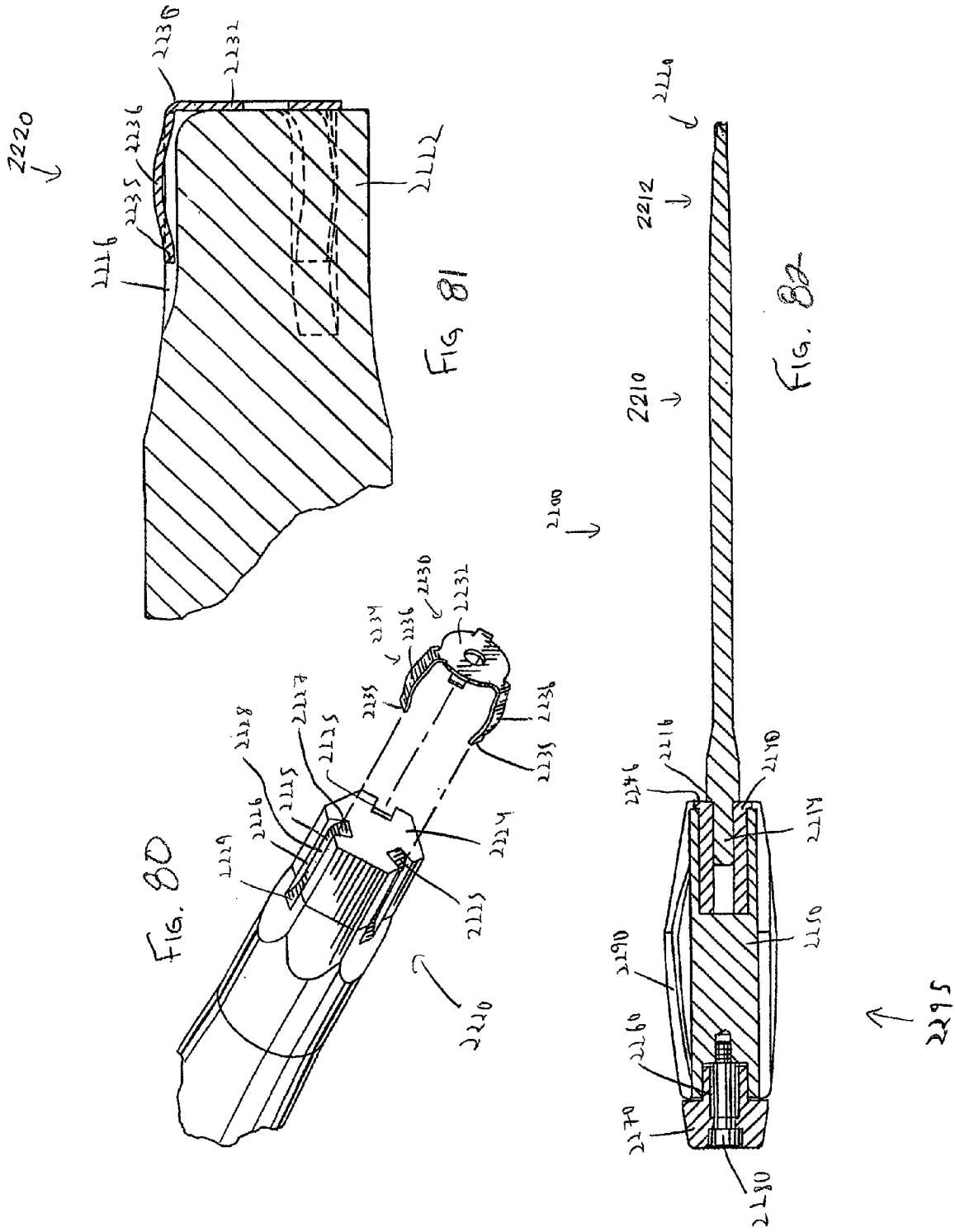

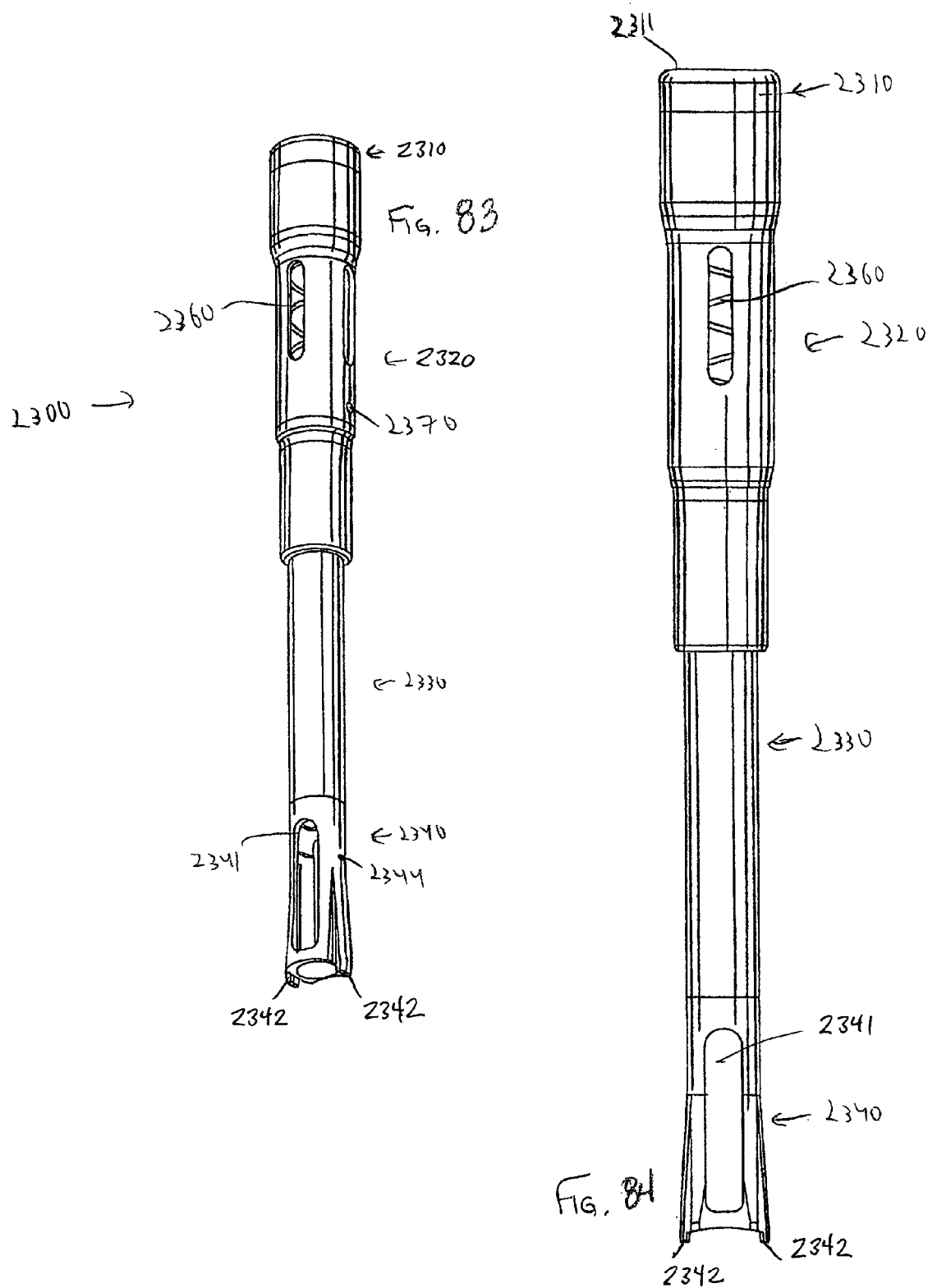

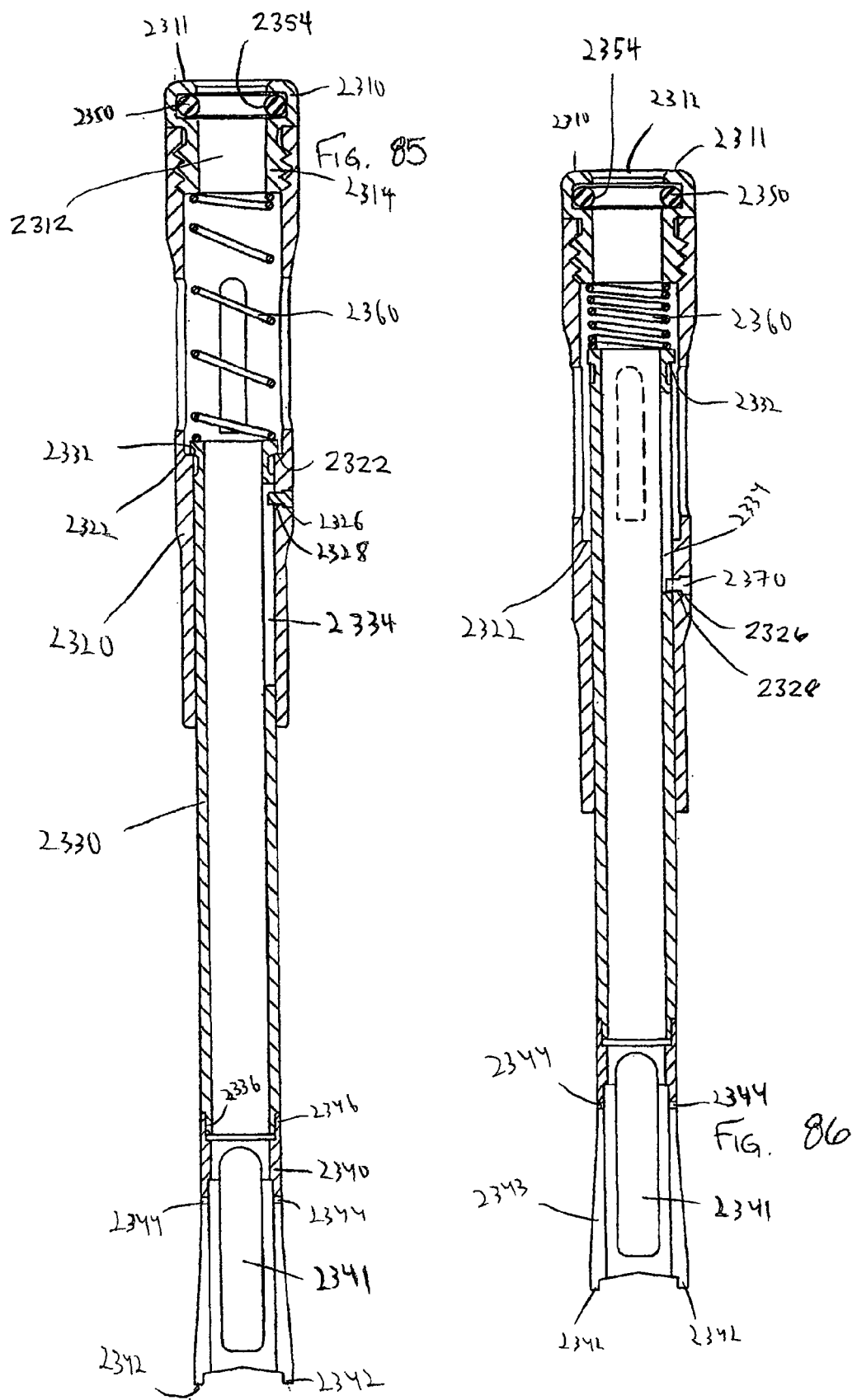

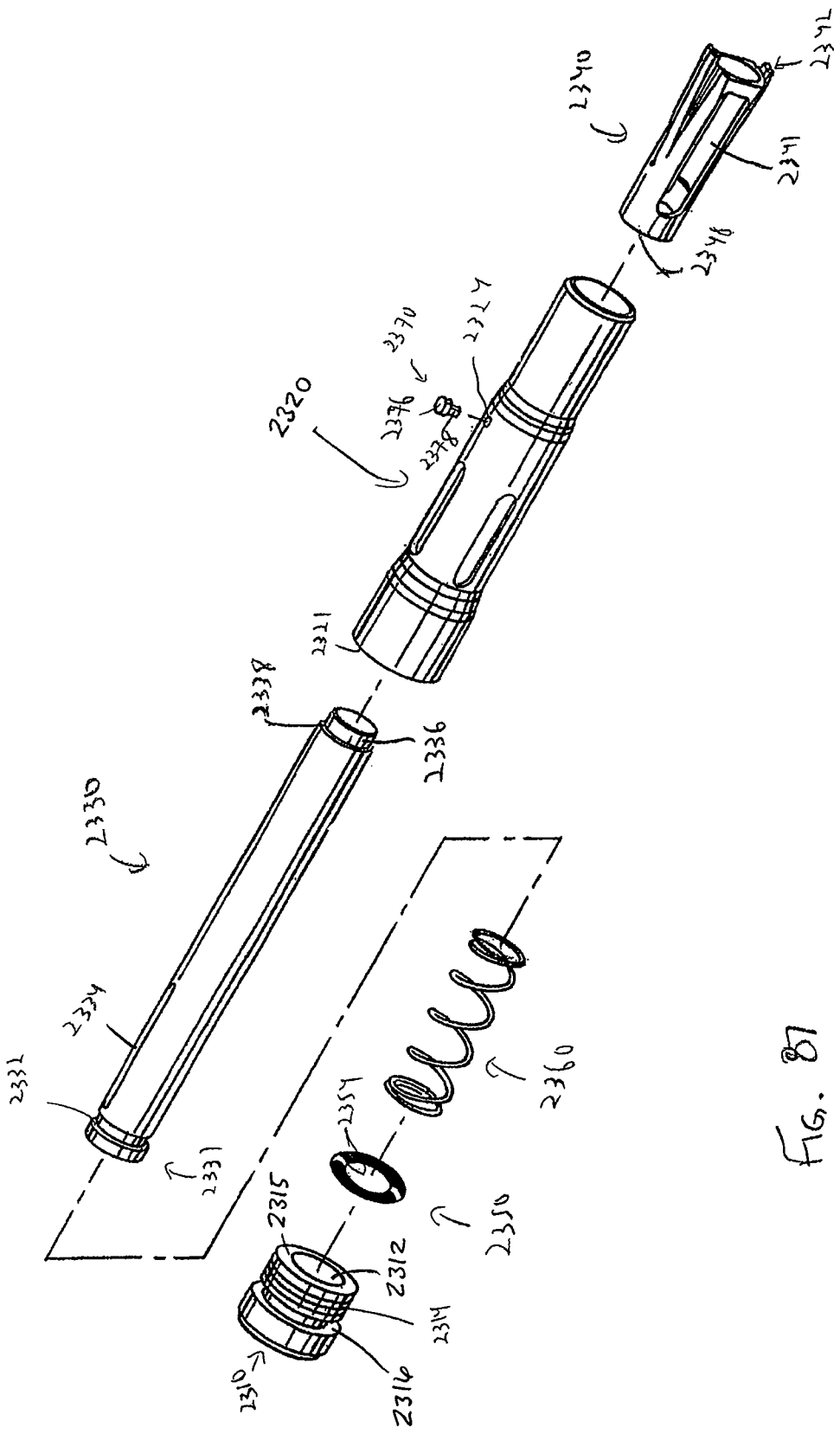

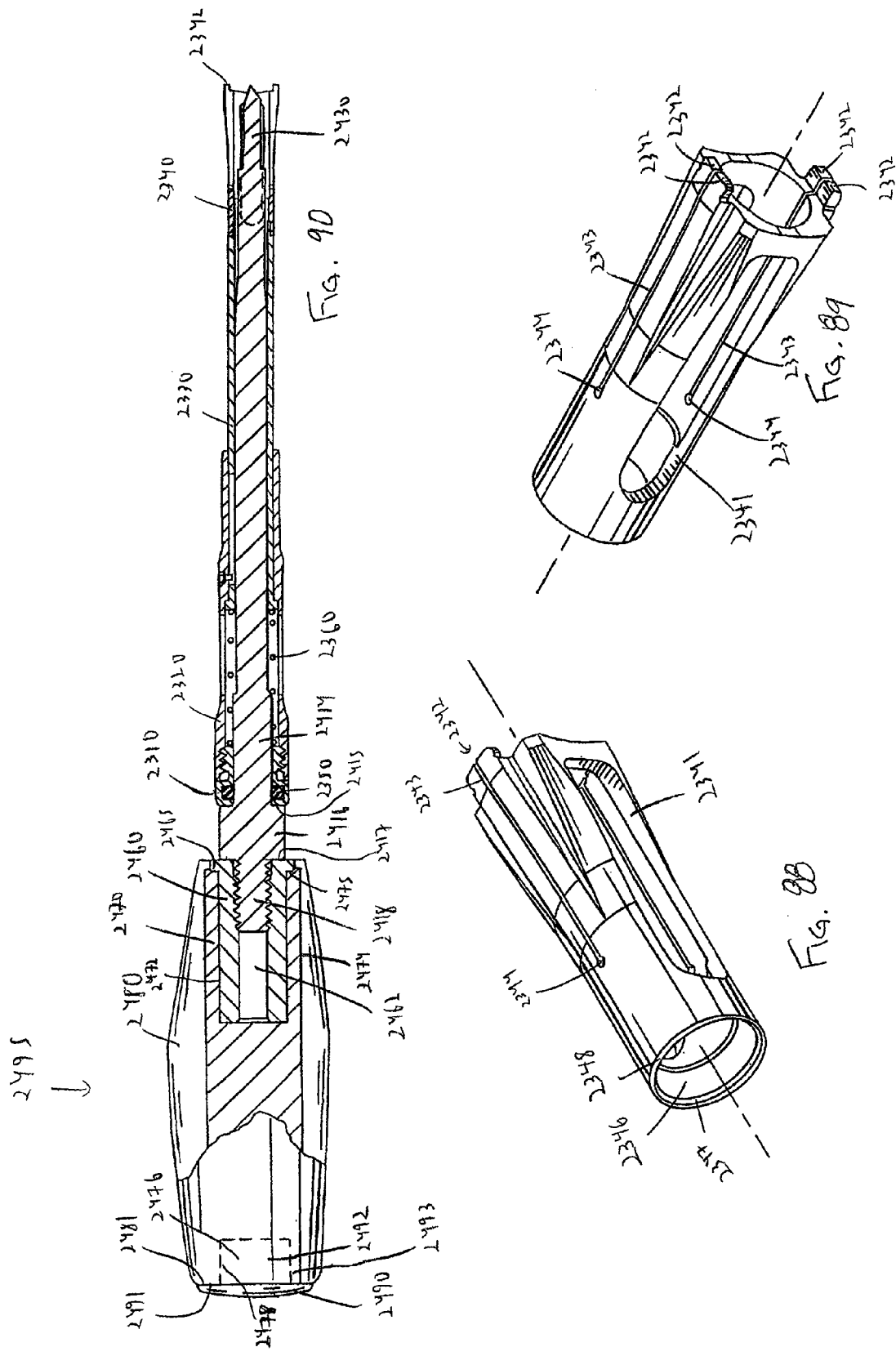

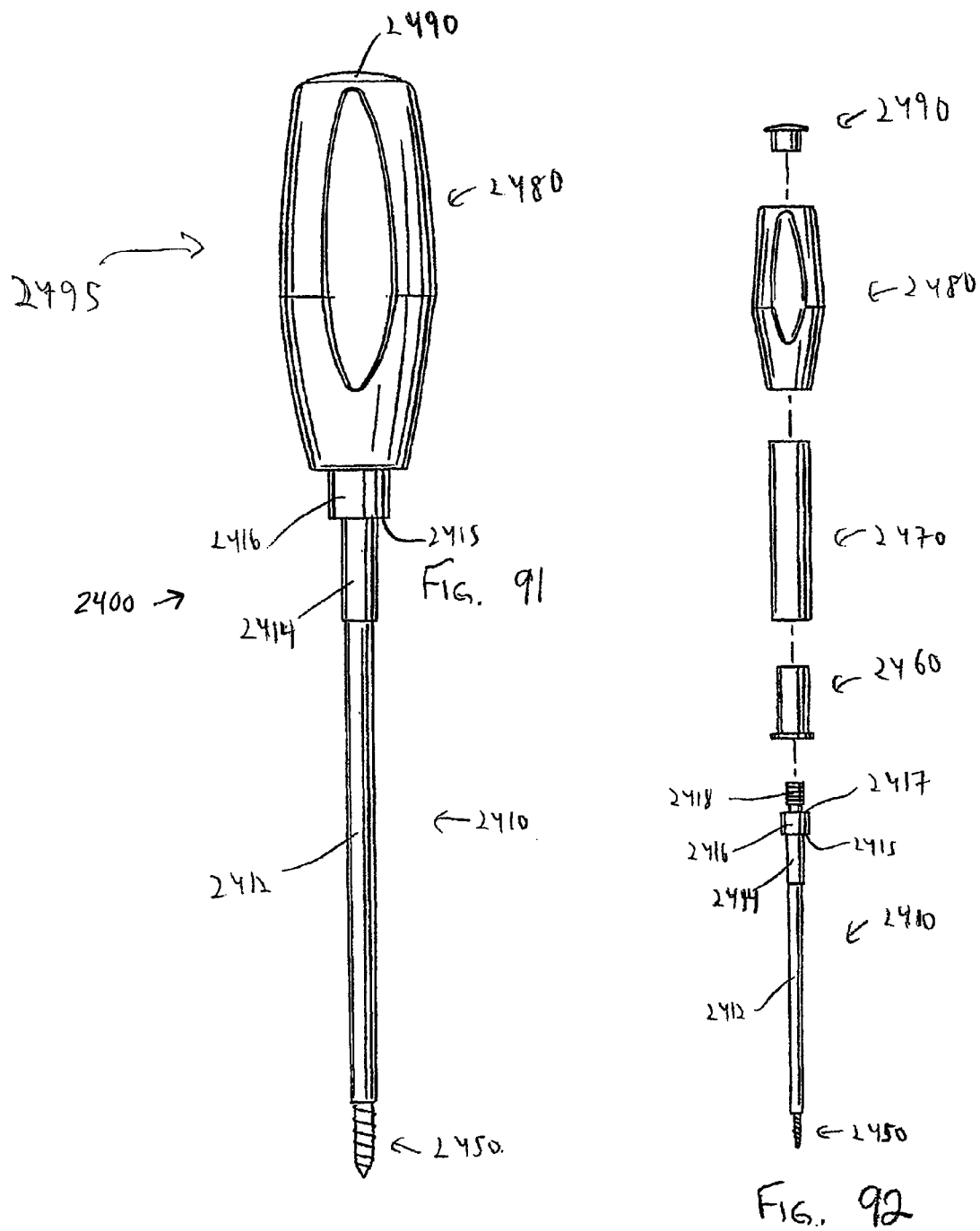

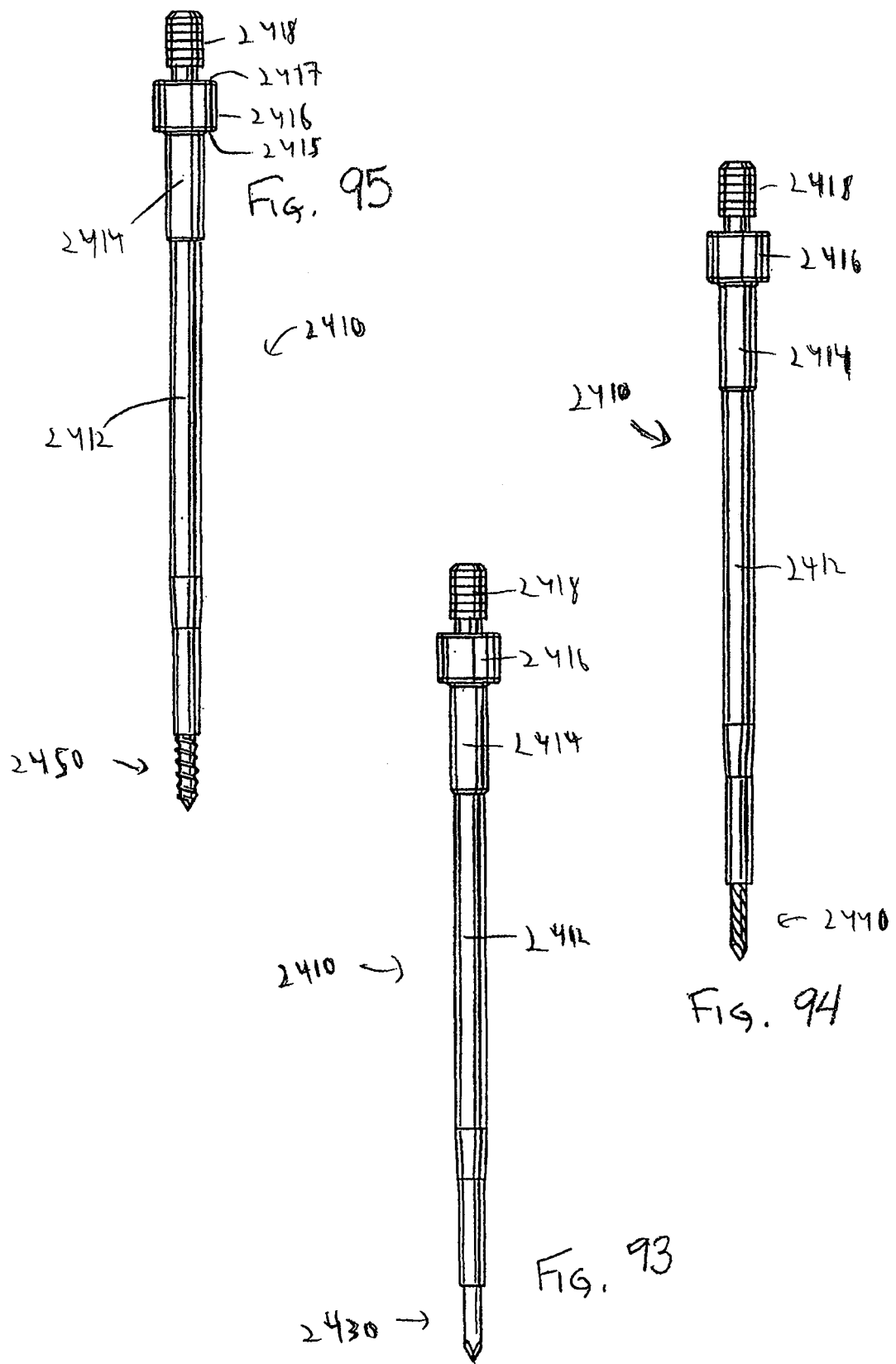

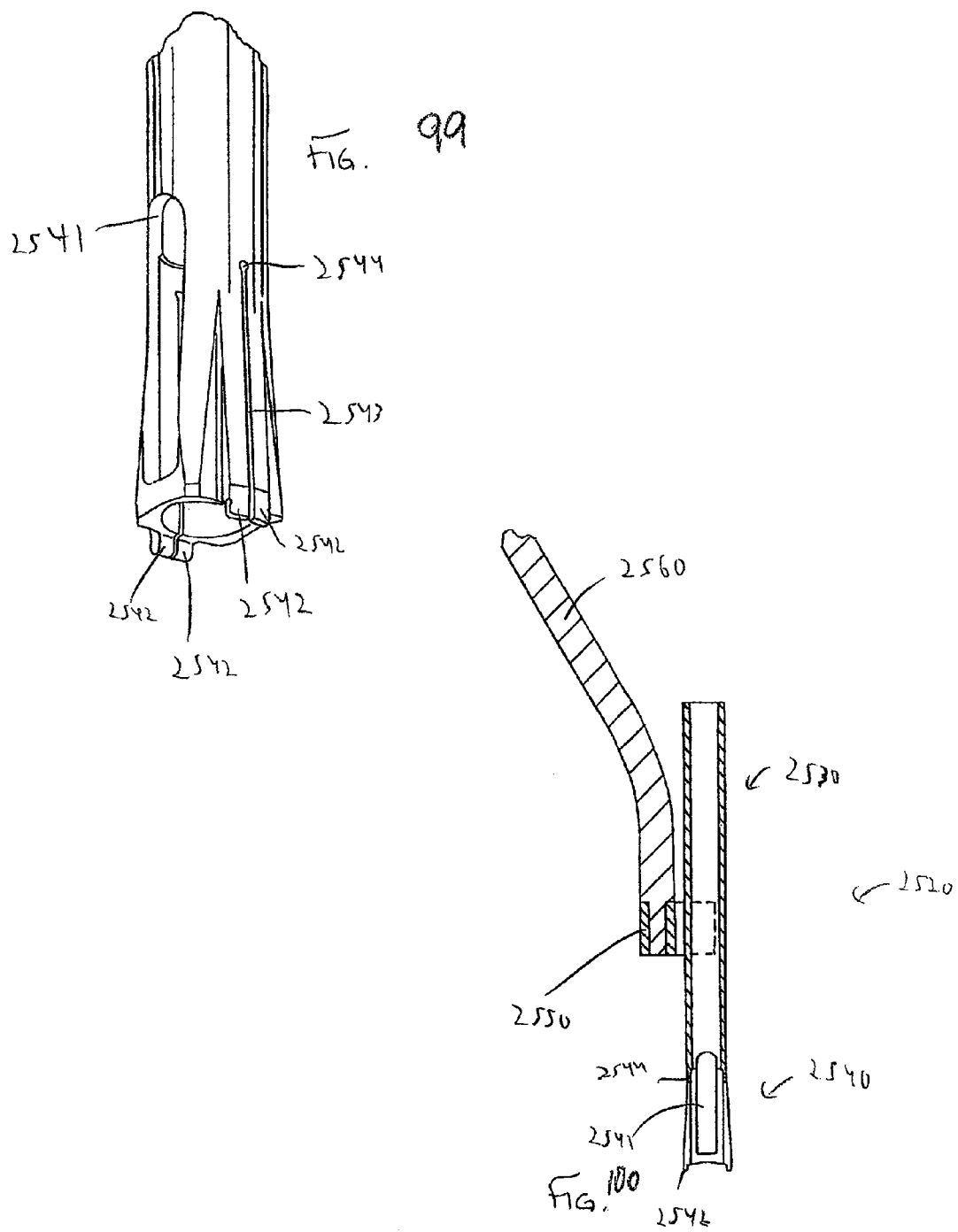

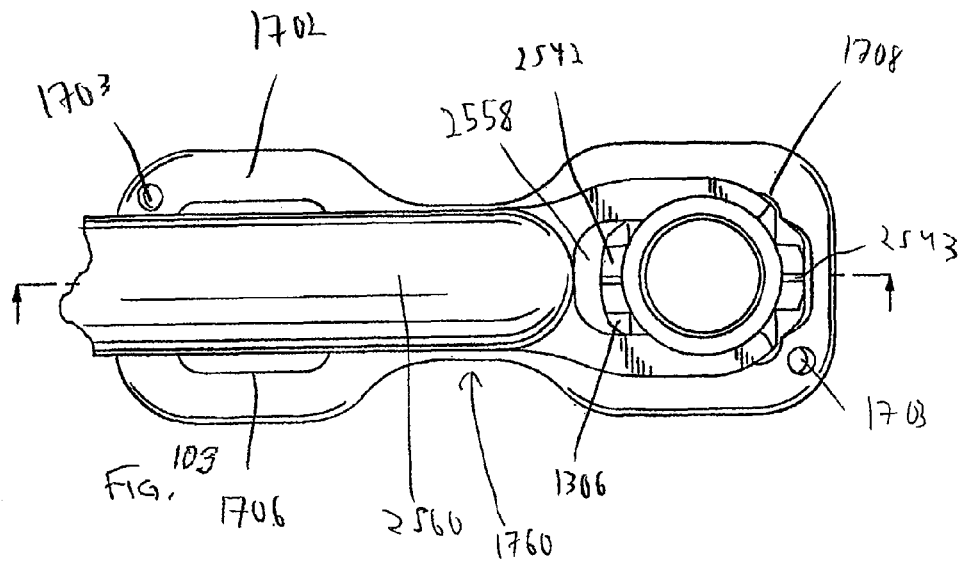
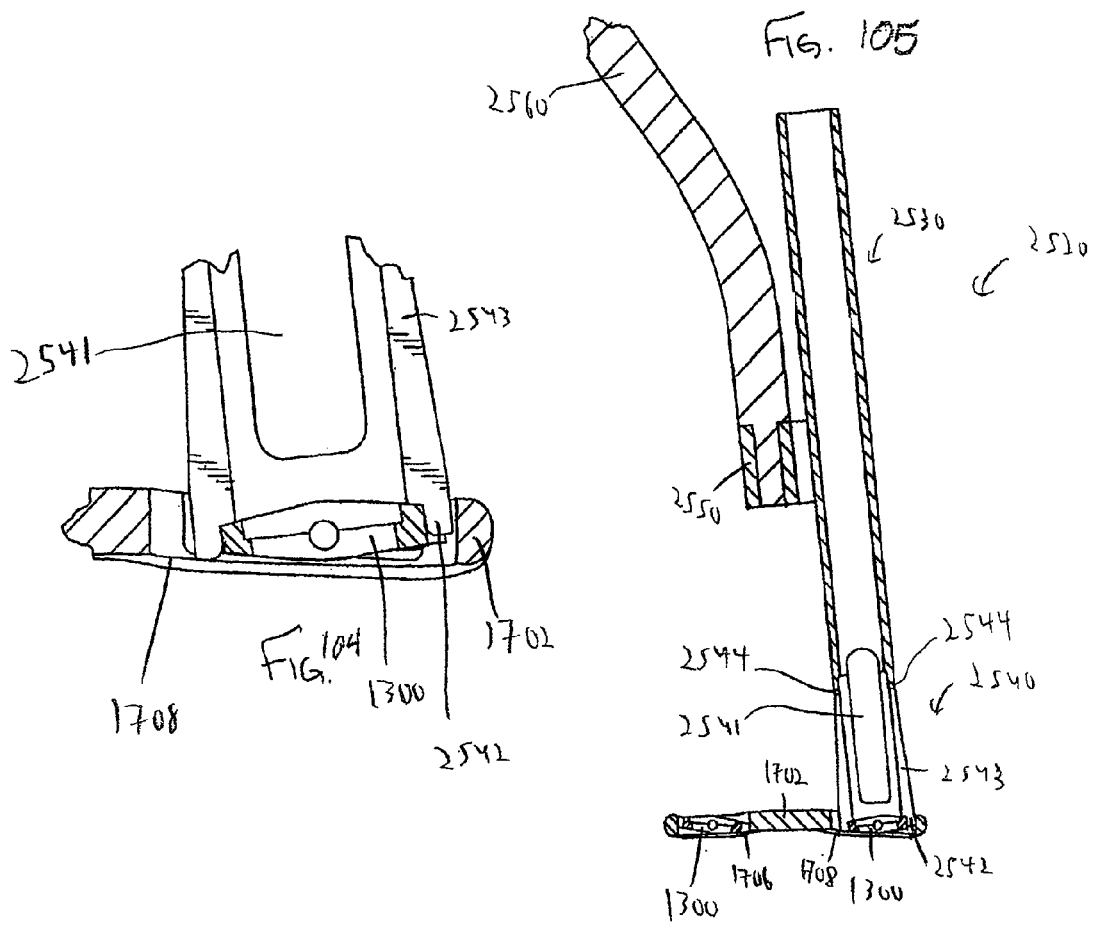

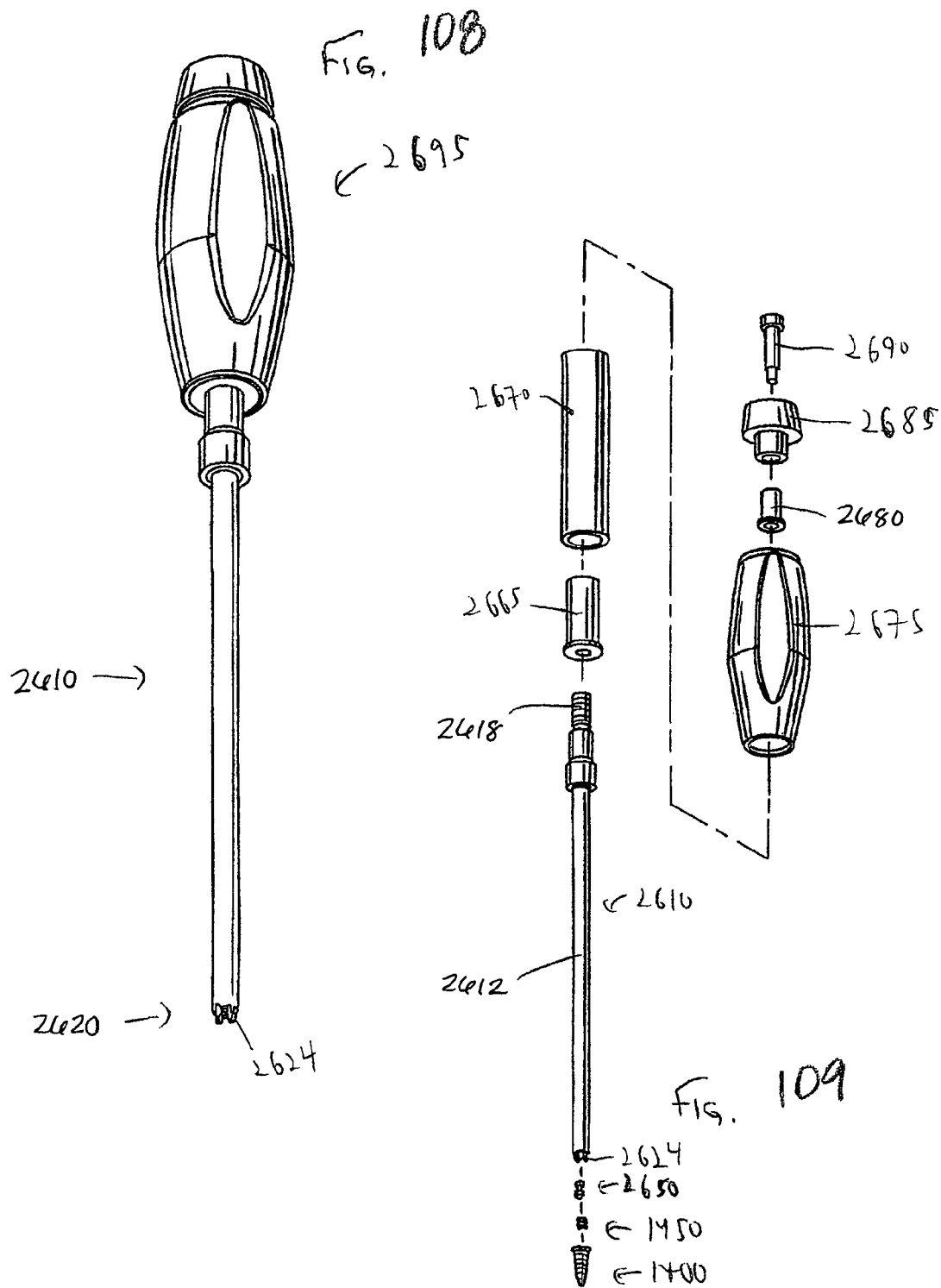

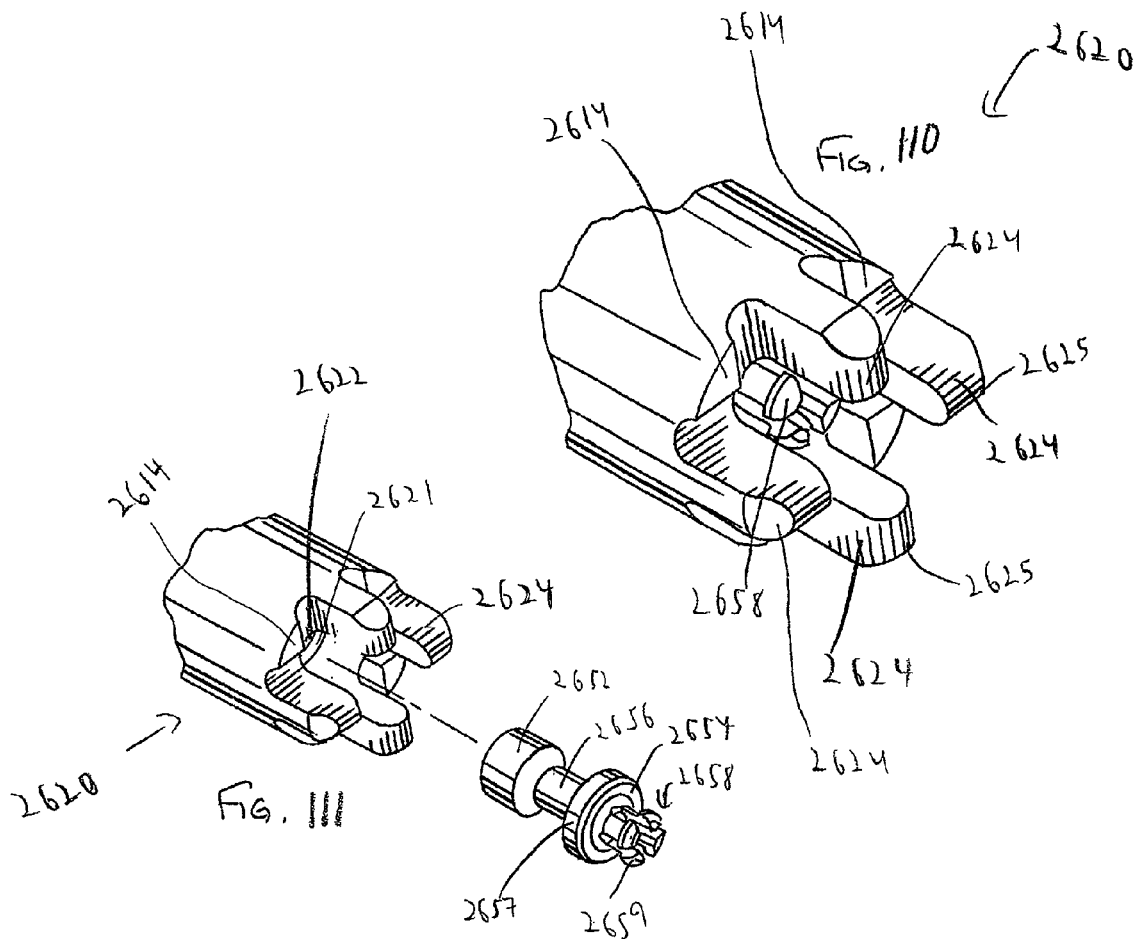
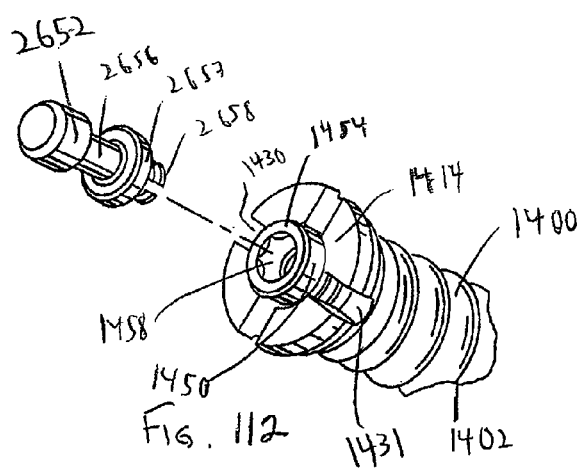

BONE PLATE SYSTEM

CROSS-REFERENCE TO RELATED APPLICATIONS

This application claims priority to U.S. Provisional Application Ser. No. 60/947,873, filed Jul. 3, 2007, and entitled "Bone Plate System"; and U.S. Provisional Application Ser. No. 61/024,287, filed Jan. 29, 2008, and entitled "Monoplate Bone Plate Guide," which are both hereby fully incorporated by reference as if set forth herein.

FIELD OF THE INVENTION

The invention relates to bone plate systems and, more particularly, to a bone plate system that allows for motion of the bone anchors relative to the bone plate member.

BACKGROUND OF THE INVENTION

There are presently many different types of plate and fixture systems for securing two or more bones or bone fragments in relative position so that the bones may fuse or heal, or so that tissue adjacent the bones may heal without disruption from the movement of the secured bones. As used herein, the term bone may refer to a bone, or a bone fragment or portion, and the term may refer to a portion of a bone that is covered with another material, such as the endplates covering the top and bottom surface of a vertebra. Also as used herein, the term fusion refers to the joining of materials, such as bone or graft material, and the fusion site is the entire region in which fusion may be desired. These systems have been used to secure spinal vertebrae and, more specifically, cervical vertebrae.

Bone plate systems are typically used to assist or direct spinal fusion or vertebral healing procedures. These procedures promote earlier post-operative patient mobility and improve success in correcting spinal deformities while decreasing the need for post-operative collars and the incidence of graft dislodgement if a graft is used.

Furthermore, these systems have been found to assist in controlling and/or exerting a compressive loading force applied to the surgical site. By applying a compressive load, it has been found that bone heals more optimally and with greater integrity, a principle known as Wolff's law.

Many prior bone plate systems are relatively wide, requiring a wide bone plate and/or two bone anchors per vertebrae to achieve an acceptable level of torsional stability such that the plate is capable of limiting the rotational motion of the interconnected vertebrae relative to one another to a large enough degree that a graft will take and/or the spine will recover properly. Other previously known bone plate systems offer a narrow portion over at least one vertebra and a widened portion over at least one other vertebra wherein the narrow portion requires only one bone anchor per vertebra and the widened portion requires two bone anchors per vertebra. In either case, bone plates with relatively wide profiles or a wide portion in addition to a narrow portion have a tendency to encroach upon and/or irritate the esophagus and other soft tissues of the patient during the recovery period. Furthermore, plate members with relatively wide profiles may require a larger incision and path of entry into the body than bone plate systems with smaller profiles, causing the patient extra pain and discomfort and a resulting in a longer recovery time. In addition, many of these systems require two bone anchors to be inserted into a least one vertebra, requiring a larger amount of time for bone plate installation and increasing the risk of degrading the structural integrity of the vertebra.

In addition, some known prior bone plate systems have attempted to use smaller profile or narrower bone plates with protrusions or spikes that engage the bone to offer enhanced torsional resistance. This method has clear drawbacks because the bone-engaging spikes may scratch or indent the bone, causing damage to the osseous tissue. It is also easily foreseen that if this resistance is overcome, the surface of a bone with which the bone plate is engaged may be scraped and/or chip due to the presence of these protrusions. The spikes may also harm or cause swelling of the intervertebral discs.

Some prior bone plate systems seek to provide a compressive force while allowing the vertebrae to settle naturally under the force of gravity and the weight of the head by offering bone anchors such as screws or alternatively coupling members that couple the screw heads to the bone plates that can pivot with respect to the plate as the vertebrae shift, settle, and/or curvature of the spine is altered. Many previous bone plate systems do not even allow such motion, and many that do provide inadequate control over the manner in which the vertebrae settle under this compression. These designs do not properly discipline the spine, allowing the screws to angle however the spine is inclined to shift, and thus these designs may be ineffective in keeping the spine from exhibiting curvature in the coronal plane as the vertebrae settle under the compressive loads. Additionally, if this shifting or settling of vertebrae is improperly or inadequately accounted for, additional stress may be added to the vertebrae and an undesirable load path through the spine may be created, hindering the recovery, grafting, and/or fusion process.

Another manner for permitting compressive loads between joined bones is to utilize a dynamic plate having at least one elongated screw aperture that allows settling of the vertebrae by gravity and the weight of the head by allowing at least one secured bone and its associated bone anchor to move relative to the plate. However, heretofore known arrangements of standard and dynamized apertures in such plates provide less than optimal capacity for controlling the movement and/or compression between more than two tiers of secured vertebrae and/or many previously known bone plates did not provide sufficient movement to allow the spine to settle naturally as a portion of the spine is compressed during the recovery period. Inasmuch as these prior bone plate systems allowed for some settling of the spine, this settling would cause the spine to be inclined to exhibit an altered degree of curvature, which prior dynamic bone plate systems failed to accommodate. If the spine is not allowed to adapt to this different degree of curvature and thus reach a more stable configuration, an undesirable or improper load path through the spine may be created, hindering the recovery, grafting, and/or fusion process.

Another shortcoming of many bone plate systems is the backing out or loosening of the bone anchors, which are often bone screws. If the bone screws loosen, the bones are not properly secured and may be allowed to move relative to one another in an uncontrolled manner. This may compromise the ability to achieve optimal bone fusion and bone alignment, and it may lead to loss of graft material and damage or loss of bone. Furthermore, when the plate is a dynamic or dynamized plate, such that at least some screws may be permitted to move relative to the plate, these issues may be further compounded or exacerbated by a screw backing out. Additionally, in the case of anterior cervical plates, a bone anchor backing out could hinder swallowing and cause irritation or even a puncture wound to the esophagus, which may lead to infection or even death.

Accordingly, there is a need for improved bone plates, bone plate systems that impede screw back-out, and improved tools and methods for utilizing bone plate systems.

SUMMARY OF THE INVENTION

In accordance with the present invention, several embodiments of bone plate systems as well as tools, instruments, and methods for installing the same are provided. The present bone plate systems overcome shortcomings of prior bone plate systems and generally allow motion for the bone anchors such that they may move relative to the bone plates to accommodate shifting or settling of secured vertebrae while offering desirable levels of control and predictability of this motion. The present invention further includes a new and novel approach to combining a narrow bone plate profile with enhanced torsional stability.

In one form of the present invention, a bone plate system is provided having an elongate plate member and a plurality of throughbores of the plate member. A pivot base is received in one of the throughbores with the pivot base having an opening configured to seat the head end of a bone anchor that may be driven into spinal bone. The pivot base and plate member have at least one pivot member extending therebetween and the pivot base and bone anchor pivots relative to the plate member about a pivot axis defined by the pivot member. In this way, the pivot base can exhibit well controlled pivoting motion relative to the plate to allow the spine to settle to a desirable configuration and accommodate shifts in spinal curvature.

In another form of the present invention, a bone plate system is provided having an elongate plate member extending along an axis thereof and a plurality of throughbores of the plate member. The throughbores are configured to receive a base member which has a bone anchor member driven therethrough, the head end of the bone anchor member able to be seated within an opening in the base member. The base member has a substantially rigid body, and seating the head end of the bone anchor therein does not deform the body of the base member. The rigid base portion and the throughbore of the bone plate member are configured to allow controlled motion of the base member and associated bone anchor member relative to the plate member even after the bone anchor member has been driven into bone and the head end of the bone anchor member has been seated within the opening of the base member. In this way, rigid base members are provided that exhibit controlled motion relative to the plate to accommodate spinal shifting and/or changes in spinal curvature.

In one form of the present invention, a bone plate system is provided having an elongate plate member with a plurality of throughbores extending therethrough. Each throughbore is configured to receive a pivot base, each pivot base having an opening to receive a bone anchor member having a head end which is seated within the opening of the pivot base. Cooperating surfaces of the pivot base and the throughbore of the plate member allow for both translation and pivoting of the pivot base and bone anchor member relative to the plate member even with the bone anchor member driven into bone and the head end of the bone anchor member seated in the opening of the pivot base. Thus, settling of the vertebrae and changes in spinal curvature can be accounted for, which is desirable because if pivoting alone may not account for the expected settling of a patient's vertebrae, a harmful load path may be created through the spine, hindering the recovery, grafting, and/or fusion process.

In another form of the present invention, a bone plate system is provided having an elongate bone plate member extending along an axis thereof. The bone plate member features a plurality of throughbores each configured to receive a base member therein, and at least one throughbore has substantially straight surfaces that extend in a direction parallel to the axis along which plate member is elongated. The base member has an opening therethrough, the opening configured to receive a bone anchor member for being driven into bone, and the head end of the bone anchor member is configured to be seated within the opening of the base member. The base member has opposite, straight sides that are in confronting relation with the straight, axially extending surfaces of the throughbore to keep the base member and corresponding bone anchor member from turning in the throughbore due to torque applied to the base member via the seated head of the bone anchor member. In this way, the confronting straight surfaces of the plate member throughbore and straight sides of the base member may enhance to the overall torsional stability of the bone plate system, allowing the plate member to have a narrow or monoplate configuration, for example, with desirable mechanical properties. Bone plate systems with more narrow profiles tend to cause less irritation or harm to the surrounding soft tissues, and, in the case of anterior cervical plates for example, a narrow plate member profile may result in less encroachment and/or irritation to the esophagus.

In one form of the present invention, bone plate systems are provided, the systems having a bone plate with at least one throughbore therein. In a preferred form, the plate features one throughbore per level or tier, each throughbore being configured to receive a pivot base therein. The throughbores and pivot bases feature opposite, straight sides and as a result the throughbores and pivot bases preferably have generally polygonal profiles, and, more preferably, the generally polygonal profiles are generally rectangular profiles, the opposite straight sides providing enhanced torsional stability to the bone plate systems.

In another form, the throughbores in the bone plate feature side walls that run generally parallel to the longitudinal axis of the bone plate, the side walls having a cavity defined therein. The pivot bases have an opening extending therethrough, the opening defining at least one side wall, the side wall having at least one aperture that extends through the side wall in a direction that is transverse and preferably orthogonal to the longitudinal axis of the bone plate. To mount the pivot base to the bone plate, a pivot member such as a pin is inserted into the aperture of the pivot base, a portion of the pin projecting into the cavity in the bone plate.

In one form the pivot base is free to pivot relative to the plate about a pivot axis defined by the pin and preferably within a predetermined range of motion. If the bone plate system is a dynamic bone plate system, at least one tier of the bone plate will feature a throughbore that is elongated along the longitudinal axis of the bone plate such that the pivot base is allowed to translate relative to the bone plate as well as pivot about the pivot axis defined by the pivot pin.

Additionally, in a preferred form, the bone plate is an anterior cervical plate, and during installation of the bone plate system, the plate is placed over a plurality of cervical vertebrae with each tier and corresponding throughbore in the bone plate aligned to a corresponding individual vertebra, forming a single row of throughbores. One bone anchor per tier is driven into a corresponding vertebra, with the head end of each bone anchor being seated in the opening defined by each pivot base such that the bone anchor and pivot base pivot and, in the case of a dynamized throughbore, translate as one relative to the plate and the pivot base and bone anchor are fixed relative to one another.

In one form, the rectangular profile of the pivot base offers the bone plate system enhanced torsional and rotational stability, meaning that the preferable generally rectangular profile of the pivot base may allow the pivot base to add to the overall torsional resistance of the bone plate system and aid in preventing a patient from rotating or twisting coupled vertebrae relative to one another in a manner that may hinder the recovery process by, for example, damaging a graft site or weakened vertebra. In addition, the small or narrow profile of the bone plate may cause less irritation to the esophagus and other soft tissues while allowing the bone plate system to be installed with a smaller incision than is necessary for bone plates with wider profiles. Furthermore, using only one bone anchor per tier may allow a shortened installation time, a bone plate system that is easier and less costly to manufacture, and cause less degradation to the structural integrity of the vertebrae.

In another form, the geometric configuration between the bone plate and the pivot bases provides clearances that accommodate the pivoting motion of the pivot bases relative to the plate. In a preferred form, this pivoting motion has a predetermined defined range. Due to the clearances, the geometric configurations, and the generally rectangular profiles of the pivot bases and throughbores in the bone plate, the pivot bases are generally constrained to pivot about an axis defined by the pivot members that mount the pivot bases to the bone plate, preferably allowing the pivot bases to pivot fore and aft with respect to the longitudinal axis of the bone plate. The freedom to pivot allows the bone plate system to accommodate at least a portion of the settling of the coupled vertebrae during the recovery period, as well as adapt to changes in spinal curvature. Generally, in the case of a three-tiered bone plate, the uppermost and lowermost bone screws will be installed at diverging angles with respect to one another, and as the vertebrae settle, these angles tend to relax. The preferable generally rectangular profile of the pivot bases also provides a degree of discipline to the coupled vertebrae, only allowing them to shift with respect to one another in the midsagittal plane but hindering shifts in the coronal plane.

In one form, the geometric configuration between the bone plate and the pivot bases features elongated or dynamized throughbores wherein the pivoting relationship is the same as described above, but the elongation of at least one throughbore provides the pivot base received therein with the ability to translate as well as pivot relative to the bone plate. Generally, at least one throughbore is a standard or non-dynamized throughbore, and the pivot bases disposed within dynamized or elongated throughbores are moved as far away from the standard throughbore as possible before the bone anchors are inserted. A dynamic bone plate may be used when a surgeon believes that the coupled vertebrae may experience more settling or shifting than pivoting alone could account for. In this case, the compressive forces and shifting of the vertebrae cause the dynamized throughbores to allow the pivot bases disposed therein to demonstrate controlled translational motion toward the standard throughbore as well as a predetermined range of angular motion, both working to accommodate settling of the vertebrae and possible changes in curvature. This combination may allow the spine more freedom to settle to a more stable configuration, which may lead to a more desirable load path through the spine and better promote the recovery, grafting, and or/fusion process.

In another form, the head end of the bone anchor is retained within the opening of the pivot base and is inhibited from backing out by a retaining member or clip. In this form, the pivot members that mount the pivot bases to the bone plate member are at least partially hollow and a portion of a resilient retaining member is configured to be received within the hollow portion of the pivot member, which in a preferred form is a pin. In this way, the retaining member keeps the pins from being removed from the apertures in the pivot bases and maintain a portion the pins in the cavities in the longitudinal side walls of the throughbores of the bone plate member. The retaining member covers at least a portion of the opening in the pivot base, and when a bone anchor is driven into corresponding vertebra, the resilient retaining member is deflected to allow the bone anchor to pass thereby. In a preferred form, when the head portion of the bone anchor is seated within the opening of the pivot base, the head portion acts as a secondary retainer to keep the pins within the apertures and a portion of the resilient retaining member within the pins. With the bone anchor has fully passed by the resilient retaining member, the retaining member returns at least partially to its original position and cover a portion of the head end of the bone anchor, inhibiting back out of the bone anchor while the bone plate system is installed within the body. In this form, the head end preferably features a hex-shaped aperture whereby a driver may engage the bone anchor.

In one form, the pivot members or pins that connect the pivot bases to the bone plate need not be hollow, and the pivot members feature an enlarged portion that creates a tight frictional or interference fit with the aperture defined in the side wall of the opening in the pivot base. In this form, the bone anchor features a resilient head portion, and after the head end of the bone anchor is seated within the opening in the pivot base, a locking member is seated within the resilient head portion of the bone anchor, expanding the head portion to create a tight frictional engagement between the head portion of the bone anchor and the pivot base to lock the bone anchor to the pivot base, which inhibits back out of the bone anchor while the bone plate system is installed within the body. In this form, the head end of the bone anchor preferably features cross-shaped or Phillips-style engagement slots, creating gaps that aid in configuring the head portion to behave in a resilient manner.

In another aspect, calipers may be provided for aiding a surgeon or clinician in selecting the proper size bone plate member. Measuring legs of the calipers enter the body, measure the distance between two points of interest on the surgical site, which may be, for example, desired insertion points for bone anchors. The calipers may further feature an indicator sleeve that rotates relative to a housing such that a measurement of the distance between the ends of the legs of the calipers may be obtained from the indicator sleeve. This differs from prior calipers used for selecting a proper bone plate member size. Prior calipers have legs which are extended to place the ends of the legs at two points of interest on the surgical site, but these calipers need the legs to be removed from the body and then compared either directly to available bone plates or measured by a ruler or measuring stick to choose a proper bone plate member size. The present calipers allow a surgeon to choose a proper bone plate size directly from the measurement obtained from the indicator sleeve, which may further reduce operation time and reduce the possibility of choosing an improper plate size.

In another aspect, the bone plate systems may utilize guides that aid in directing tools or instruments toward positions on the surgical site, such as, for example, bone anchor insertion points. The tools may be preparation tools used to prepare the bone anchor insertion sites, or the tools could be drivers used to drive the bone anchors into bone. In a preferred form, the guide will feature a tube portion and a base portion, the base portion operable to engage and pivot a pivot base to obtain the desired bone anchor trajectory. Additionally, in the case of dynamized apertures, the guides could be used to translate the pivot bases to be moved into alignment with the desired bone anchor insertion points, which are generally as far away from the standard or non-dynamized throughbores as possible with respect to the longitudinal axis of the bone plate.

In one embodiment, the guide is a fixed guide that may be used in conjunction with preparation tools or a driver. In a preferred form, the base portion of the fixed guide is configured to engage the pivot base that utilizes a resilient retaining member, and thus the base portion of the guide has at least one recessed portion to account for the configuration of the retaining member.

The driver to be used in conjunction with the fixed guide may be, in a preferred form, a generally hex-shaped driver. The tip of the driver features a retainer spring having a main body portion that abuts the end of the tip of the driver. The retainer spring further defines a plurality of resilient legs that project in a direction parallel to the longitudinal axis of the driver and fit into a plurality of grooves in the tip of the driver with each leg fitting into a corresponding groove. The legs feature a generally curved portion which extends above of the groove and project over the face of the hex portion of the driver, thus when the tip of the driver is inserted into a corresponding hex aperture of a bone anchor, the curvature of the curved portions of the retainer spring decreases and a load is applied to the hex aperture, aiding in retaining the bone anchor to the driver while the driver and screw are moved over the surgical site and down a throughbore of the fixed guide as the driver and bone anchor approach the bone anchor insertion site. The driver and retainer spring are intended to be removed from the hex aperture of the bone anchor after the head end of the bone anchor is seated in the opening of the pivot base and the resilient retaining clip covers at least a portion of the head end of the bone anchor to prevent back out.

In another embodiment, a guided sleeve may be used with the present bone plate systems. Preferably, the guided sleeve is configured to engage pivot bases that do not utilize a resilient retaining member to cover a portion of the seated head end of the bone anchor to inhibit back out, and the guided sleeve is configured to be used in conjunction with at least one preparation tool that may be used to prepare the desired bone anchor insertion site. The preparation tools would preferably be available in the form of an awl, drill, and tap, and a surgeon may prefer to use all, none, or any combination of these tools to prepare the bone anchor insertion site.

The guided sleeve is preferably biased to an extended position by an internally housed biasing or compression member, and this configuration may bias the tips of the preparation tools away from the bone when an affirmative load is not being applied to the tools by a surgeon or clinician. In a preferred form, shafts of the preparation tools are configured to be inserted only a predetermined distance into the guided sleeve, and an internal o-ring within the guided sleeve frictionally engages a portion of the shaft, acting to couple the preparation tool to the guided sleeve.

In one embodiment, a guide with an offset handle is also preferably used with bone plate system embodiments that do not utilize a retaining member that covers a portion of the seated head end of the bone anchor to inhibit back out. The guide is configured to be used with an awl, drill, tap, and/or driver, the driver for driving bone anchors into bone. Additionally, the guide features a coupling member which couples the offset handle to the guide tube or shaft, allowing a surgeon or clinician to actuate and position an engaged pivot base by actuating the offset handle. The coupling member further comprises a window or aperture which offers the surgeon an at least partial view of the base portion and the pivot base. The view path allowed by the coupling member may be advantageous in aligning the guide to the pivot base while the pivot base is brought into engagement with the base portion of the guide.

A driver may be used with the guide, and the driver preferably has a shaft with a tip portion featuring a plurality of protruding bone anchor head portion engagement members that generally form a cross-shape. The tip portion further defines a bore in substantial alignment with the central longitudinal axis of the driver, the bore configured to accept a portion of an insert. In a preferred form, the insert has a plurality of resilient teeth, and the bone anchor with a resilient head portion has a locking member partially inserted therein. A surgeon or clinician would receive the bone anchor with the locking member in the proud position (i.e. engaged but not fully seated). The head portion engagement members are configured to slide into slots that form the cross-shape in the resilient head portion and engage the bone anchor thereby. As the engagement members slide into the slots, the resilient teeth of the insert engage an aperture in the locking member, holding the locking member to the driver as the bone anchor is moved over the surgical site and down a throughbore in the guide toward the desired bone anchor insertion site. The bone anchor is preferably driven into the bone and the head portion is seated within the opening of the pivot base while the locking member remains proud, and then the locking member itself is intended to be driven until fully seated. Seating the locking member causes expansion of the resilient head portion of the bone anchor and creates a strong frictional engagement with the side walls of the opening in the pivot base, inhibiting bone anchor back out.

BRIEF DESCRIPTION OF THE DRAWINGS

FIG. 3 is a perspective view of the dynamized bone plate system of FIG. 2 without the bone anchors;

FIG. 4 is a top plan view of the dynamized bone plate system of FIG. 2;

FIG. 5 is a cross-sectional side view of the dynamized bone plate system of FIG. 2 taken along line 5-5 thereof;

FIG. 6 is a cross-sectional side view of the dynamized bone plate system of FIG. 3 taken along line 6-6 thereof;

FIG. 38 is an exploded perspective view of the dynamized bone plate system of FIG. 37;

FIG. 39 is a top plan view of the dynamized bone plate system of FIG. 37 without the bone anchors;

FIG. 40 is a perspective view of the bone plate of the dynamized bone plate system of FIG. 37;

FIG. 41 is cross-sectional side view of the dynamized bone plate system of FIG. 37 taken along line 41-41 thereof;

FIG. 42 is a cross-sectional side view of the dynamized bone plate system of FIG. 39 taken along line 42-42 thereof;

FIG. 48 is a perspective view of the pivot base of the dynamized or standard bone plate systems of FIG. 37, 45, or 44;

FIG. 49 is a cross-sectional side view of the pivot base of FIG. 48 taken along line 49-49 thereof;

FIG. 50 is a cross-sectional side view of the pivot base of FIG. 48 taken along line 50-50 thereof;

FIG. 53 is a cross-sectional side view of the pivot base of FIG. 48 taken along line 50-50 thereof in the opposite direction of FIG. 50;

FIG. 54 is a cross-sectional side view of the pivot base of FIG. 48 taken along line 49-49 thereof in the opposite direction of FIG. 49;

FIG. 55 is a perspective view of the pivot member of the dynamized or standard bone plate systems of FIG. 37, 45, or 44;

FIG. 56 is a side view of the pivot member of the dynamized or standard bone plate systems of FIG. 37, 45, or 44

FIG. 57 is an exploded perspective view of the bone screw and corresponding locking member of the dynamized or standard bone plate systems of FIG. 37, 45, or 44;

FIG. 58 is a cross-sectional side view of the bone screw and locking member of FIG. 57 with the locking member proud;

FIG. 59 is a cross-sectional side view of the bone screw and locking member of FIG. 57 with the locking member seated;

FIG. 60 is an exploded perspective view of the dynamized bone plate system of FIG. 36 with rescue screws and corresponding locking members in lieu of the bone screws and locking members of FIG. 57;

FIG. 61 is a perspective view of the rescue screw and corresponding locking member of FIG. 60;

FIG. 78 is a perspective view of a bone anchor driver including features in accordance with another aspect of the present invention and configured to drive the bone screw of FIG. 22;

FIG. 79 is a close-up perspective view of a portion of the driver of FIG. 78;

FIG. 80 is a close-up exploded perspective view of a portion of the driver of FIG. 78;

FIG. 81 is a close-up cross-sectional side view of a portion of the driver of FIG. 78;

FIG. 82 is a cross-sectional side view of the driver of FIG. 78;

FIG. 83 is a perspective view of a guided sleeve including features in accordance with another aspect of the present invention;

FIG. 84 is a side view of the guided sleeve of FIG. 83;

FIG. 85 is a cross-sectional side view of the guided sleeve of FIG. 83;

FIG. 86 is a cross-sectional side view of the guided sleeve of FIG. 83 with the bias member compressed;

FIG. 87 is an exploded perspective view of the guided sleeve of FIG. 83;

FIG. 88 is a perspective view of the base member of the guided sleeve of FIG. 83;

FIG. 89 is a perspective view of the base member of the guided sleeve of FIG. 83;

FIG. 90 is a cross-sectional side view of the guided sleeve of FIG. 83 engaged with a bone anchor insertion site preparation tool including features in accordance with another aspect of the present invention;

FIG. 91 is a side view of the preparation tool of FIG. 90;

FIG. 92 is an exploded side view of the preparation tool of FIG. 91;

FIG. 93 is a shaft of the preparation tool of FIG. 91 wherein the tip portion is an awl;

FIG. 94 is a shaft of the preparation tool of FIG. 91 wherein the tip portion is a drill;

FIG. 95 is a shaft of the preparation tool of FIG. 91 wherein the tip portion is a tap;

FIG. 98 is an exploded side view of the guide of FIG. 96;

FIG. 99 is a close-up perspective view of a portion of the guide of FIG. 96;

FIG. 100 is a cross-sectional side view of a portion of the guide of FIG. 96;

FIG. 103 is a top plan view of a portion of the guide of FIG. 96 engaged with the pivot base of the dynamized bone plate system of FIG. 45;

FIG. 104 is a close-up cross-sectional side view of a portion of the guide of FIG. 96 engaged with the pivot base of the dynamized bone plate system of FIG. 45;

FIG. 105 is a cross-sectional side view of a portion of the guide of FIG. 96 engaged with the pivot base of the bone plate of the dynamized bone plate system of FIG. 45;

FIG. 108 is a perspective view of the driver of FIG. 106;

FIG. 109 is an exploded perspective view of the driver and of FIG. 108 and the bone screw and locking member of FIG. 58;

FIG. 110 is a close-up perspective view of a portion of the driver of FIG. 108;

FIG. 111 is a close-up perspective view of the portion of FIG. 110 with the insert exploded;

FIG. 112 is the insert of FIG. 111 aligned with the bone screw and locking member of FIG. 58.

FIG. 120 is a perspective view of a locking guide in an unlocked configuration, including features in accordance with another aspect of the present invention;

FIG. 121 is a perspective view of the locking guide of FIG. 120 in a locked configuration;

FIG. 122 is an exploded perspective view of the locking guide of FIG. 120;

FIG. 123 is a close-up perspective view of a portion of the locking guide of FIG. 120;

FIG. 124 is a cross-sectional side view of a portion of the locking guide of FIG. 120;

FIG. 125 is a perspective view of the coupling member of the locking guide of FIG. 120;

FIG. 126 is a top plan view of a portion of the locking guide of FIG. 120 engaged with the bone plate system of FIG. 39;

FIG. 127 is a close-up cross-sectional side view of a portion of the locking guide of FIG. 120 engaged with a pivot base of the bone plate system of FIG. 39;

FIG. 128 is a close-up perspective view of a portion of the locking guide of FIG. 120 engaged with a pivot base of the bone plate system of FIG. 39;

FIG. 129 is a perspective view of a bone pin configured to temporarily hold the bone plate system of FIG. 39 in a desired position, including features in accordance with another aspect of the present invention;

FIG. 130 is a perspective view of the bone pin of FIG. 129 engaged with the bone plate system of FIG. 39;

FIG. 131 is a perspective view of a bone pin instrument, the bone pin of FIG. 129, and the bone plate system of FIG. 39.

DETAILED DESCRIPTION OF THE PREFERRED EMBODIMENTS

Figure 36:
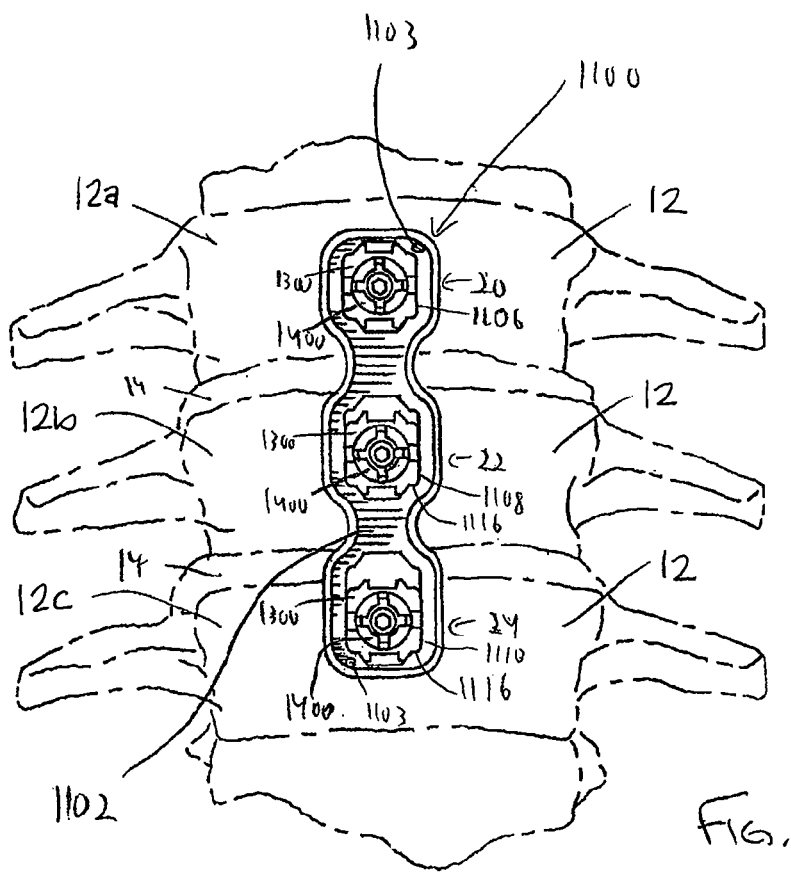
FIG. 36 is a plan view of a dynamized bone plate system including features in accordance with the present invention and securing vertebrae in a particular orientation.
Figure 37:
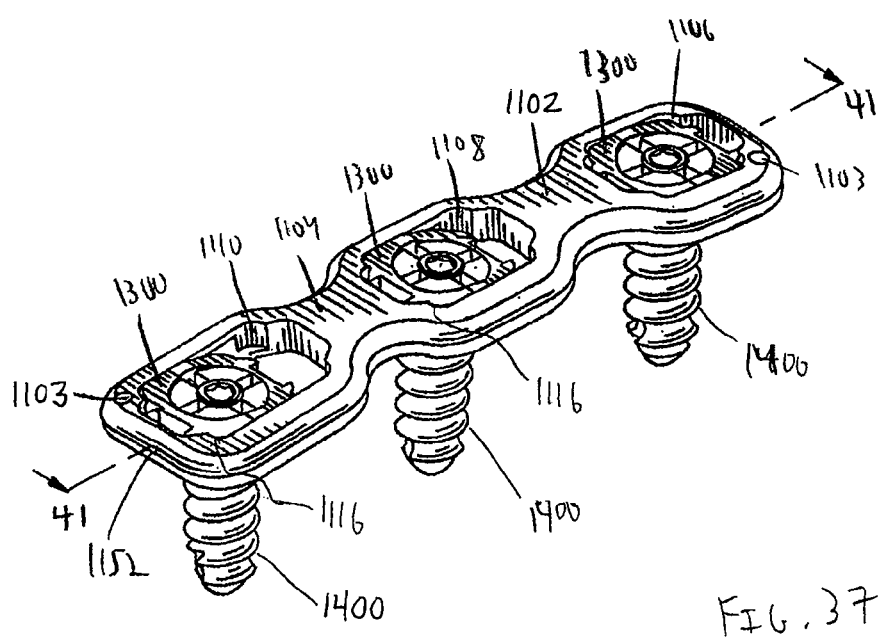
FIG. 37 is a perspective view of the dynamized bone plate system of FIG. 36.

Generally speaking, pursuant to these various embodiments, bone plate systems are disclosed herein for securing a plurality of bones 12 in a desired orientation and arrangement. In some forms, the bone plate system utilizes a dynamized plate with dynamic bores so that bones may compress and shift toward each other, such as with dynamic or dynamized bone plate systems 100, 1100, 1700 shown in FIGS. 1, 36, and 45, respectively. In other forms, bone plate systems utilize standard plate members with throughbores of the same size, such as standard bone plate systems 200, 1200 shown in FIGS. 7, 43.

Figure 1:
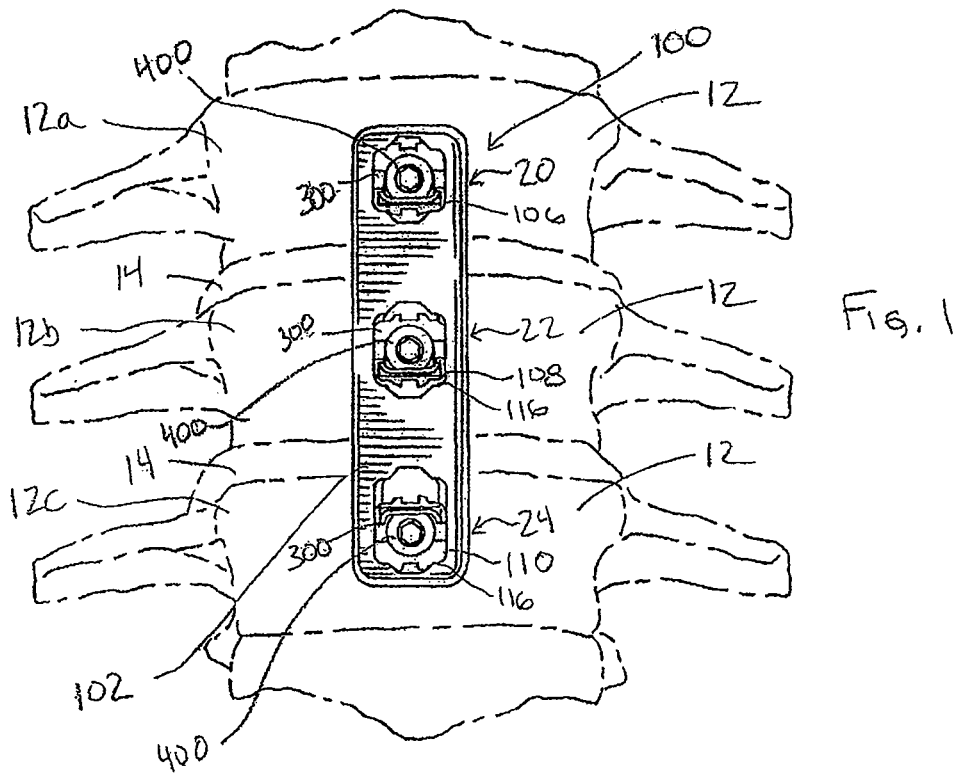
FIG. 1 is a plan view of a dynamized bone plate system including features in accordance with the present invention and securing vertebrae in a particular orientation.
Figure 2:
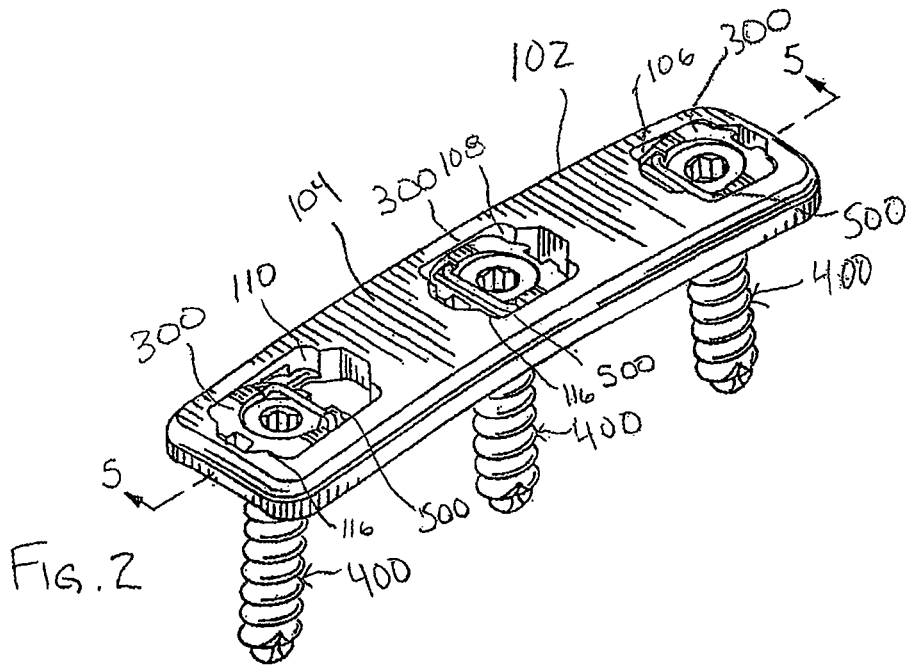
FIG. 2 is a perspective view of the dynamized bone plate system of FIG. 1.

Referring now to the figures, and in particular to FIGS. 1-6, a dynamized bone plate system 100 is shown. Referring to FIG. 1, the dynamized bone plate system 100 assists in the healing and repair of damaged, fractured, or broken bones. In the exemplary illustration of FIG. 1, bones 12 are adjacently located vertebrae of a spine, each spaced by a spinal disc 14. The bone plate system 100 may also be used to assist in the healing necessary after trauma has been experienced by the spinal disc 14. For example, the bone plate system 100 may be utilized for stabilization and securement when adjacent vertebrae 12 are fused, with or without the assistance of a bone graft between the vertebrae 12. Furthermore, the bone plate system 100 may be used to correct and/or relieve symptoms of a variety of spinal disorders, which may include but are not limited to degenerative disorders, disorders induced by trauma, and pinched nerves.

In each of these examples, the bone plate system 100 is used to secure the bones 12 (and any prosthetic or graft) in a desired spatial relationship. Typically, the desired spatial relationship between the bones 12 (vertebrae) is generally vertical, such as the vertebrae 12 would be in a normal, healthy spine when the person is standing. As discussed above, compression or loading of bones promotes healing of the bones or bone fragments and improves the integrity of the fusion therebetween. Particular to some bones in the human anatomy, such as a femur, the weight of the person, due to gravity, compresses those bones. For spines, the fusion of adjacent vertebrae can similarly benefit from using gravity to compress the adjacent vertebrae.

Accordingly, though the bones 12 are secured in a desired spatial relationship, the dynamized bone plate system 100 preferably allows the bones 12 to shift relative to each other. In other words, to capitalize on the compression imparted to the adjacent vertebrae 12 by gravity, the bone plate system 100 is designed to allow the bones 12 to compress in a manner dictated by the bone plate system 100.

The bone plate system 100 generally includes a bone plate member 102 secured to the bones 12 with bone anchors that are, in a preferred form, bone screws 400. The bone plate 102 includes throughbores 106, 108, 110 formed in the plate 102 with a generally rectangular pivot base 300 secured within each throughbore 106, 108, 110. The bone screws 400 are secured in the generally rectangular pivot base 300 by retaining members 500.

The bone plate 102 may be provided with curvature in the longitudinal direction that conforms the plate member 102 to the average natural curvature of the spine, as well as to reduce interference with surrounding tissues. The plate 102 is preferably pre-bent to have a curvature in a longitudinal direction, more preferably with a radius of curvature of approximately 200 millimeters, and in a lateral direction, more preferably with a radius of curvature of approximately 20 millimeters. It is often desirable to alter the standard shape of the plate 102 to fit an individual patient's unique anatomy. This should be done in a manner so as not to scratch or mar the surfaces of the bone plate 102, which otherwise may negatively affect the long-term fatigue performance of the bone plate 102. For this purpose, a plate bending instrument may be used for altering the curvature of the plate 102 when necessary due to a unique anatomy. The plate bender is operated to either increase or decrease the radius of the lordotic curvature of the plate 102.

The plate 102 is generally rectangular, although other configurations are possible. For example, the bone plate 102 may have indentations formed along the sides thereof between each throughbore. By another approach, the bone plate 102 may also have apertures therethrough in the areas between the bores to aid bone graft visualization. The bone plate 102 includes a pair of generally parallel longitudinal side wall portions 150 and a pair of generally parallel end wall portions 152 and a top face 104 and a bottom face 114. The bone plate 102 preferably has a throughbore 106, 108, or 110 located at each level at which a bone 12 is to be secured thereto to thereby define tiers 20, 22 24 of the bone plate 102. As depicted in FIG. 1, the plate 102 has an uppermost tier 20, an intermediary tier 22, and a lowermost tier 24, each respectively in general proximity to an uppermost vertebrae 12a, an intermediary vertebrae 12b, and a lowermost vertebrae 12c, where the plate 102 is utilized for securing the three vertebrae 12a, 12b, 12c in a spatial relationship. Although depicted as three tiers 20, 22, 24, any number of tiers could be provided for securing a plurality of bones, bone segments, or implanted materials. A single throughbore 106, 108, 110 is formed in the plate 102 at each tier 20, 22, 24. As a result of the single bore per tier configuration, the plate 102 may have a minimized width profile, thereby reducing the encroachment and irritation to the esophagus and other soft tissues, the occurrence of esophageal dysphagia, as well as the required size of the access surgical opening required for insertion and mounting of the plate 102. The narrow width of the plate 102 further provides for improved visualization of the surrounding disc space. In contrast to bone plate systems having two bores at each tier, the single-bore configuration requires half as many bone anchors, thereby reducing patient exposure, time required to complete the surgical procedure, and overall production costs. For a plate 102 having two to three tiers, the preferred length of the plate 102 is generally 12 to 40 millimeters.

In order to permit the above-described compressive shifting of the bones 12 due to gravity, the plate 102 is a dynamized or dynamic plate. In the presently depicted embodiment, the plate 102 allows the bones 12 to compress towards each other by allowing the pivot base 300 and the bone screw 400 secured therein to shift relative to the plate 102 in a manner defined by the plate 102. To enable this compression, at least some of the throughbores 108, 110 are dynamized, meaning they are elongate with respect to the longitudinal direction of the plate 102.

In the embodiment illustrated in FIGS. 1-6, the throughbores 108, 110 of the intermediary tier 22 and lowermost tier 24 are dynamized throughbores, while the throughbore 106 of the uppermost tier 20 is non-dynamized such that the non-dynamized throughbore 106 permits either no or minimal translation of the pivot base 300 and the bone screw 400 secured therein relative to the bone plate 102. In this manner, the intermediary vertebrae 12b secured by the bone screw 400 through the dynamized throughbore 108 of the intermediary tier 22 and the lowermost vertebrae 12c secured by the bone screw 400 through the dynamized throughbore 110 of the lowermost tier 24 may translate toward the uppermost vertebrae 12a secured by the non-dynamized throughbore 106 of the uppermost tier 20 as the vertebrae 12 compress.

The length of the dynamized throughbores 108, 110 depends on the amount of translational desired subsidence at each tier. As shown, the throughbore 110 of the lowermost tier 24 is longer than the throughbore 108 of the intermediary tier 22. As a result, the pivot base 300 secured in the throughbore 110 of the lowermost tier 24 may translate a greater distance than the pivot base 300 secured in the throughbore 108 of the intermediary tier 22, with the throughbore 110 of the lowermost tier 24 allowing for approximately 2.50 millimeters of translation and the throughbore 108 of the intermediary tier 22 allowing for approximately 1.25 millimeters of translation. As shown in FIG. 1, the pivot base 300 of the intermediary and lowermost tiers 22, 24 is preferably initially placed in the lower end 116 of the dynamized throughbores 108, 110 at the furthest point away from the non-dynamized throughbore 106. The placement of the pivot base 300 in the lower end 116 of the throughbores 108, 110 allows for maximum translation of the pivot base 300 and the bone screw 400 secured therein as the vertebrae 12a, 12b, 12c compress. The throughbore 110 of the lowermost tier 24 may translate to accommodate the translational movement of the pivot base 300 within the throughbore 108 of the intermediary tier 22 caused by compression between the uppermost vertebrae 12 and the intermediary vertebrae 12b and then may also further translate to allow for further compression between the intermediary vertebrae 12b and the lowermost vertebrae 12c.

It should be noted that the plate 102 may be equipped with two or more tiers, with each tier having non-dynamized throughbores, or each tier having dynamized throughbores, or any combination thereof, as desired. In addition, the length and location of each dynamized throughbore may also be varied. As one illustrative example, the throughbore 108 of the intermediary tier 22 may be non-dynamized, while the throughbores 106, 110 of the uppermost tier 20 and lowermost tier 24 may be dynamized, with each dynamized throughbore having an equal length to allow for equal translation of the pivot base 300 within the throughbore toward the non-dynamized throughbore 108.

Figure 14:
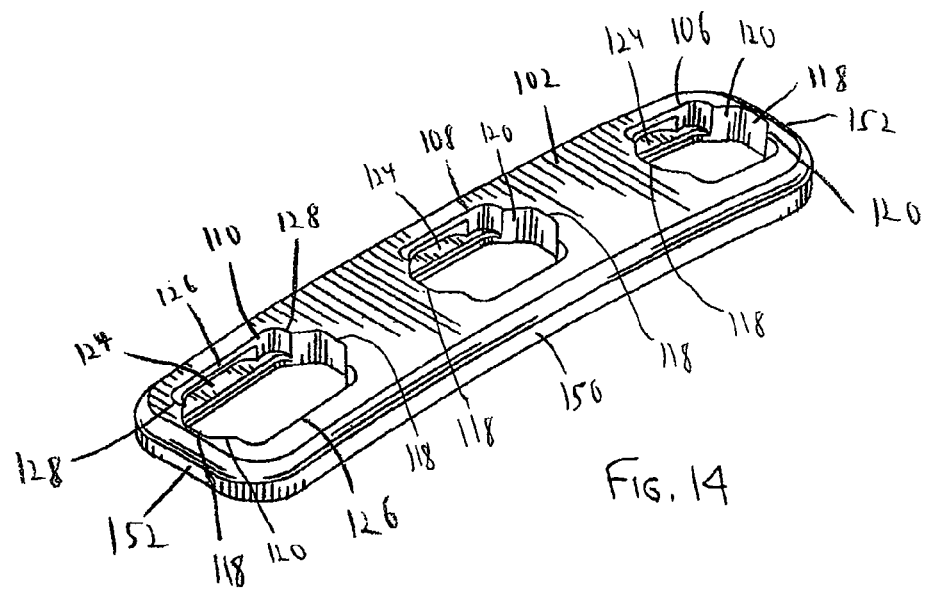
FIG. 14 is a perspective view of the bone plate of the dynamized bone plate system of FIG. 2.
Figure 15:
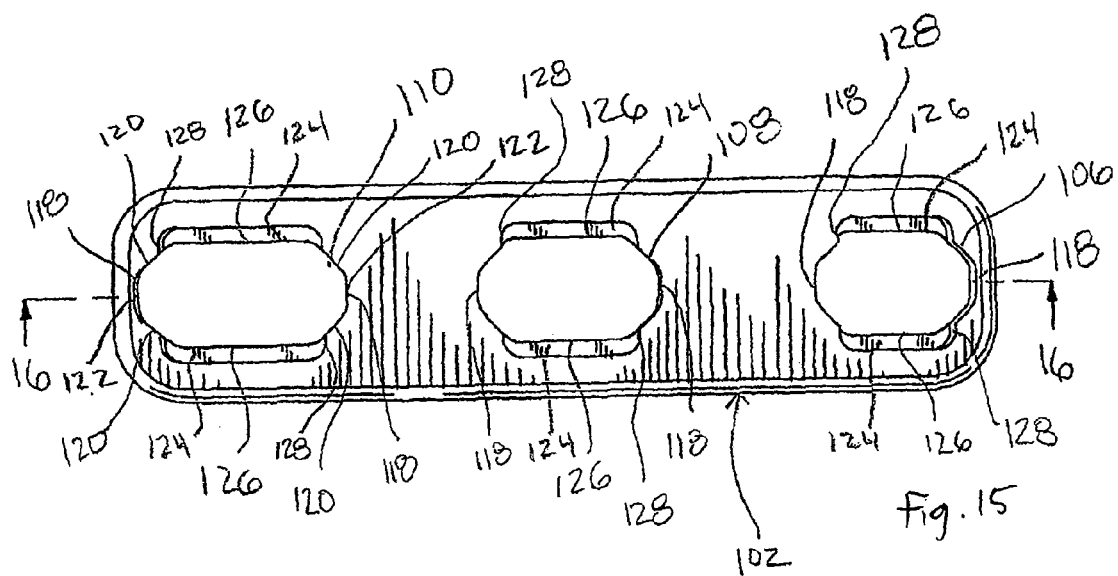
FIG. 15 is a top plan view of the bone plate of FIG. 14.
Figure 16:
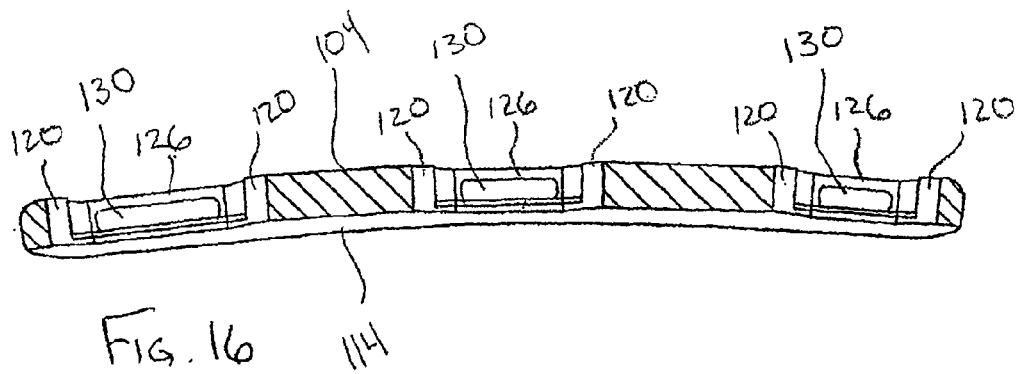
FIG. 16 is a cross-sectional side view of the bone plate of FIG. 15 taken along line 16-16 thereof.
Figure 17:
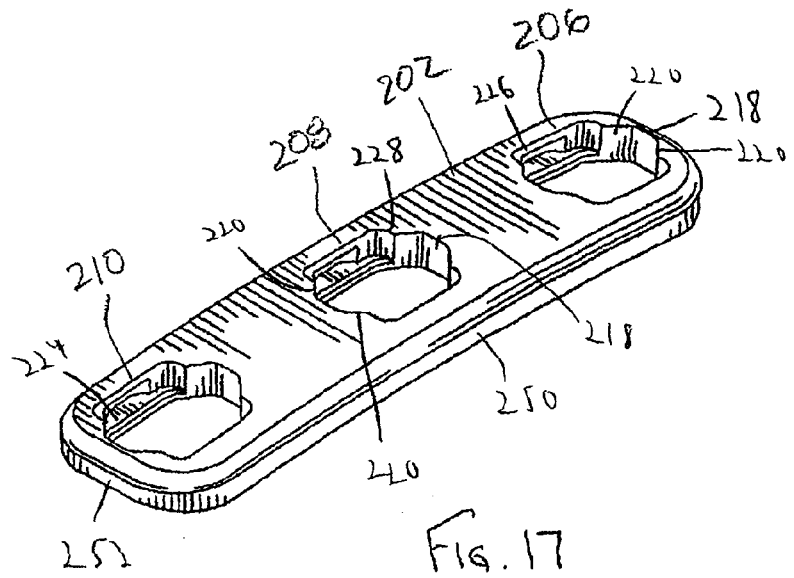
FIG. 17 is a perspective view of the bone plate of the standard bone plate system of FIG. 8.
Figure 18:
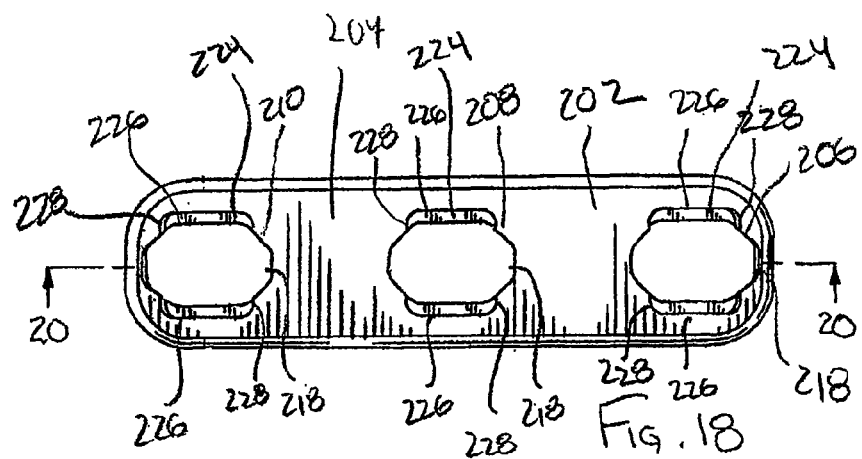
FIG. 18 is a top plan view of the standard bone plate of FIG. 17.
Figure 19:
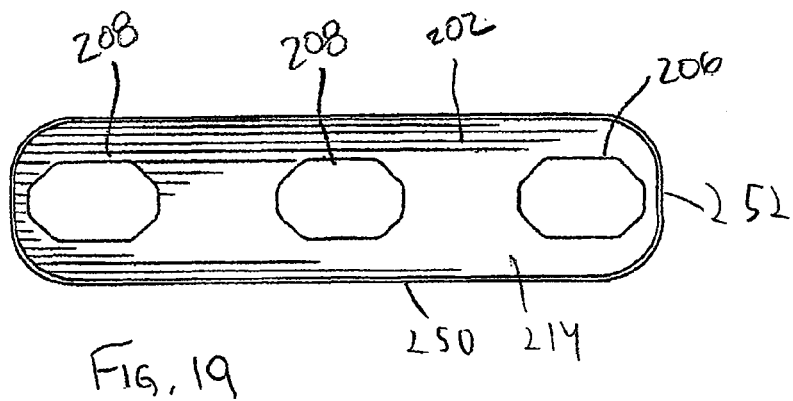
FIG. 19 is a bottom plan view of the standard bone plate of FIG. 17.
Figure 20:
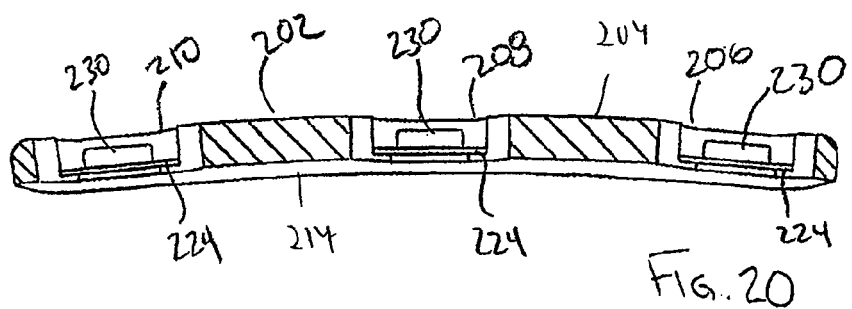
FIG. 20 is a cross-sectional side view of the standard bone plate of FIG. 18 taken along line 20-20 thereof.

As shown in FIGS. 14-16, each throughbore 106, 108, 110 has a generally rectangular profile comprised of a pair of longitudinal side wall portions 126 and a pair of end wall portions 128. The pair of longitudinal side wall portions 126 of each throughbore 106, 108, 110, in conjunction with slot portions 130 described below, vary in length depending on the amount of translational movement allowed for each throughbore 106, 108, 110. In the illustrated embodiment, the throughbore 110 associated with the lowermost tier 24 has the longest longitudinal side wall portions 126 to allow for the approximately 2.50 millimeters of translational movement of the pivot base 300. The throughbore 108 associated with the intermediary tier 22 has slightly shorter longitudinal side wall portions 126 to allow for the approximately 1.25 millimeters of translational movement of the pivot base 300. The throughbore 106 associated with the uppermost tier 20 has longitudinal side wall portions 126 sized to accommodate the pivot base 300 while allowing for no or minimal translational movement. The pair of end wall portions 128 are the same size for each throughbore 106, 108, 110 and are generally sized to accommodate the width of the pivot base 300 with little clearance. In addition, relief areas 118 extend from the end wall portions 128 to allow for instrument clearance. The relief areas 118 create space in which an instrument may be inserted to engage the plate 102 and/or pivot base 300 within each throughbore 106, 108, 110. The relief areas 118 are generally comprised of a pair of angled walls 120 extending to an end wall 122, although other relief area geometry is contemplated to accommodate tools of different shapes or configurations.

Each throughbore 106, 108, 110 has a floor portion 124 extending along each longitudinal side wall portion 126 along the lower face 114 of the bone plate 102. The floor portions 124 extend into the throughbore 106, 108, 110 to narrow a portion of the throughbore 106, 108, 110. As a result, the floor portions 124 support bottom portions of the pivot base 300, as described below. In addition, the floor portions 124 support pivot members or pins 600 extending from the pivot base 300, with the pivot members 600 sliding along the floor portions 124 to allow for the translational movement of the pivot base 300. The floor portions 124 and the configuration of the pivot base 300 also limit the pivotal movement of the pivot base 300, as described below.

Cavities, which, in a preferred form are slot portions or elongated grooves 130 are formed in the side wall portions 126 just above the intersection of the floor portion 124 and the longitudinal side wall portion 126. The slot portions 130 allow the pivot pins 600 extending from each side of the pivot base 300 to be received in the longitudinal side wall portions 126 of each throughbore 106, 108, 110. The slot portions 130 are sized in length to accommodate the desired translational movement of each pivot base 300 within the throughbores 106, 108, 110. In the illustrated embodiment, the throughbore 110 associated with the lowermost tier 24 has the longest slot portions 130 to allow for the 2.50 millimeters of translational movement of the pivot base 300. The throughbore 108 associated with the intermediary tier 22 has slightly shorter slot portions 130 to allow for the 1.25 millimeters of translational movement of the pivot base 300. The throughbore 106 associated with the uppermost tier 20 has slot portions 130 sized to accommodate the pivot base 300 while allowing for no or minimal translational movement. The slot portions 130 are generally sized in height and depth to accommodate the pivot pins 600 therein.

Referring now to FIGS. 31-35, the pivot base 300 is shown. The pivot base 300 is generally rectangular, having longitudinal side wall portions 302 that generally align with the longitudinal side wall portions 126 of the throughbore 106, 108, 110 when the pivot base 300 is placed therein. The generally rectangular configuration of the pivot base 300 resists torsion by increasing the torsional strength and stability of the pivot base 300 and the plate 102. The pivot base 300 further includes end wall portions 304 having a pair of forked projections 306 extending therefrom. The forked projections 306 allow for instrument engagement and, in conjunction with the relief areas 118 of the plate 102, facilitate engagement of the plate 102 and/or the pivot base 300 within each throughbore 106, 108, 110. By one approach, the instrument may grasp the pivot base 300 by inserting the instrument in a space 308 between the pair of forked projections 306. Although the pivot base 300 includes forked projections 306, other end wall geometry is contemplated to accommodate instruments or tools of different shapes or configurations.

Figure 35:
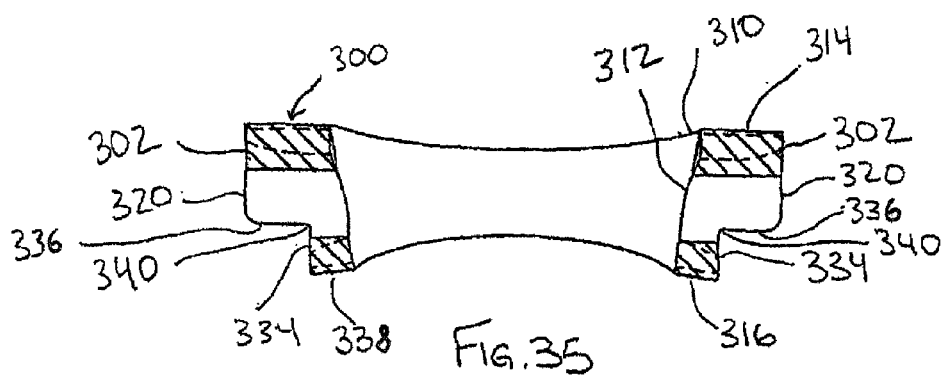
FIG. 35 is a cross-sectional side view of the pivot base of FIG. 32 taken along line 35-35 thereof.

The pivot base 300 has a generally centrally located opening 310 extending therethrough to accommodate the bone screw 400 to be inserted therein. The opening 310 is sized to accommodate the diameter of the bone screw 400 secured therein. As shown in FIG. 35, the opening 310 has tapered side walls 312 around the diameter thereof which mates with the tapered head portion 404 of the bone screw 400, as described below. The mating tapers of the opening side walls 312 and the screw head portion 404 assist in securing the bone screw 400 in place within the pivot base 300 and further limits the ability of the bone screw 400 to back out of the plate 102.

Figure 34:
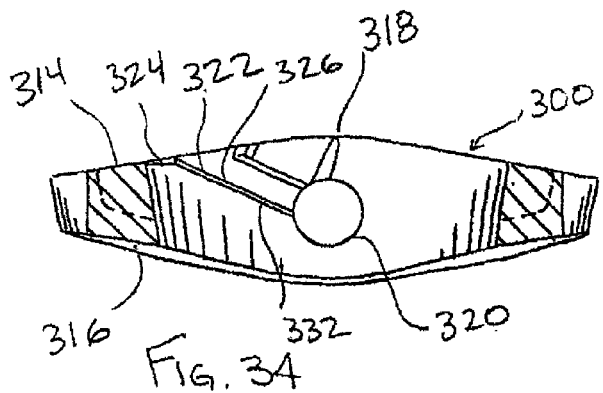
FIG. 34 is a cross-sectional side view of the pivot base of FIG. 32 taken along line 34-34 thereof.

The side wall portions 302 and end wall portions 304 define a top face 314 and a bottom face 316 of the pivot base 300, with the top face 314 of the pivot base 300 generally aligned with the top face 104 of the bone plate 102 when the pivot base 300 is secured within the respective throughbore thereof. The upper face 314 and the bottom face 316 of the pivot base 300 have a generally convex shape, as shown in FIG. 34. As a result, the pivot base 300 has a thicker center portion 318 and narrows toward the end wall portions 304. Each longitudinal side wall portion 302 of the pivot base 300 includes an aperture 320 therethrough to accommodate the pivot pins 600, with the apertures 320 extending through from the longitudinal side wall portions 302 to the opening 310. The apertures 320 of each longitudinal side wall portion 302 are generally aligned with one another on either side of the pivot base 300. The apertures 320 are generally cylindrical and sized to receive the pivot pins 600. The anchor pin apertures 320 are positioned generally centrally along the longitudinal side wall portions 302 within the thicker center portion 318 of the side wall portion 302. With respect to the center opening 310, the aperture 320 is spaced equidistant from both end wall portions 304 and from the top 314 and bottom face 316 of the pivot base 300.

The top face 314 of the pivot base 300 further includes a ramp portion 322 extending from one end wall portion 304 and down toward the anchor pin apertures 320. The ramp portion 322 includes a shallow initial ramp portion 324 adjacent the end wall 304 and then a deeper angled lower ramp portion 326 that extends from the initial ramp portion 324 and down to the apertures 320. The ramp portion 322 generally functions to accommodate the retaining member 500, as will be discussed below. Upper edge portions 328 of the ramp portion 322 are exposed by cutouts 330 in the top face 314 of the pivot base 300, while lower edge portions 332 of the ramp portion 322 extend below the top face 314 of the pivot base 300 and are concealed by the top face 314 of the pivot base 300, with the top face 314 of the pivot base 300 extending over the lower edge portions 332 of the ramp portions further securing the retaining member or clip 500 in place.

Figure 21:
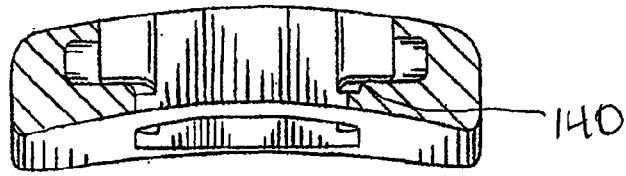
FIG. 21 is a cross-sectional end view of the dynamized or standard bone plates of the standard or dynamic bone plate systems of FIG. 2 or 8.
Figure 33:
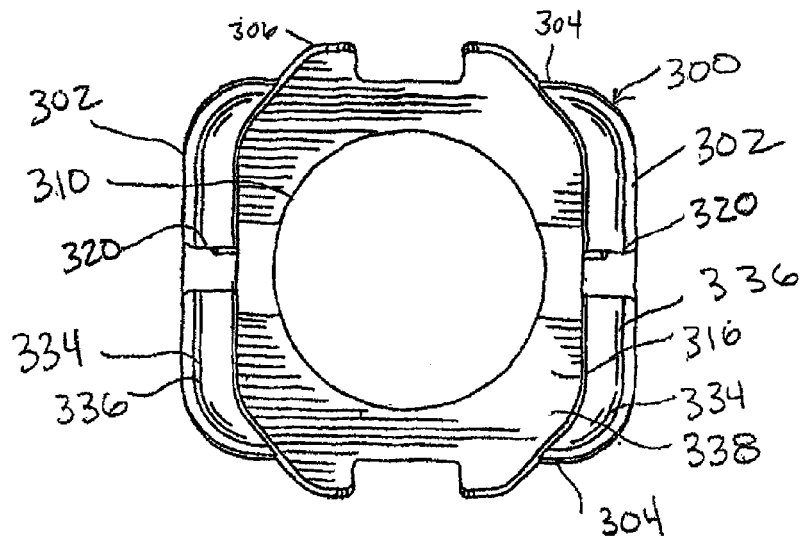
FIG. 33 is a bottom plan view of the pivot base of FIG. 31.

The bottom face 316 of the pivot base 300, as shown in FIG. 33, has longitudinal recessed portions 334 adjacent the longitudinal side wall portions 302 of the pivot base 300 to create a two-tiered bottom face comprised of an upper level bottom face 336 adjacent the longitudinal side wall portions 302 and a lower level bottom face 338 on the remainder of the bottom face 316. The recessed portions 334 provide a notched profile 340, as shown in FIG. 35, adjacent the longitudinal side walls 302. The notched profile 340 of the pivot base 300 generally aligns with the notched profile 140 of the bone plate 102, as shown in FIG. 21, as formed by the longitudinal side wall portions 126 of the throughbore 106, 108, 110 and the floor portions 124 extending therefrom. As a result, the pivot base 300 sits into the throughbore 106, 108, 110 of the bone plate 102, with the recessed portions 334 being generally aligned with and generally supported by the floor portions 124 of the throughbores 106, 108, 110, and the lower level bottom face 338 seated into the narrowed hole portion of the throughbore 106, 108, 110 formed by the floor portions 124. The pivot base 300 is dropped into each throughbore 106, 108, 110, with the longitudinal side walls 302 of the pivot base 300 generally aligned with and confronting the longitudinal side walls 126 of the throughbore 106, 108, 110 with a minimal amount of clearance between the side walls 302, 126 to allow for relative translational movement of the pivot base 300 within the throughbore 106, 108, 110. The generally rectangular profile of the pivot base 300 mates with the equivalent generally rectangular profile of the throughbores 106, 108, 110 in the plate 102. The mating profiles of the pivot base 300 and the throughbores 106, 108, 110 limit the rotational translation between the pivot base 300 and the plate 102, resulting in increased torsional plate strength.

Figure 25:
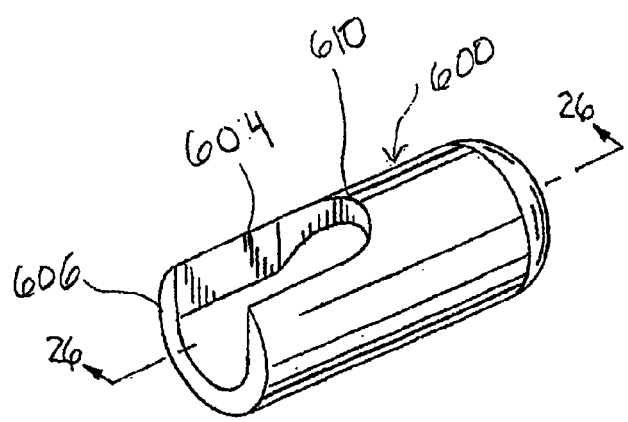
FIG. 25 is a perspective view of the pivot member of the dynamized or standard bone plate systems of FIG. 2 or 8.
Figure 26:
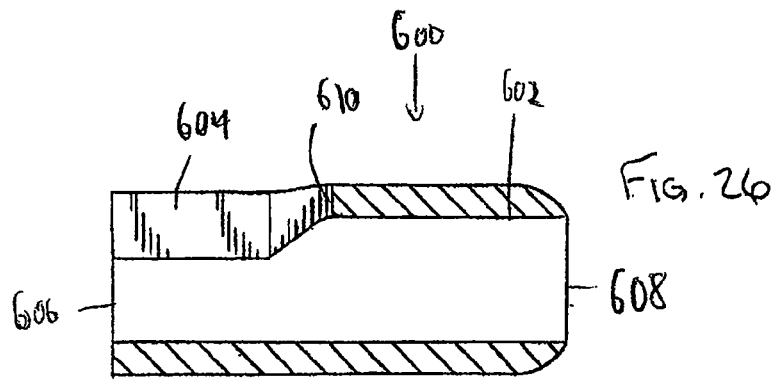
FIG. 26 is a cross-sectional side view of the pivot pin of FIG. 25 taken along line 26-26 thereof.
Figure 27:
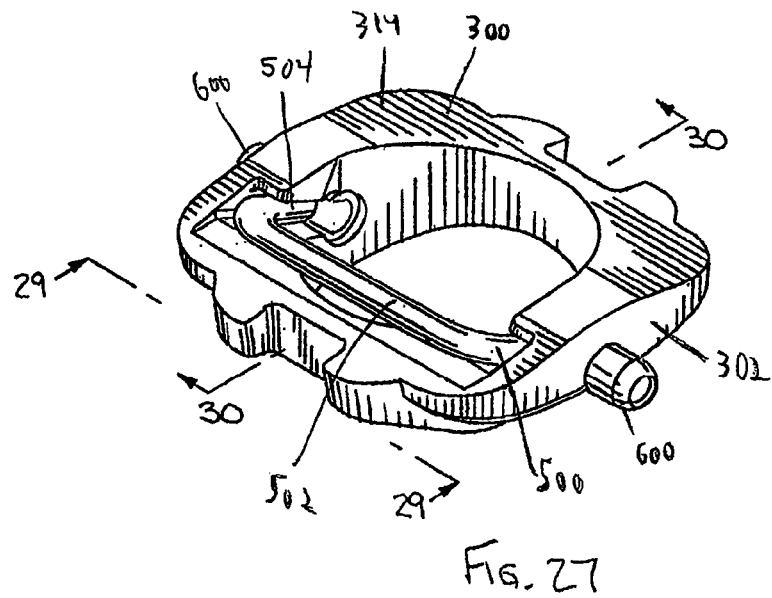
FIG. 27 is a perspective view of the pivot base assembly of the dynamized or standard bone plate systems of FIG. 2 or 8.
Figure 28:
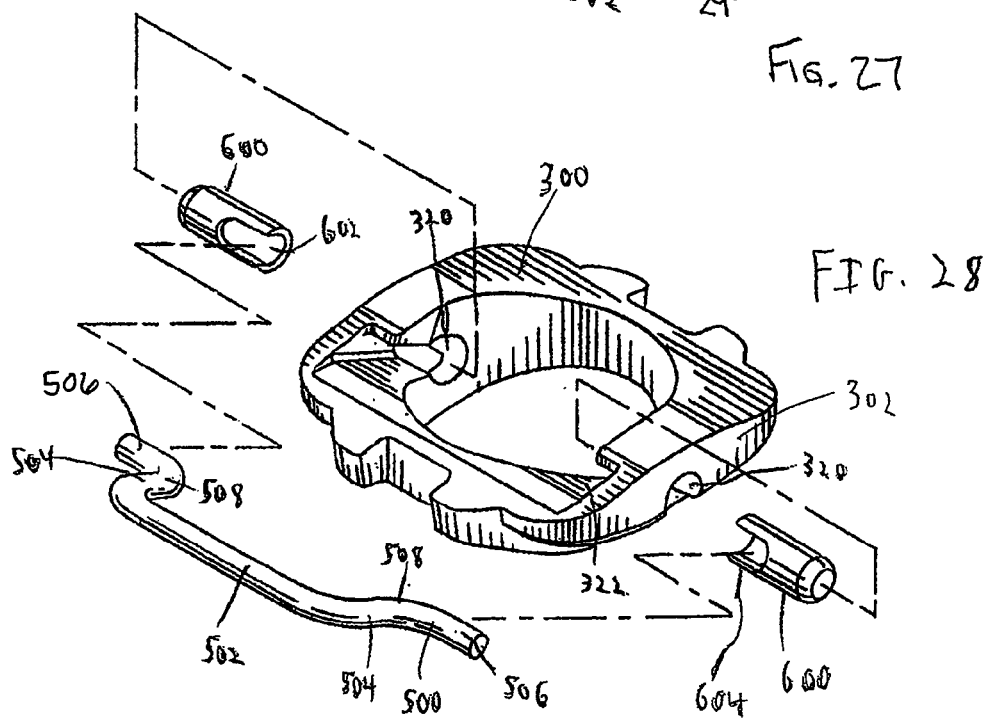
FIG. 28 is an exploded perspective view of the pivot base assembly of FIG. 27.
Figure 29:
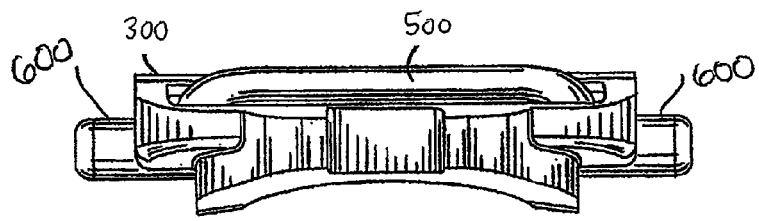
FIG. 29 is an end view of the pivot base assembly of FIG. 27 taken along line 29-29 thereof.
Figure 30:
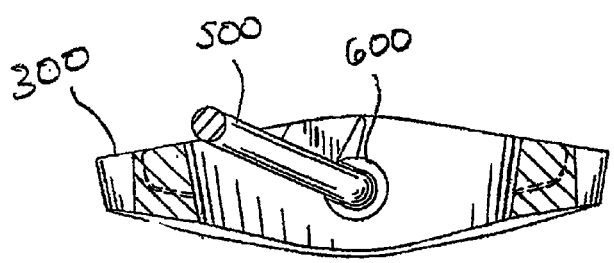
FIG. 30 is a cross-sectional side view of the pivot base assembly of FIG. 27 taken along line 30-30 thereof.
Figure 31:
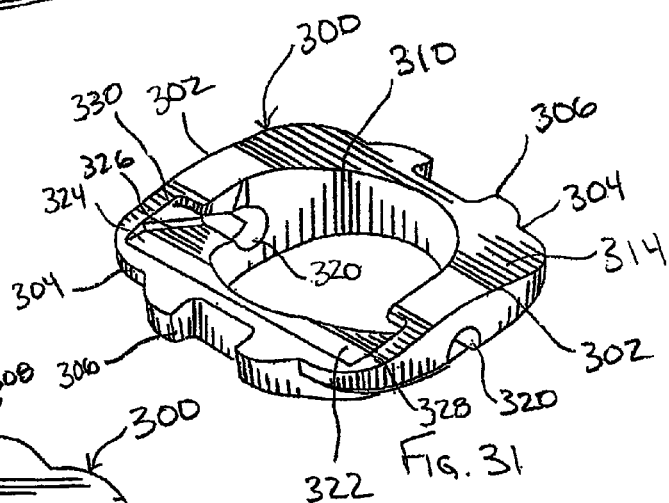
FIG. 31 is a perspective view of the pivot base of the pivot base assembly of the dynamized or standard bone plate systems of FIG. 2 or 8.
Figure 32:
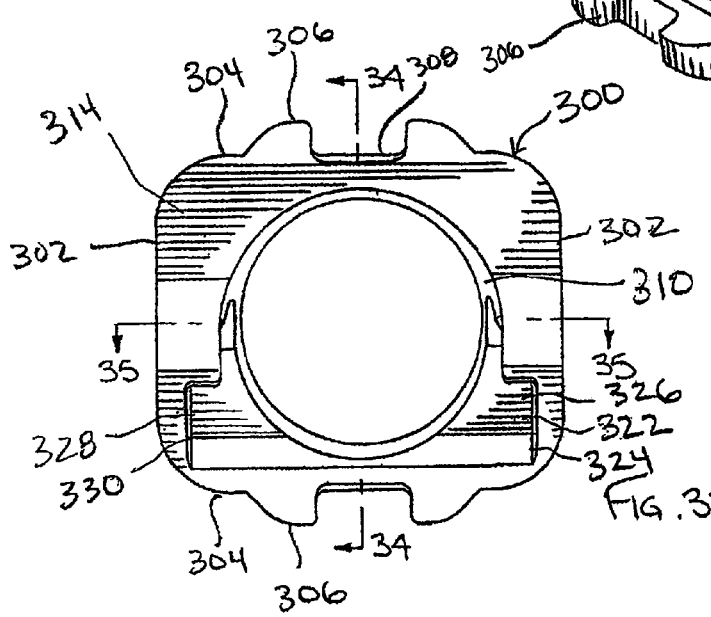
FIG. 32 is a top plan view of the pivot base of FIG. 31.

Referring now to FIGS. 25-26, the pivot member or pin 600 is shown. The pivot pin 600 has a generally cylindrical profile with a through hole 602 formed therein. In addition, a slot 604 is formed in the pin 600 and extends from a first end 606 thereof to approximately halfway down the length of the pin 600 to accommodate the retaining member 500 therein. A second end 608 of the pin 600 may optionally be tapered or rounded to provide for better mating of the pin 600 in the slot 130 of the bone plate 102. As shown in FIGS. 27 and 28, the pins 600 are inserted into the apertures 320 in the pivot base 300 after the pivot base 300 has been deposited in the throughbores 106, 108, 110 of the bone plate 102. The pins 600 are oriented with the slot 604 generally facing the ramp portion 322 of the pivot base 300 so that the slot 604 may receive a portion of the retaining member 500 therein. The pins 600 are inserted in the apertures 320 of the pivot base 300 such that a portion of the pin 600 extends beyond the longitudinal side wall portions 302 of the pivot base 300 and into the slot portion 130 of the throughbore 106, 108, 110 of the bone plate 102. The pins 600 can move along the length of the slot 130 to allow for the translational movement of the pivot base 300 within the dynamized throughbores 108, 110. In addition, the pivot pins 600 limit any pivot action of the pivot base 300 relative to the plate 102 about the lateral axis of the plate 102. The pivot pins 600 allow the pivot base 300 to toggle or pivot relative to the plate 102 in the direction of the longitudinal axis of the plate 102, with the pivot angle being generally defined by the geometry of the plate 102 and the pivot base 300. Specifically, the floor portions 124 of each throughbore 106, 108, 110 of the bone plate 102 limit the pivot angle of the pivot base 300 because the upper level bottom face 336 of the pivot base 300 contacts the floor portions 124 as the pivot base 300 pivots to thereby limit the pivot angle. The predetermined range through which the pivot base 300 may toggle may be, for example, plus or minus ten degrees relative to the plate 102. Once the pivot pins 600 are placed within the pivot base 300 and inserted into the slot portions 130 of the bone plate 102, the retaining member 500 may be positioned in place. FIGS. 1-13 show the pivot bases 300 oriented in one of two directions such that the retaining members 500 may project in a direction that is either generally up or generally down with respect to the longitudinal axis of the spine. The pivot bases 300 may be installed in either direction with no degradation of performance, and it will be appreciated that other combinations of pivot base orientations other than those shown would, of course, be possible.

The retaining member, shown in FIG. 28, 500 has a generally U-shaped profile comprised of a generally straight center portion 502 and a pair of prongs 504 extending generally transversely to the center portion 502. In addition, a leg portion 506 extends generally transverse to each of the prongs 504, with the leg portions 506 configured to be secured at least partially within the pivot pins 600. The retaining member 500 is preferably made of a resilient material to allow for flexing and bending of the retaining member 500 during the insertion, removal, and/or surgical operation. The retaining member 500 is elastically resilient so that the distal ends may be compressed and return to their natural shape when released, and so that the retaining member 500 may expand and contract as the screw head 404 passes through and beyond the retaining member 500, as described below. The retaining member 500 generally functions to secure the pivot members 600 in place, thus mounting the pivot base 300 in place within a corresponding throughbore 106, 108, 110 of the plate 102. The retaining member 500 further functions to retain the bone screw 400 in place to limit the ability of the bone screw 400 to back out of the plate 102.

To insert the retaining member 500 into the pins 600 secured in the pivot base 300, the retaining member 500 is generally aligned with the ramp portion 322 of the pivot base 300, with the prongs 504 and the leg portions 506 of the retaining member 500 extending toward the ramp portion 322. The pair of prongs 504 may be compressed toward each other to reduce the width of the distal end of the retaining member 500 to allow for the legs 506 to clear the longitudinal side wall portions 302 of the pivot base 300 and slide down the ramp portion 322. When the legs 506 are generally aligned with the pivot base apertures 320 and the pins 600 secured therein, the retaining member 500 is released from the compressed position and allowed to expand at least partially such that the legs 506 extend into the center through holes 602 of the pivot members or pins 600. The legs 506 extend into the through holes 602, while the prongs 504 seat flush against the ramp portion 322, with the top face 314 of the pivot base 300 extending over a portion of the prongs 504 to maintain the retaining member 500 in place. The prongs 504 also seat flush against the longitudinal side walls 302 of the pivot base 300. In addition, the corner portion 508 formed between each prong 504 and leg projection 506 extending therefrom engages with an end 610 of the slot 604 in the pivot pin 600 to thereby secure the pin 600 in place. The retaining member 500 thus holds the pins 600 in place, thereby mounting the pivot base 300 in the plate 102 prior to bone screw 400 insertion. When positioned, the center portion 502 of the retaining member 500 extends across a portion of the opening 310 of the pivot base 300 to interfere with the path of the screw head 404 to thereby secure a bone screw 400 in place, as will be described. In order to permit the bone screws 400 to be driven through the plate 102 and into the bone 12, the resilient retaining members 500 may deform elastically while the bone screw 400 is being driven into place, returning at least partially to their original shapes to cover at least a portion of the screw head 404 and inhibit bone anchor back out.

By another optional installation approach, one of the leg projections 506 extending from one of the prongs 504 may slide down the ramp portion 522 and be inserted into the through hole 602 of the pivot pin 600. Once the one leg projection 506 is secured in place, the other prong 504 may be compressed inwardly to clear the longitudinal side wall 302 of the pivot base 300 and then be moved down the ramp portion 322 until the other leg projection 506 is generally aligned with the through hole 602 of the opposite pin 600. The other prong 504 may then be released from the compressed position and may expand such that the leg projection 506 is inserted into the through hole 602 of the pin 600, thus bringing the retaining member 500 and the pivot members 600 to the installed and seated orientations described above with respect to the first installation method.

In a preferred form, the assembly of the bone plate 102, pivot base 300, pivot member 600, and retaining member 500 occurs pre-surgery, such that a surgeon receives the bone plate system 100 in this assembled configuration, with only the bone screws 400 to be inserted through the plate 102 and driven into the bone 12 and seated within the pivot bases 300 to secure the bone plate 102 in place. It will, of course, be appreciated that at least a portion of this assembly may be completed by the surgeon or clinician at the time of surgery. During surgery, the bone plate 102, including the pivot base 300, pins 600, and retaining member 500 secured therein, is generally aligned in position along the vertebrae or other bones 12 such that the bone screw 400 may then be inserted to secure the bone plate 102 to the bones 12. The bone plate 102 may optionally include pin through holes (not shown) for temporarily pinning the bone plate 102 in the desired position prior to driving the bone screw 400. Before inserting the bone screw 400, the pivot base 300 is aligned within the dynamized throughbores 108, 110 such that the pivot base 300 of each dynamized throughbore 108, 110 is placed at the lower end 116 of the throughbore 108, 110, as discussed above. The plate 102 is then ready to receive the bone screws 400.

Figure 22:
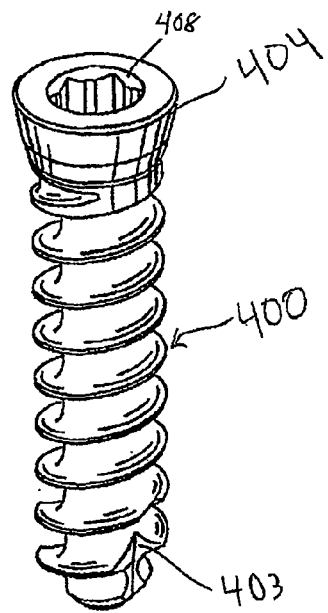
FIG. 22 is a perspective view of the bone screw of the dynamized or standard bone plate systems of FIG. 2 or 8.
Figure 23:
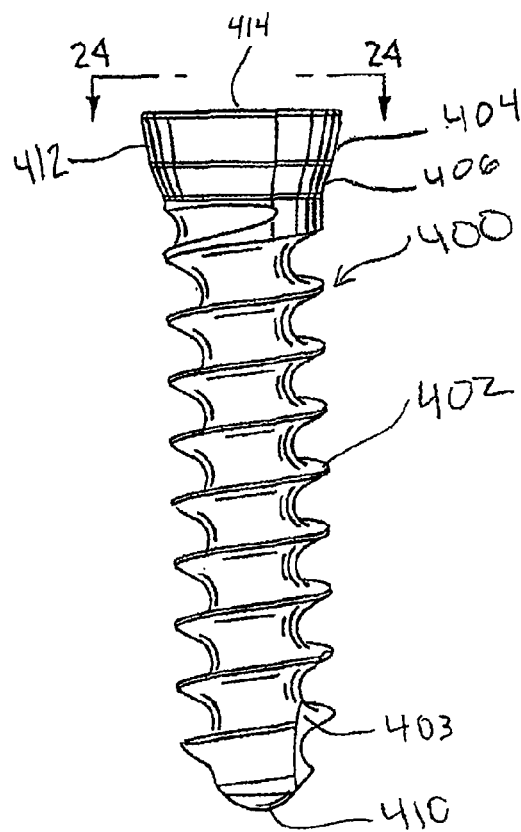
FIG. 23 is a side view of the bone screw of FIG. 22.
Figure 24:
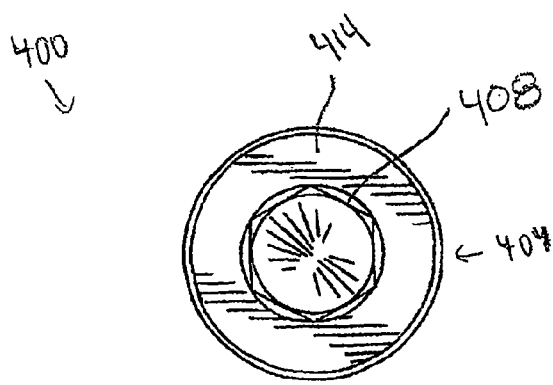
FIG. 24 is a top plan view of the bone screw of FIG. 22.

Referring now to FIGS. 22-24, The bone screw 400 has a threaded shank 402, a head portion 404, and a neck 406 therebetween. The bone screw 400 is aligned with the opening 310 of the pivot base 300. The screw head 404 preferably has a center hex aperture 408 that will engage with a driver 2200 to drive the bone screw 400 into the bone 12, but it will, of course, be appreciated that engagement configurations other than a hex aperture and hex-tipped driver are possible. The driver instrument or tool 2200 may engage the hex aperture 408 of the screw head 404, with the driver 2200 driving the bone screw 400 into the bone 12. As the screw head portion 404 approaches the retaining member 500, the screw head 404 contacts the center portion 502 of the retaining member 500. As the bone screw 400 continues into the bone 12 and plate 102, the arcuate profile of the screw head 404 cams against the straight center portion 502 of the retaining member 500 and forces, wedgelike, the center portion 502 to deflect outwardly—and preferably, elastically—to allow the screw head 404 to pass. Once the screw head 404 passes through and below the center portion 502 of the retaining member 500, the retaining member 500 generally returns at least partially to its position prior to insertion of the bone screw 400. The bone screw 400 is seated in the bone 12 and plate 102 such that the screw head 404 is generally below or approximately coincident with the upper face 314 of the pivot base 300 so that the center portion 502 of the retaining member 500 held within the pivot base 300 is over the head portion 404 of the bone screw 400 to prevent bone anchor back out. Once the bone screw 400 is fully seated in the opening 310 of the pivot base 300, the screw head 404 is aligned with the pivot pins 600 such that the screw head 404 holds the pins 600 and retaining member legs 506 in place, thus aiding in retaining the retaining member 500 itself and reinforcing its own back out obstacle.

A self-tapping screw 400 to be used in the bone plate system 100 is shown in FIGS. 22-24. The self-tapping screw 400 is provided with a tip 410 that is rounded and substantially dull. The bone screw 400 may be advanced into a pilot hole formed in the bone 12, and the threaded shank 402 forms cooperating threads in the bone 12 as the bone screw 400 is forcibly driven into the bone 12. The rounded tip 410 of the self-tapping screw 400 is intended to limit tissue damage. The tip 410 features a fluted portion 403 to remove bone chips as tapping occurs. In a preferred form, the self-tapping screw 400 is available in a variety of lengths. These lengths may be, for example, approximately 12, 14, or 16 millimeters, with the lengths representing the approximate amount of screw shank 402 that extends from the backside of the plate 102 after the head portion 404 bone screw 400 is fully seated in the opening 310 of the pivot base 300.

The screw head portion 404 preferably has a taper of the side walls 412 thereof that mates with the tapered side wall 312 of the opening 310 of the pivot base 300, as discussed above. The angle of the taper may be, for example, approximately ten degrees. The mating tapered side walls 312, 412 further limit the ability of the bone screw 400 to back out of its secured position within the plate 102 and in the bone 12. The taper lock condition also minimizes the rotational translation between the bone screw 400 and the pivot base 300. The screw head portion 404 may also be optionally colored to create visual contrast relative to the retaining member 500, the pivot base 300, and the plate 102. In a preferred form, for example, the bone screw 400 has a major diameter of approximately 4.5 millimeters and a minor diameter of approximately 3.0 millimeters. The bone screw 400 further has a pitch and a half lead-in to increase the cross-sectional area for improved head strength. The screw head portion 404 preferably has a top surface 414 that is generally flat. A convex shape may promote or assist bone anchor back out as the convex head may force the retaining member 500 open. Alternatively, a concave shape may be employed for the top surface 414.

By another optional approach, the bone anchor may be a self-drilling screw (not shown). Self-drilling screws generally feature tips that are pointed and at least one of a cutting flute formed in the threaded shank to aid in removing bone chips as they are cut. The cutting edges of the tip may be approximately 90 degrees relative to one another and are generally relieved at a rate of approximately 0.010 per 100 degrees of rotation to aid in cutting. The self-drilling screw may be placed against a bone 12 or in a pilot hole of a bone 12 and is advanced by forcibly driving the screw into the bone 12. The cutting flute forms a hole in the bone 12 as the screw is advanced, and the threads cut into the bone 12 to form cooperating threads in the bone 12. Preferably, the self-drilling screws are provided in a length short enough to prevent accidental driving of these sharper screw tips into sensitive tissues, such as nerves or blood circulatory passages. In a preferred form, the self-drilling screw is available in variety of lengths. These lengths may be, for example, approximately 12, 14, or 16 millimeters in length with the screw lengths being designated as defined above.

It should also be noted that, in the event the bone 12 is stripped, rescue screws (not shown) may be provided for the bone plate system 100 for securing in the bone. A rescue screw is a screw that has a larger thread diameter, or a larger central or minor diameter, or both. The rescue screw is able to gain purchase in the stripped hole, treating the stripped hole as if it were a pilot hole, by virtue of its larger size. In a preferred form, the rescue screw used in this system may feature a major diameter of approximately 4.5 millimeters and a minor diameter of approximately 3.0 millimeters. Also in a preferred form, the rescue screw is self-tapping and is available in a variety of lengths. These lengths may be, for example, approximately 12, 14, or 16 millimeters with the screw lengths being designated as defined above.

The angle of bone anchor toggle is limited by the geometry of the throughbore 106,108,110 and the pivot base 300 mounted therein. As discussed above, in a preferred form, the pivot base 300, and thus the bone screw 400 with a head portion 404 seated therein, may be configured to pivot plus or minus approximately ten degrees relative to the plate 102 in the direction of the longitudinal axis of the plate 102 (cephal/caudel direction) and approximately 0 degrees relative to the plate 102 in the direction of the lateral axis of the plate 102(medial/lateral direction).

Referring now to FIGS. 7-12, a standard bone plate system 200 is shown. The standard bone plate 200 generally includes a bone plate 202 secured to the bones 12 with bone screws 400. As with the previous bone plate 102 of the dynamized bone plate system 100, the present bone plate 202 includes through throughbores 206, 208, 210 formed in the plate 202, with a generally rectangular pivot base 300 secured within each throughbore 206, 208, 210. The bone screws 400 are secured in the pivot base 300 by retaining members 500.

As seen in FIGS. 7-12, the same pivot base 300, bone screw 400, retaining member 500, and pivot members 600 used in the dynamized bone plate system 100 may be used in the standard bone plate system 200. The main difference between the dynamized bone plate system 100 and the standard plate system 200 is the availability of translational movement within the throughbores. While the dynamized plate 102 included dynamized throughbores 108, 110 to allow for translational movement of the pivot base 300 relative to the plate 102, the standard plate 202 includes non-dynamized or standard throughbores 206, 208, 210 of generally identical size that allow relatively little to no translational movement. The dynamized and non-dynamized throughbores have generally similar construction, with the length of the longitudinal side wall portions 126, 226 being the notable difference in allowing for or limiting the translational movement of the pivot base 300 within the plate 102, 202. With the exception of having all standard throughbores 206, 208, 210, the standard plate 202 has generally the same construction and configuration as the dynamized plate 102. It should be noted that similar elements of each plate 102, 202 have been assigned similar reference numbers for consistency.

Figure 7:
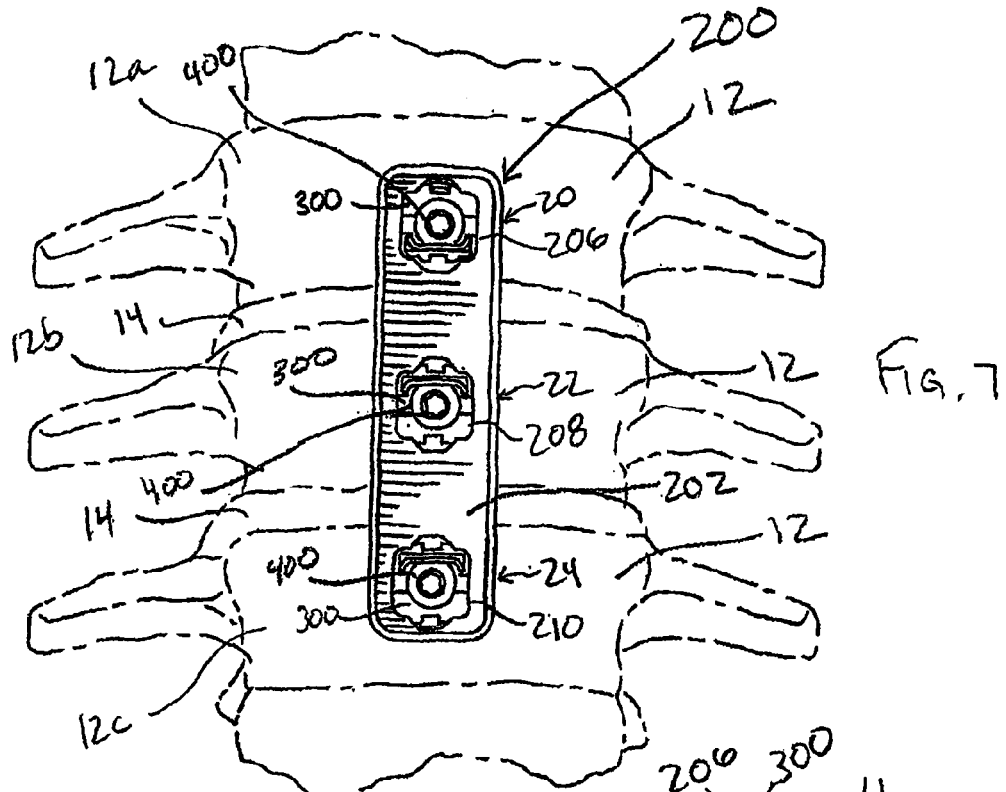
FIG. 7 is a plan view of a standard bone plate system including features in accordance with the present invention and securing vertebrae in a particular orientation.
Figure 8:
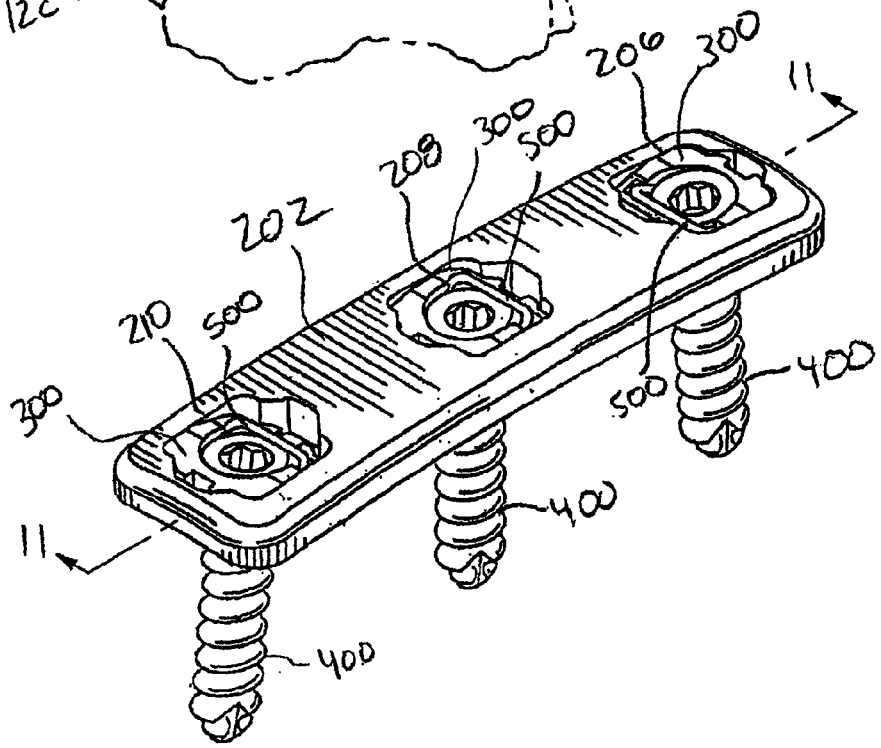
FIG. 8 is a perspective view of the standard bone plate system of FIG. 7.
Figure 9:
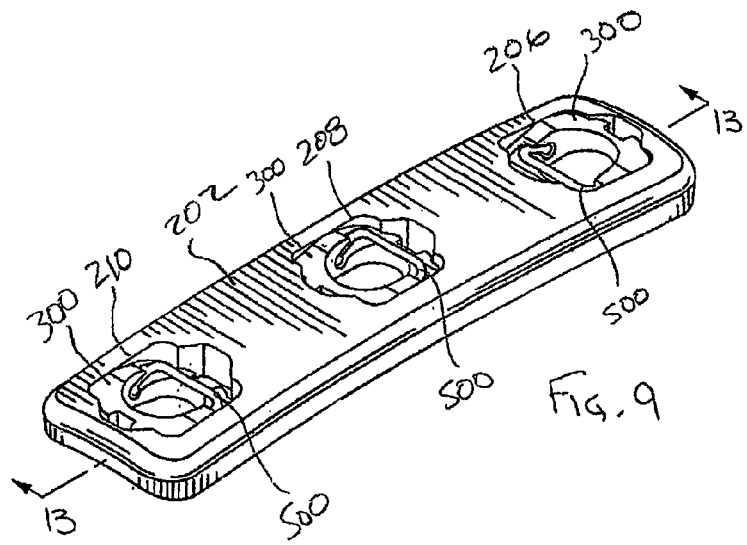
FIG. 9 is a perspective view of the standard bone plate system of FIG. 8 without the bone anchors.

The bone plate 202 preferably has a throughbore 206, 208, 210 located at each level at which a bone 12 is to be secured thereto, with the throughbores 206, 208, 210 defining tiers 20, 22, 24 of the bone plate 202, as depicted in FIG. 7. A single throughbore 206, 208, 210 is formed in the plate 202 at each tier 20, 22, 24. Again, any number of tiers could be provided for securing a plurality of bones 12.

As shown in FIGS. 17-20, each throughbore 206, 208, 210 has a generally rectangular profile comprised of a pair of longitudinal side wall portions 226 and a pair of end wall portions 228. The pair of longitudinal side wall portions 226 of each throughbore 206, 208, 210 are generally the same length and are generally sized to receive the pivot base 300 therein with little or no side-to-side translational movement allowed relative to the longitudinal axis of the plate 202. The end wall portions 228 are generally the same size for each throughbore 206, 208, 210 and are generally sized to accommodate the length of the pivot base 300 with little more clearance than what is needed to accommodate the pivoting motion of the pivot base 300 relative to the plate 202. In the standard plate 202, the longitudinal side wall portions 226 and the end wall portions 228 are generally just minimally larger in terms of length and width with respect to the corresponding side wall portions 302 and end wall portions 304 of the pivot base 300 to restrict the translational movement of the pivot base 300. In addition, relief areas 218 extend from the end wall portions 228 to allow for instrument clearance and forked projections 306.

Each throughbore 206, 208, 210 has a floor portion 224 extending along and generally perpendicular to each longitudinal side wall portion 226 along the bone plate 202. The floor portions 224 extend into the throughbore 206, 208, 210 to narrow the throughbore hole such that the floor portions 224 support bottom portions of the pivot base 300. In addition, the floor portions 224 support pivot members 600 extending from the pivot base 300. The floor portions 224 also serve to limit the pivotal movement of the pivot base 300.

Cavities, such as, in a preferred form, slot portions or elongated grooves 230 are formed in the side wall portions 226 just above the intersection of the floor portion 224 and the longitudinal side wall portion 226. The slot portions 230 allow the pivot members 600 extending from either side of the pivot base 300 to be received in the longitudinal side wall portions 226 of each throughbore 206, 208, 210. The slot portions 230 are sized in length to receive the pivot pins 600. Although the slot portions 230 may extend along the length of the side wall portions 226, the pivot base 300 will experience little or no translation, as the length of the side walls portions 226 serves as the limiting factor in restricting the translational movement of the pivot base 300 within the throughbore 206 208, 210. In the standard plate 202, the longitudinal side wall portions 226 are generally minimally longer than the length of the longitudinal side wall portions 302 of the pivot base 300 to restrict the translational movement of the pivot base 300. The slot portions 230 are generally sized in height and depth to accommodate the pivot members 600 therein.

The pivot members or pins 600 securing the pivot base 300 in the slots 230 limit pivotal movement of the pivot base 300 in the direction of the lateral axis of the plate 202 within the throughbore 206, 208, 210. As with the dynamized plate 102, the pivot base 300 in the standard plate 202 is allowed to pivot in the direction of the longitudinal axis of the plate 202, and the range of pivoting may be, for example, approximately plus or minus ten degrees, with the floor portions 224 and the configuration of the pivot base 300 limiting the amount of pivotal movement.

Turning now to FIGS. 36-42, another embodiment according to the present invention is shown in the form of a dynamic or dynamized bone plate system 1100. The bone plate system 1100 is similar in many respects to the dynamized bone plate system 100, with one of the important distinctions being that no resilient retaining member 500 is used. In light of this, discussion of the present bone plate system 1100 will primarily focus on aspects of the present embodiment that differ from the previously discussed dynamized bone plate system 100.

The bone plate system 1100 comprises a bone plate 1102 featuring throughbores 1106, 1108, 1110 on each tier 20, 22, 24, respectively. The present bone plate 1102 may also feature indented regions 1160, which offer enhanced visualization of the surgical site, graft region, and/or intervertebral disc space. In addition, the reduced cross-section in these regions allows a surgeon or clinician to bend the plate 1102 with greater precision should the plate 1102 require bending to better contour the patient's natural spinal curvature. The reduced cross section in the regions of the plate 1102 between opposing indented regions 1160 make the plate 1102 easier to bend in these regions, avoiding bending at the throughbores 1106, 1108, 1110, which is preferable because if the plate 1102 is bent too close to or within the region of the throughbores 1106, 1108, 1110, the structural integrity of the throughbores 1106, 1108, 1110 and the intended configurations between the throughbores 1106, 1108, 1110 and the corresponding pivot bases 1300 may be compromised.

Figure 129:
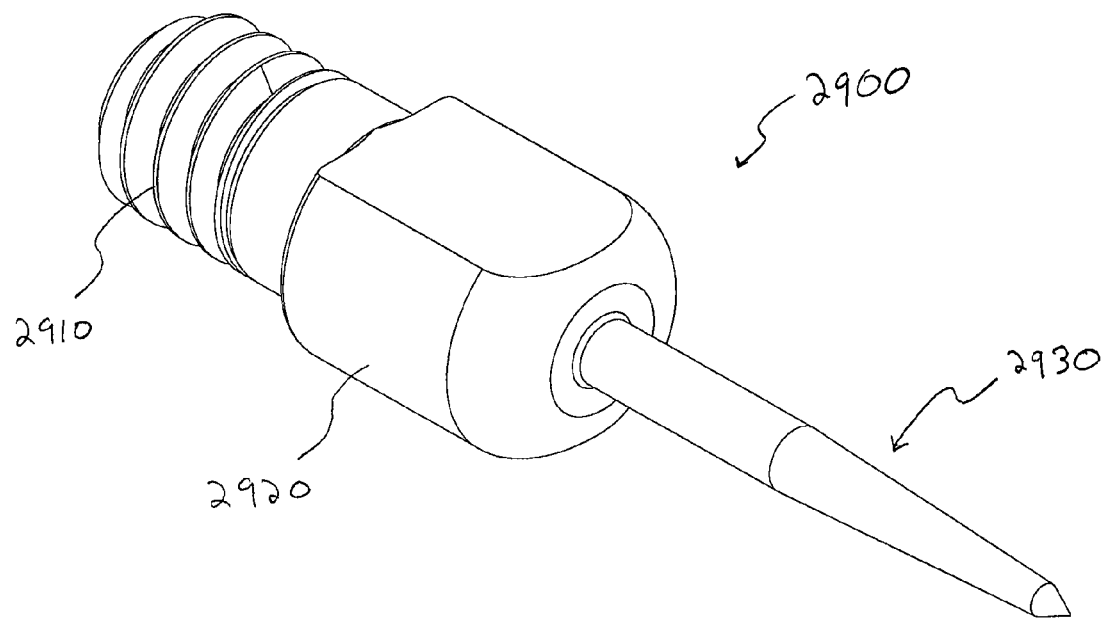
Figure 130:
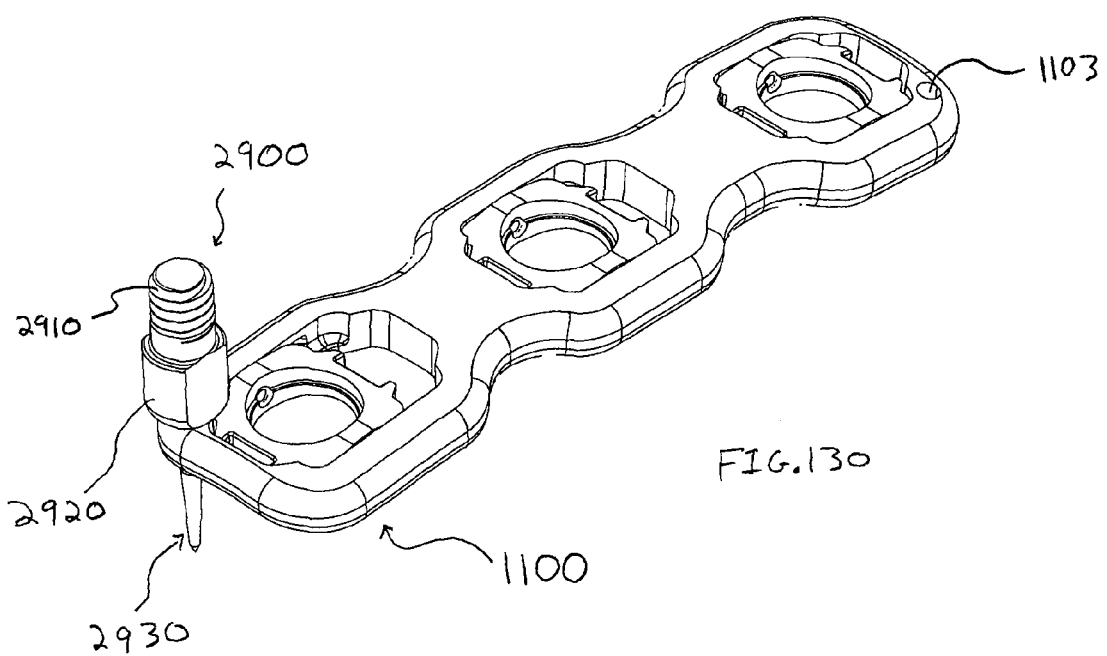
Figure 131:
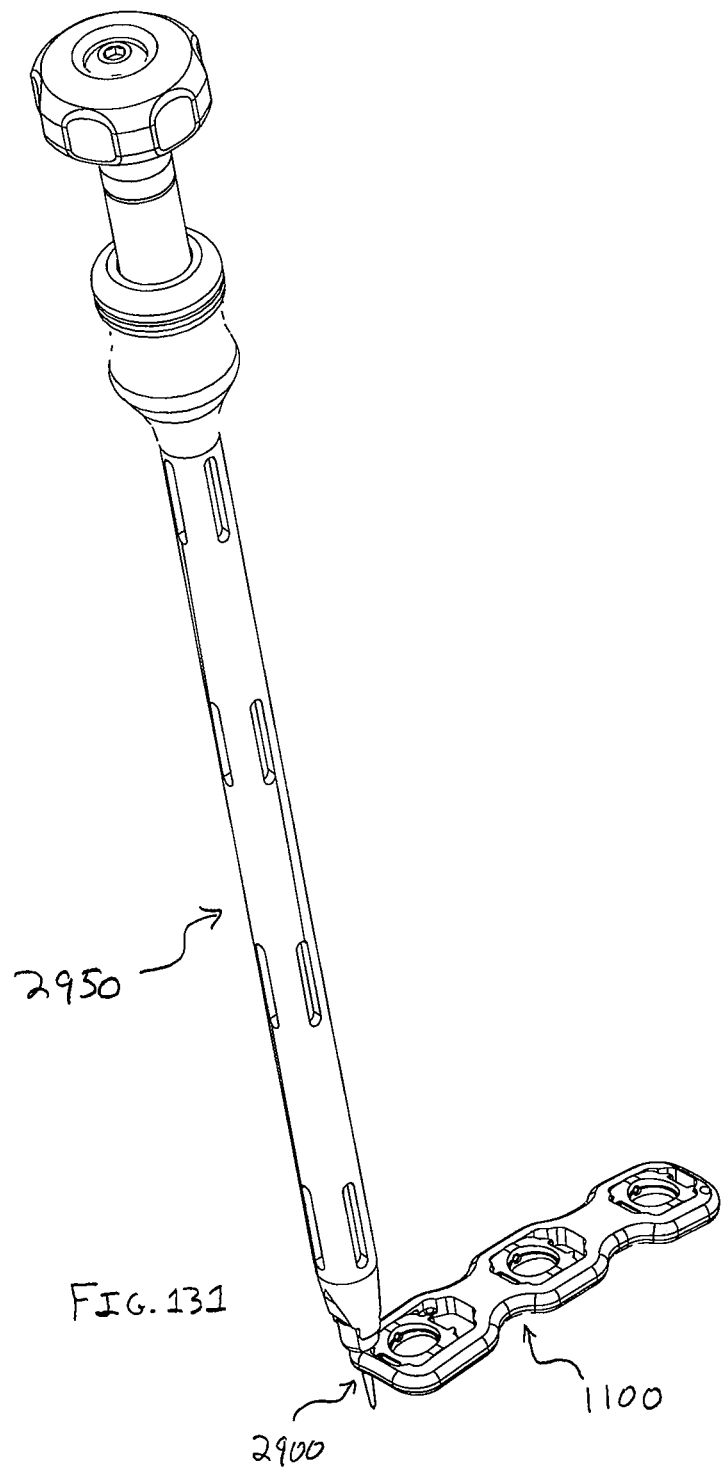

An additional difference between the present bone plate 1102 and the previously described dynamic or dynamized bone plate 102 is that the plate 1102 may feature at least one of an aperture 1103 for temporarily holding the bone plate 1102 in the location and orientation desired by the surgeon such that the plate 1102 is retained in the desired position before bone anchors such as bone screws 1400 are installed. Generally, bone pins are inserted through the apertures 1103, and the bone pins are intended to be temporary and are designed to cause minimal damage to the osseous tissue such that any region affected by the bone pins will heal quickly and the mechanical characteristics of the vertebrae 12 will see little or no appreciable degradation. Each bone pin 2900 preferably has a threaded portion 2910, an intermediate portion 2920, and a tip 2930, as shown in FIG. 129. Tip 2930 extends through the aperture 1103 when the bone pin 2900 is in position to hold the bone plate 1102 against a vertebra, as shown in FIG. 130. The threaded portion 2910 enables the bone pin 2900 to be releasably attached to a pin instrument 2950, as shown in FIG. 131. In use, a surgeon may insert a bone pin 2900 through a first aperture 1103 and into a vertebra, unscrew the pin instrument 2950 from the first bone pin 2900, and repeat the procedure with a second bone pin 2900 and second aperture 1103. The use of bone pins 2900 in apertures 1103 on opposite corners of the bone plate 1102 provides a secure, but temporary, method of retaining the plate 1102 in the desired position before anchors are installed. Though this feature is not shown on the plates 102, 202 discussed above, it will be appreciated that this or a similar feature may be present on all embodiments shown for exemplary purposes herein. It will further be appreciated that this feature would be optional and the surgeon may choose not to use the apertures 1103 even if the apertures 1103 are present on the bone plate being installed.

The plate 1102 is, in many respects, quite similar to the previously described bone plate 102. The bone plate 1102 features a top face 1104 and a bottom face 1114, as well as a pair of generally parallel longitudinal side wall portions 1150 and generally parallel end wall portions 1152. In addition, the throughbores 1106, 1108, 1110 of the present plate 1102 are very similar to the throughbores 106, 108, 110 of the previously discussed dynamized plate 102 such that the geometric relationships and the movements of pivot bases 1300 within the throughbores 1106, 1108, 1110 are largely the same. The throughbores 1106, 1108, 1110 feature longitudinal sidewall portions 1126, elongated grooves or slot portions 1130, floor portions 1124, end wall portions 1128, angled walls 1120 which terminate in end walls 1122 and define relief areas 1118, and a notched profile 1140. The dynamized throughbores 1108, 1110 also feature lower ends 1116 whereby pivot bases 1300 disposed within the dynamized throughbores 1108, 1110 may be positioned to allow maximum settling of the vertebrae 12. It should be noted that many similar feature to previously described embodiments retain a similar denotation; for example, the lower ends 116 of the plate 102 and the lower ends 1116 of the plate 1102.

The throughbores 1106, 1108, 1110 are designed to accommodate pivot bases 1300, which are similar in many respects to the pivot bases 300 discussed above, but the pivot bases 1300 do not use the resilient retaining members 500. Rather, the pivot bases 1300 are retained within the throughbores 1106, 1108, 1110 primarily by pivot members or pivot pins 1600 shown in FIGS. 55, 56. The pivot pins 1600 are similar in many respects to the previously discussed pivot members 600, but the present pivot pins 1600 do not feature a center through hole or a slot which were used to engage the leg portions 506 of the retaining member 500. The pivot pins 1600 feature a front surface 1610 of a rounded or partially rounded tip 1620, and a body portion 1630, but the pivot pins 1600 also feature a tapered region 1640 which terminates in a slightly enlarged portion 1650 that aid in the assembly process. The pivot pin 1600 also features an end surface 1660 and in a preferred form the pivot pin 1600 is solid, as it need not engage a retaining member 500.

During assembly of the bone plate 1102 and the pivot base 1300, the pivot base 1300 is aligned in one of the throughbores 1106, 1108, 1110. The pivot pins 1600 are inserted into apertures 1320 in the pivot base 1300 and are forced further into the apertures 1320 until the enlarged portion 1650 comes into a tight frictional or interference engagement with the pivot base 1300, a portion of the pivot pin 1600 projects into the slot portion 1130 of the plate 1102, and the rear surface 1660 of the pivot member 1600 will not interfere with the insertion of the bone screws 1400.

The pivot bases 1300, shown in FIGS. 48-54, are similar in many respects to the pivot bases 300 described previously, but the pivot bases 1300 may be easier to manufacture as they do not require additional geometric considerations to accommodate the use of the retaining members or clips 500. As with the pivot base 300 discussed above, the present pivot base 1300 features longitudinal side walls 1302, end wall portions 1304, forked projections 1306 which define a space 1308 therebetween, a center through opening 1310, a top face 1314, a bottom face 1316, and because the top and bottom faces 1314, 1316 are generally convex in shape, the pivot base 1300 has a thicker center portion 1318.

Within the opening 1310, the pivot base 1300 features apertures 1320 for receiving pivot members or pins 1600. The opening 1310 also features an enlarged upper portion 1312 and a lower portion 1313 to accommodate the head geometry of a bone anchor such as a bone screw 1400.

Also similar to the previously discussed pivot base 300, the present pivot base 1300 features longitudinal recessed portions 1334, an upper level bottom face 1336, a lower level bottom face 1338, and a notched profile 1340 which is contoured to the notched profile 1140 of the plate 1102, all of which were described in detail with respect to the pivot base 300.

The pivot bases 1300 are designed to pivot with respect to the plate 1102, and this will be accomplished by clearances and geometric relationships that allow for this motion. For example, the clearance between the longitudinal side wall 1302 and the longitudinal side wall portion 1126 may be as much as 0.002 inches, and in the standard throughbores such as the standard throughbore 1106 of the present bone plate system 1100, the clearance between the end wall portions 1304 of the pivot base 1300 and the end wall portions 1128 of the plate 1102 may be as much as 0.005 inches, which may allow a slight amount of translation relative to the plate 1102 in the standardized throughbore 1106, but this amounts to very little translation relative to the dynamized throughbores 1108, 1110 and may be necessary to allow for the pivoting motion of the pivot base 1300.

The pivot base 1300 is configured to accommodate a bone anchor or fastener such as the bone screw 1400 shown in FIGS. 57-59. The bone screw 1400 is shown with a rounded or dull tip 1410, which is customary for a self-tapping screw, but it will be appreciated that the screw 1400 could have a sharp tip and be a self-drilling screw or it could be any type of bone screw that features a screw head configured to be seated within the pivot base 1300. In a preferred form, the threaded shank 1402 features a fluted portion 1403 to remove bone chips upon installation. Also in a preferred form, the bone screw 1400 would be available in different lengths. These lengths may be, for example, 12, 14, or 16 millimeters, with the screw length representing the approximate amount of screw shank 1402 that extends from the backside of the plate 1102 after the screw 1400 is fully seated in the opening 1310 of the pivot base 1300.

In the present embodiment of the dynamic or dynamized bone plate system 1100, a head portion or head end 1404 of the bone anchor 1400 is a resilient head portion. The screw head 1404 features a plurality of upper ledge portions 1412 that define an upper surface 1414 and are configured to compliment the enlarged upper region 1312 of the through hole or opening 1310 of the pivot base 1300. Similarly, lower portions 1413 complement the lower portion 1313 of the pivot base 1300, and the upper and lower portions 1412 and 1413 are separated from one another by a plurality of driver engagement slots 1430, as shown in FIG. 57. A chamfer 1416 begins at the bottom of the lower portion 1413 and angles inwardly, terminating at the top of the shank 1402, thus serving as a transition between the screw head 1404 and the threaded region 1402.

During installation of the plate system 1100, the bone screw 1400 is driven into the bone 12 with the shank 1402 passing through the through hole or opening 1310 of the base member 1300. When the screw head portion 1404 is seated properly within the opening 1310 and the ledge 1412 is generally flush with the annular lip between the upper and lower opening portions 1312, 1313, a locking member such as a locking screw or setscrew 1450 will be seated to expand the resilient screw head 1404 and/or cause hoop stress to be applied on the walls of the opening 1310 of the pivot base 1300.

The locking member or locking screw 1450 is designed to be inserted into a cavity 1440 within the screw head portion 1404 and the locking screw 1450 is generally rigid in comparison to the generally resilient screw head portion 1404. In a preferred form, the surgeon or clinician would receive the bone screw 1400 and locking screw 1450 as one unit, with the locking screw 1450 in the proud position as shown for exemplary purposes in FIG. 58. Also in a preferred form, a driver 2600 will first engage the screw 1400 and drive the screw 1400 into the bone 12 before the locking screw 1450 is engaged by a driver (not shown), preferably within a hex aperture 1458, and is driven into a seated configuration thereby to impart hoop stress to the screw head 1404 as shown in FIG. 59 and thus aid in retaining or locking the screw head 1404 within the opening 1310 of the pivot base 1300 and inhibit back out by creating enhanced frictional engagement between the screw head 1404 and the pivot base 1300.

As shown in FIGS. 57-59 the screw head 1404 has a chamfer 1425 that compliments an inwardly sloped surface 1465 of the locking member 1450. An annular lip 1462 creates an annular groove 1460 which, along with a ledge 1422 of the screw head 1404, inhibits the locking member 1450 from being removed from the screw head portion 1404. The locking member 1450 further defines a threaded shank 1452, which allows the locking screw 1450 to be driven further into the internal threaded region 1442 of the bone screw 1400. The locking member 1450 may be driven until fully seated when the a bottom surface 1464 of the annular lip 1462 of the locking member 1450 contacts a bottom surface 1444 of the cavity 1440. An outer surface 1451 of the locking screw 1450 is then in contact with the ledge 1422, imposing hoop stress on the head portion 1404 of the bone screw 1400 and expanding the head portion 1404 to create enhanced engagement with the opening 1310 of a pivot base 1300.

Figure 62:
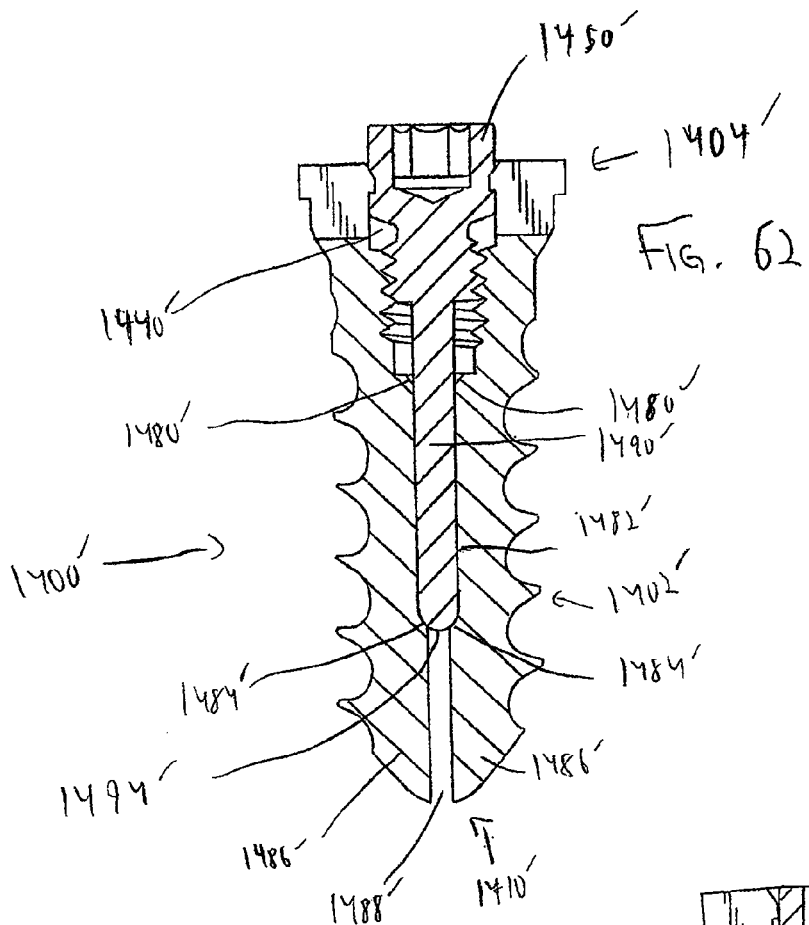
FIG. 62 is a cross-sectional side view of the rescue screw and locking member of FIG. 61 with the locking member proud.
Figure 63:
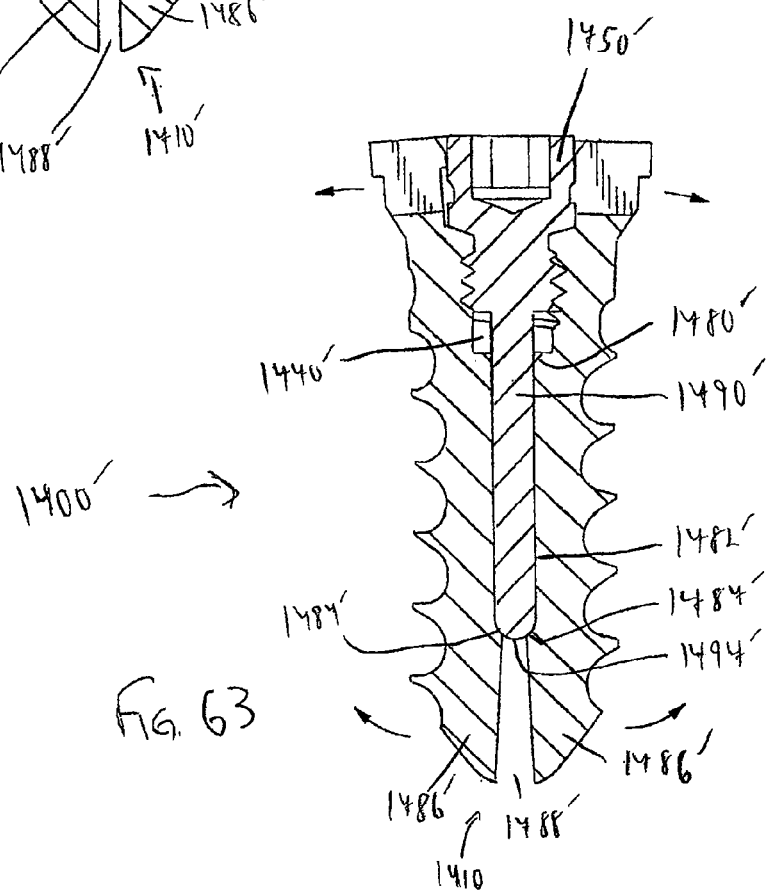
FIG. 63 is a cross-sectional side view of the rescue screw and locking member of FIG. 61 with the locking member seated.
Figure 64:
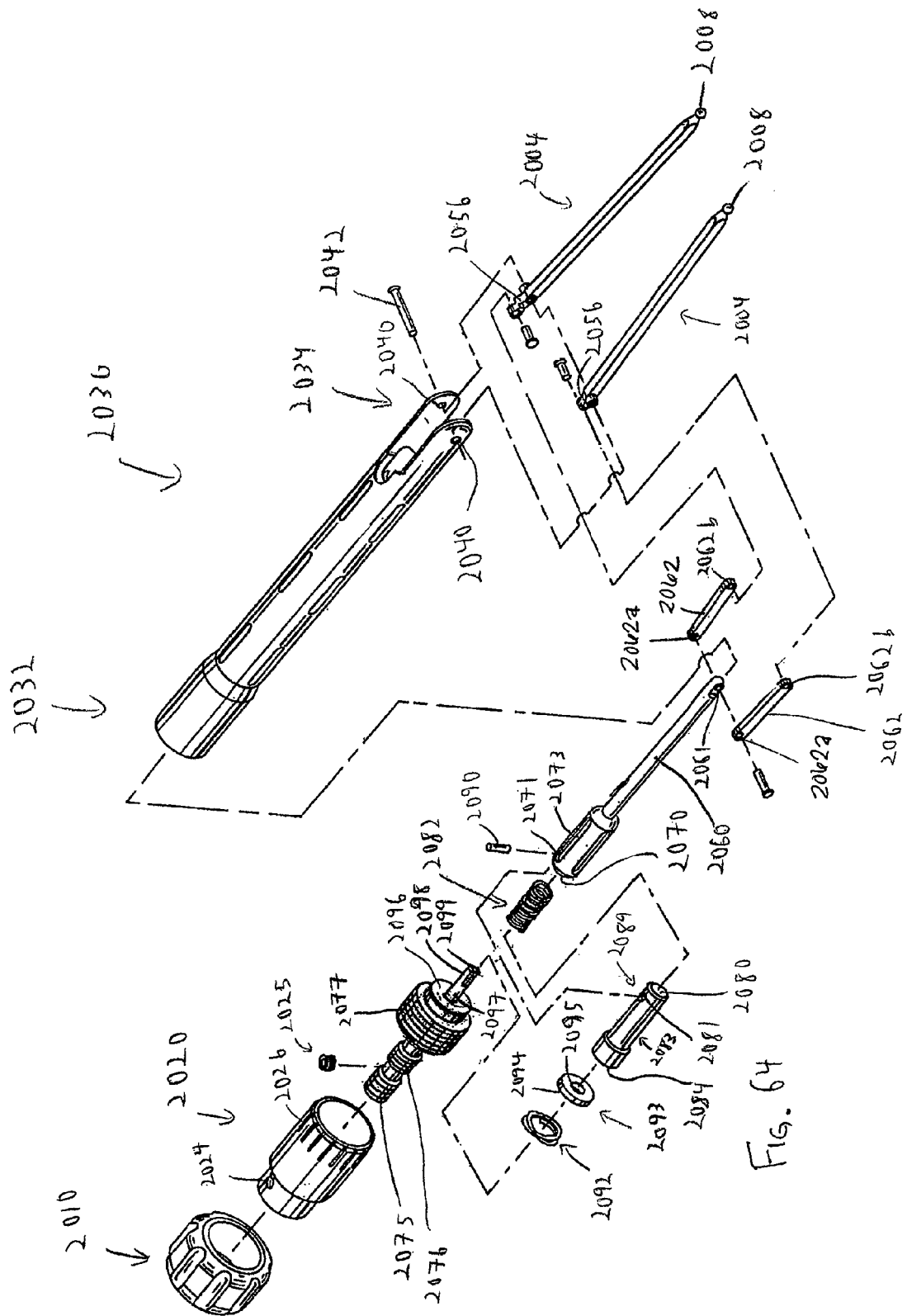
FIG. 64 is an exploded perspective view of measuring calipers including features in accordance with another aspect of the present invention.
Figures 65, 66:
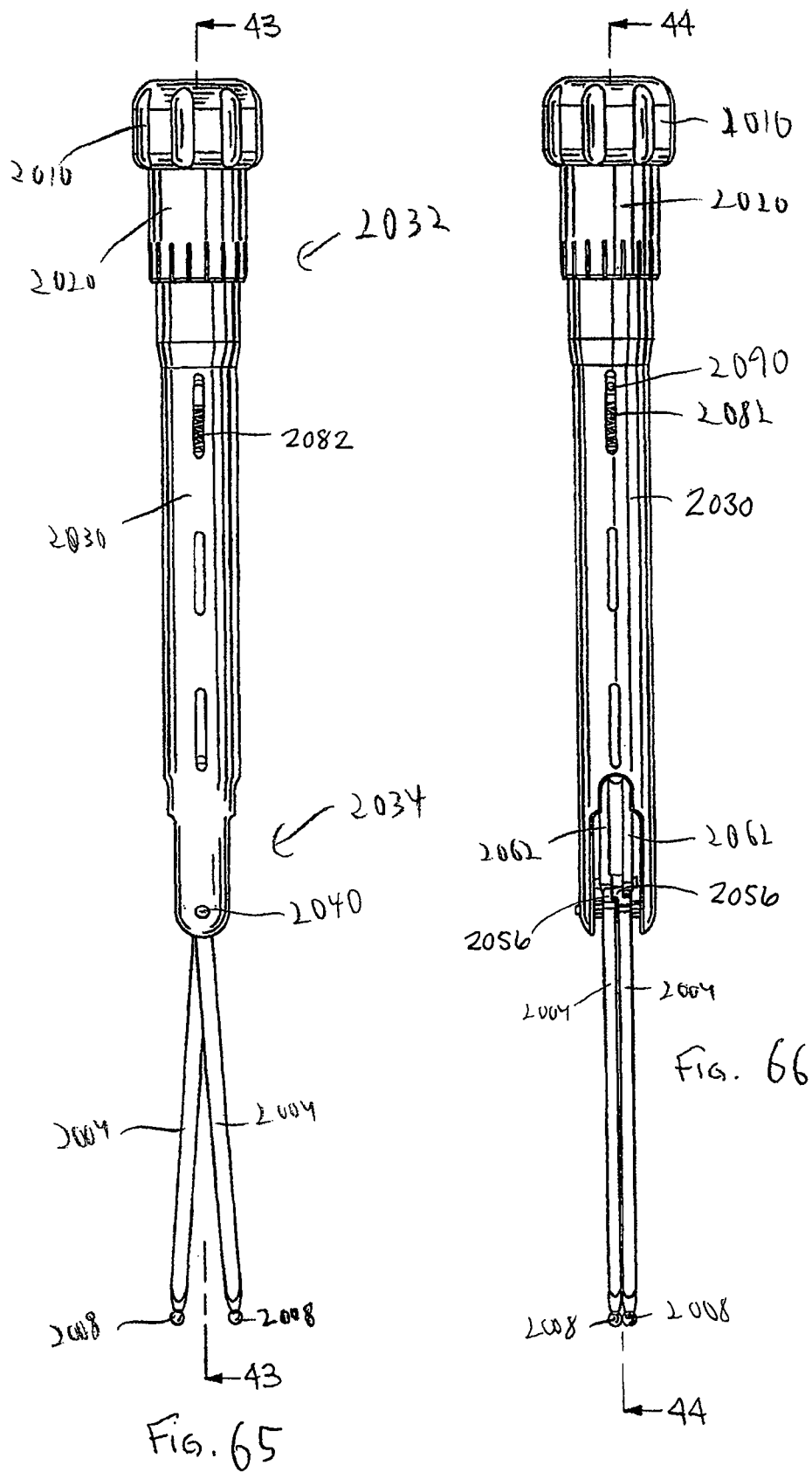
FIG. 65 is a side view of the measuring calipers of FIG. 64.
FIG. 66 is a side view of the measuring calipers of FIG. 64 turned ninety degrees from the side view of FIG. 65.
Figure 67:
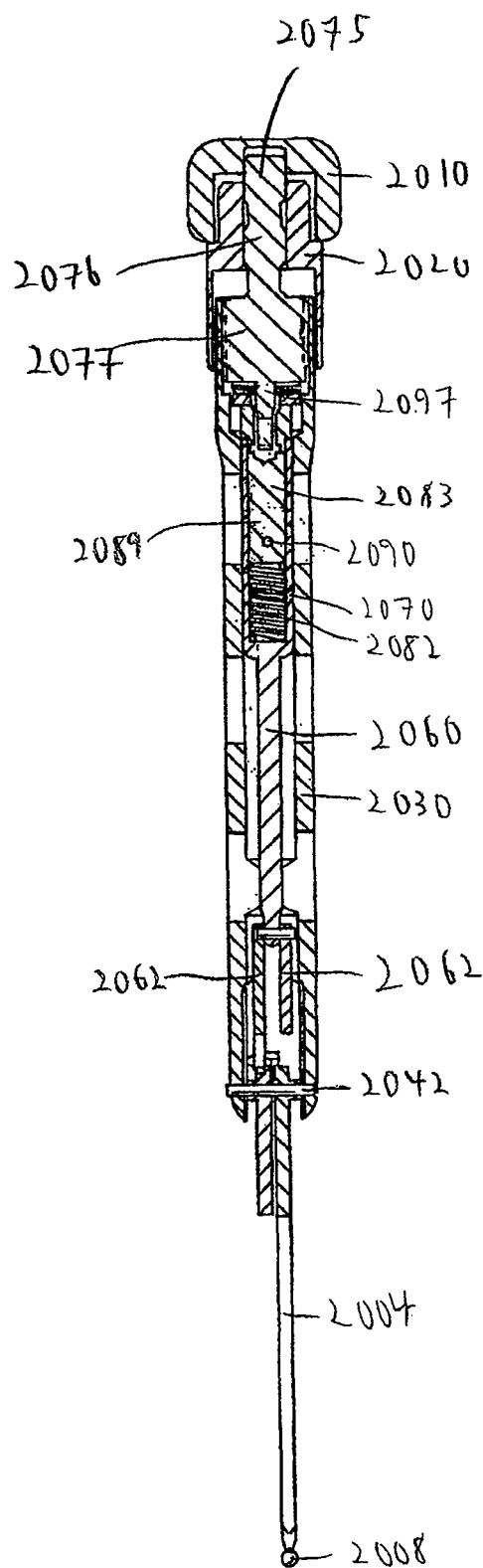
FIG. 67 is a cross-sectional side view of the measuring calipers of FIG. 64.
Figure 68:
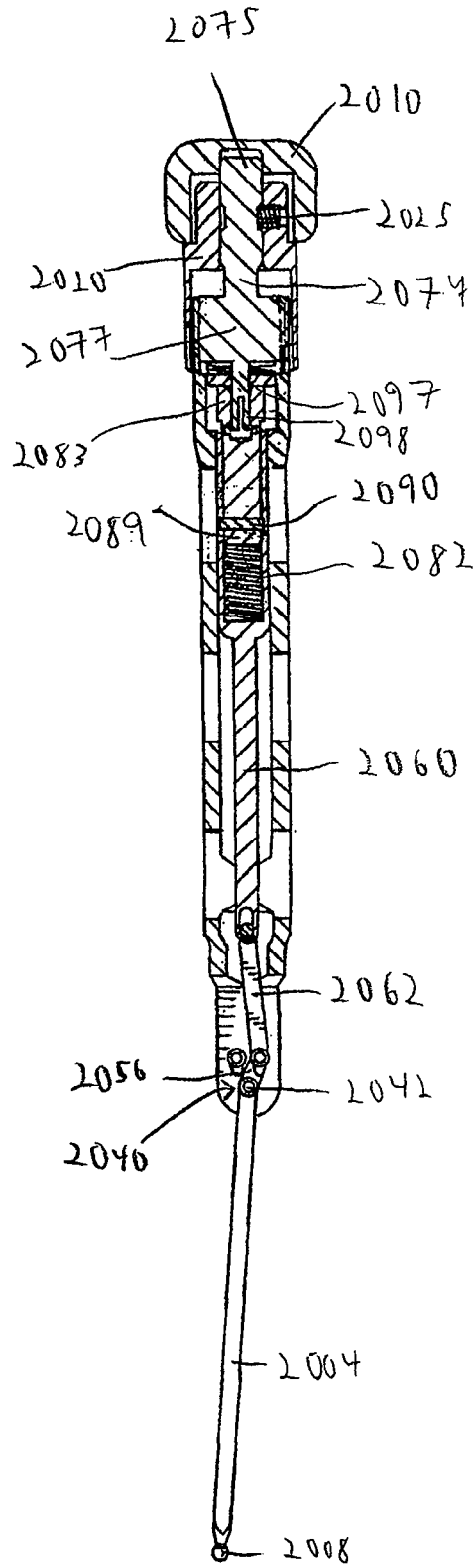
FIG. 68 is a cross-sectional side view of the measuring calipers of FIG. 64 turned ninety degrees from the cross-sectional side view of FIG. 67.
Figures 69, 70:
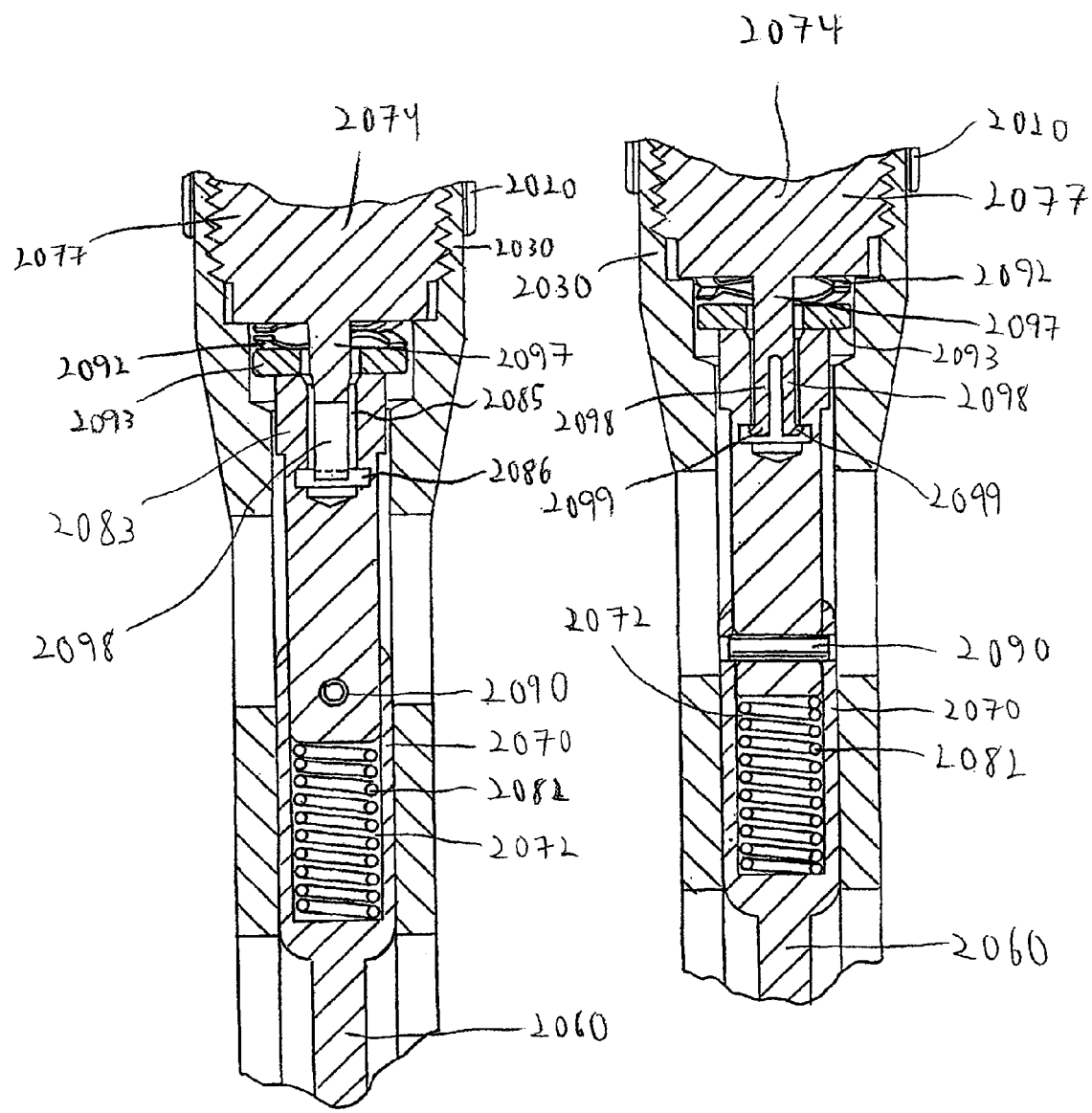
FIG. 69 is a close-up cross-sectional side view of the measuring calipers of FIG. 67.
FIG. 70 is a close-up cross-sectional side view of the measuring calipers of FIG. 68.
Figure 71:
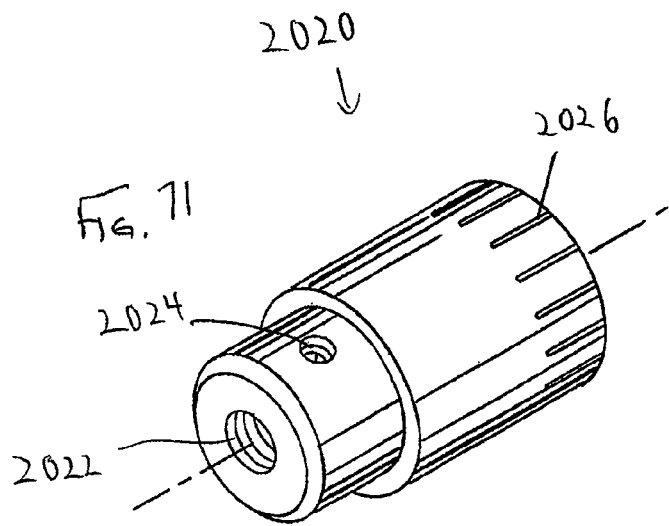
FIG. 71 is a perspective view of the indicator sleeve of the measuring calipers of FIG. 64.
Figure 72:
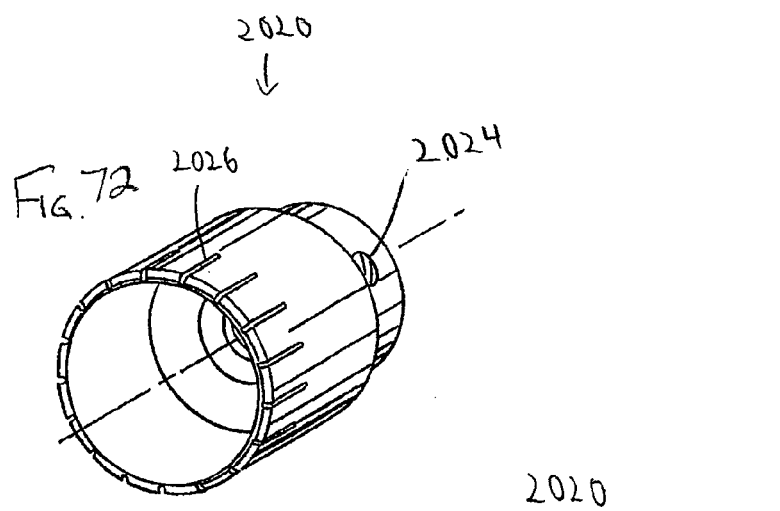
FIG. 72 is a perspective view of the indicator sleeve of the measuring calipers of FIG. 64.
Figure 73:
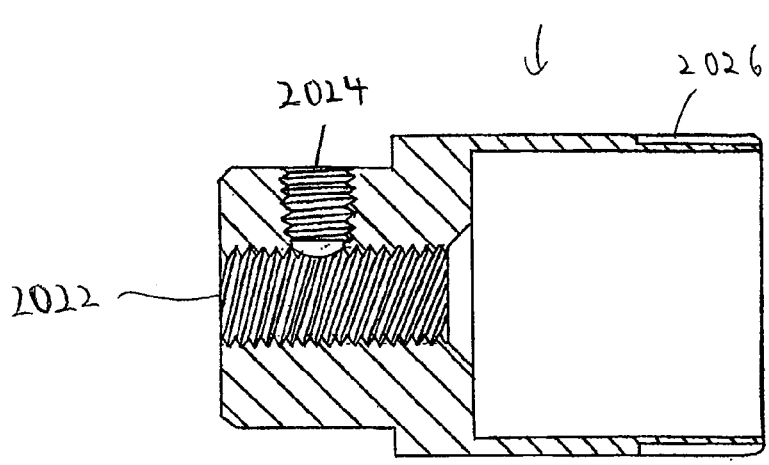
FIG. 73 is a cross-sectional side view of the indicator sleeve of the measuring calipers of FIG. 64.

In the event that the bone 12 is stripped during bone screw insertion, another bone anchor such as a rescue screw 1400', shown in FIGS. 60-63, may be employed. The rescue screw 1400' differs from the rescue screws (not shown) described above with respect to the previously discussed bone plate system 100 because the rescue screws of the previous system 100 feature dimensions that, upon installation, interfere with the dimensions of the hole in the bone 12. The present rescue screw 1400' is installed in the same manner as the bone screw 1400 and is then expanded to cause hoop stress and/or create interfering dimensions with the hole into which the rescue screw 1400' is installed. The rescue screw 1400' is the same in many respects to the bone screw 1400, but a cavity 1440' terminates in a chamfer 1480' which leads to a channel 1482', as shown in FIGS. 62, 63. The channel 1482' ends in curved portions 1484' and the screw tip 1410' is then split into a plurality of tip segments 1486' by slots 1488'. Thus, in a preferred form, both the screw head portion 1404' and the screw tip 1410' of the rescue screw 1400' are resilient. Also in a preferred form, the rescue screw 1400' would be available in different lengths. These lengths may be, for example, 12, 14, or 16 millimeters, with the screw length representing the approximate amount of screw shank 1402' that extends from the backside of the plate 1102 after the rescue screw 1400' is seated in the opening 1310 of the pivot base 1300.

In addition, the rescue screw 1400' will also feature a locking member such as a locking screw 1450' that is similar in many respects to the locking screw 1450 described above, but differs with respect to the fact that the locking screw 1450' features a post 1490' that extends generally parallel to the longitudinal axis of the screw 1400'. The post 1490' terminates in a rounded tip 1494' which, in the proud configuration shown in FIG. 62, is generally flush with the curved portion 1484' of the rescue screw 1400'. After the rescue screw 1400' is properly seated within the opening 1310 of the pivot base 1300, the locking screw 1450' may be seated as described above with respect to the locking screw 1450, but as the locking member 1450' is seated, the post 1490' will be advanced, pushing the rounded tip 1494' past the curved portions 1484' of the channel 1482' and expanding the screw tip segments 1486' so that the screw tip segments 1486' will cause interference and/or enhanced frictional engagement with the hole formed in the bone 12. In this way, seating the locking member 1450' of the rescue screw 1400' will expand both the screw head 1404' and the screw tip 1410' as shown in FIG. 63, avoiding the need to drill a second hole in the vertebrae 12.

Figure 43:
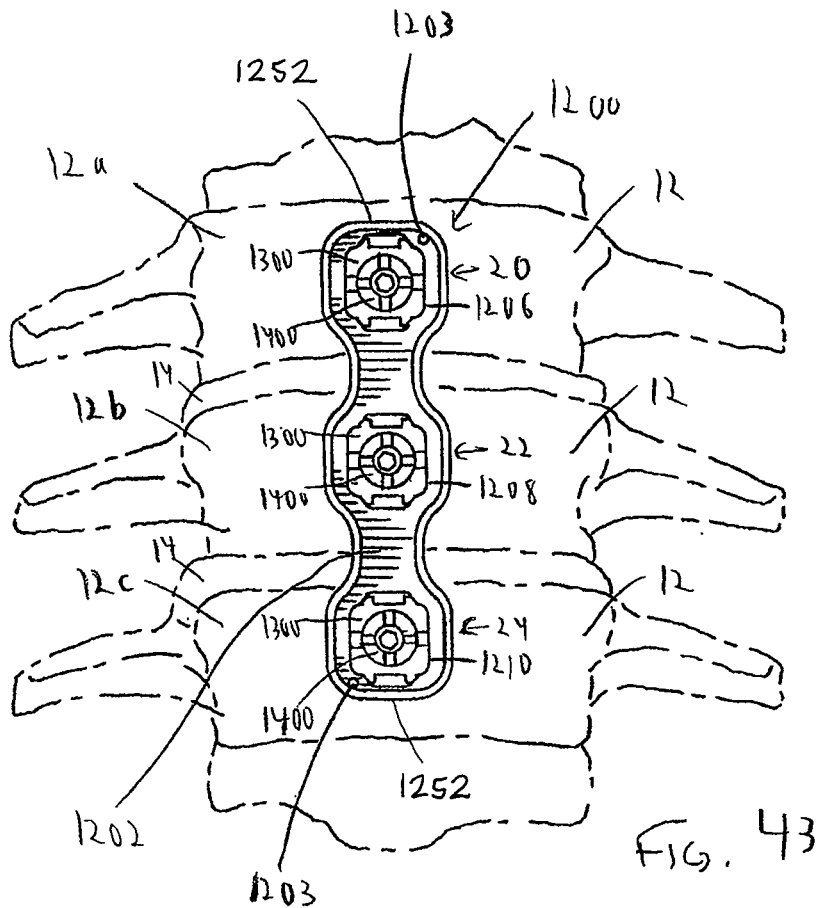
FIG. 43 is a plan view of a standard bone plate system including features in accordance with the present invention and securing vertebrae in a particular orientation.
Figure 44:
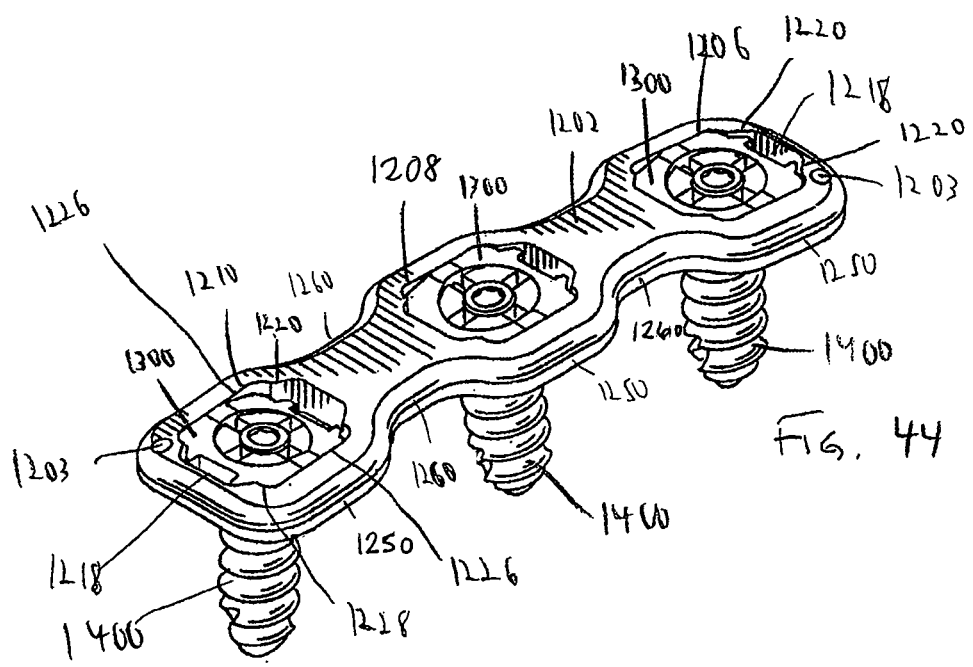
FIG. 44 is a perspective view of the dynamized bone plate system of FIG. 43.

Referring now to FIGS. 43, 44, another embodiment of the present invention is shown in the form of a standard or non-dynamized bone plate system 1200. The bone plate system 1200 is similar in many respects to the dynamic bone plate system 1100 described above, the primary difference being that the present bone plate system 1200 is of the standard or non-dynamized variety. Thus, the present bone plate system 1200 differs from the dynamized bone plate system 1100 in primarily the same way the previously discussed non-dynamized bone plate system 200 differs from the dynamized bone plate system 100.

The bone plate system 1200 features a plate member 1202 with a top face 1204, a bottom face 1214, as well as a pair of generally parallel longitudinal side wall portions 1250 and generally parallel end wall portions 1252, and throughbores 1206, 1208, 1210, all of which are non-dynamized throughbores. Also similar to the previous bone plate 1102, the present plate 1202 features indented regions 1260, floor portions (not shown, but similar to floor portions 1124), end wall portions 1228, and longitudinal sidewall portions 1226 having cavities such as elongated grooves or slot portions (not shown, but similar to slot portions 1130) defined therein, and notched portions (not shown, but similar to notched portions 1140) that are configured to confront the notched portions 1340 of the pivot base 1300. The throughbores 1206, 1208, 1210 further comprise angled walls 1220 which define relief areas 1218, these areas configured to compliment forked projections 1306 and indentation 1308 of the pivot bases 1300. As with the previously discussed dynamic bone plate system 1100, the present bone plate system 1200 employs pivot bases 1300 that do not use retaining members 500, but rather are primarily retained within the throughbores 1206, 1208, 1210 by anchor or pivot pins 1600 that project into the slot portions (not shown) in the plate 1202 and form a tight fit with the apertures 1320 of the pivot bases 1300, allowing the pivot bases 1300 to pivot fore and aft with respect to the longitudinal axis of the plate member 1202. Though the slot portions or elongated grooves (not shown) of the plate 1202 may be elongated, the pivot bases 1300 in the plate 1202 are generally allowed little or no translation by virtue of the end walls 1228 and relief areas 1218, which allow enough clearance to accommodate the pivotal motion of the pivot base 1300 but little space for translation relative to the plate member 1202.

Figure 45:
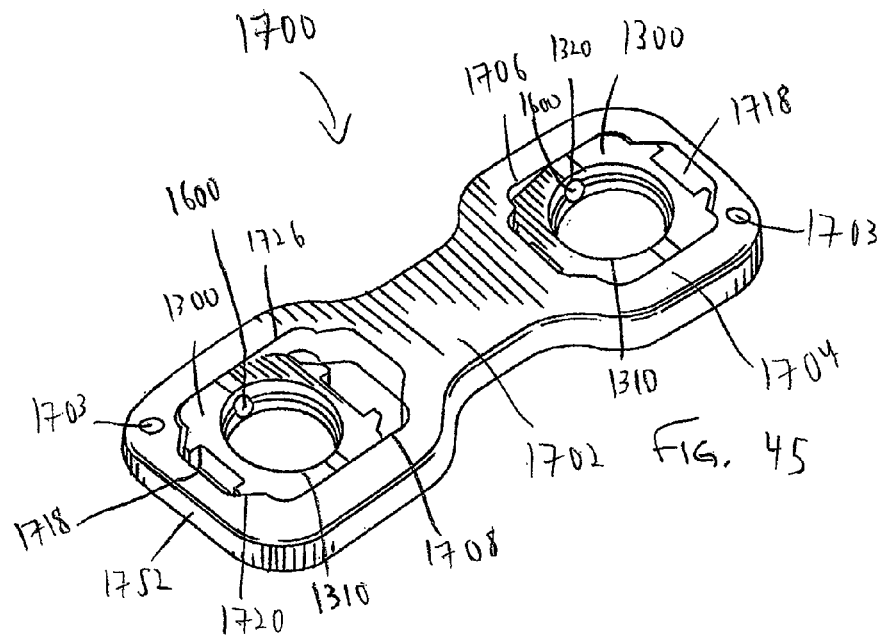
FIG. 45 is perspective view of a dynamized bone plate system including features in accordance with the present invention without the bone anchors.
Figure 46:
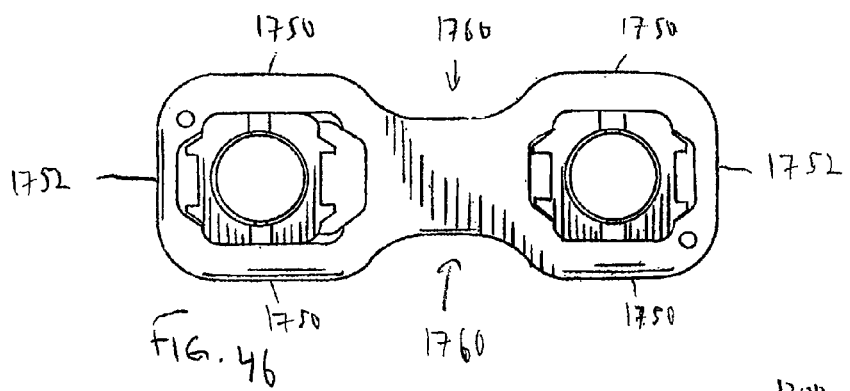
FIG. 46 is a top plan view of the bone plate system of FIG. 45.
Figure 47:
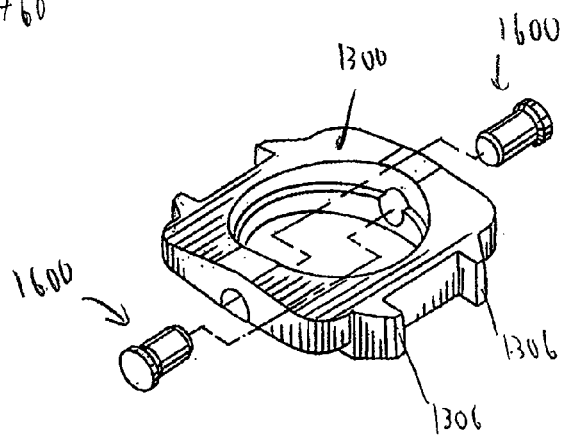
FIG. 47 is an exploded perspective view of the pivot base and pivot members of the dynamized or standard bone plate systems of FIG. 37, 45, or 44.
Figure 51:
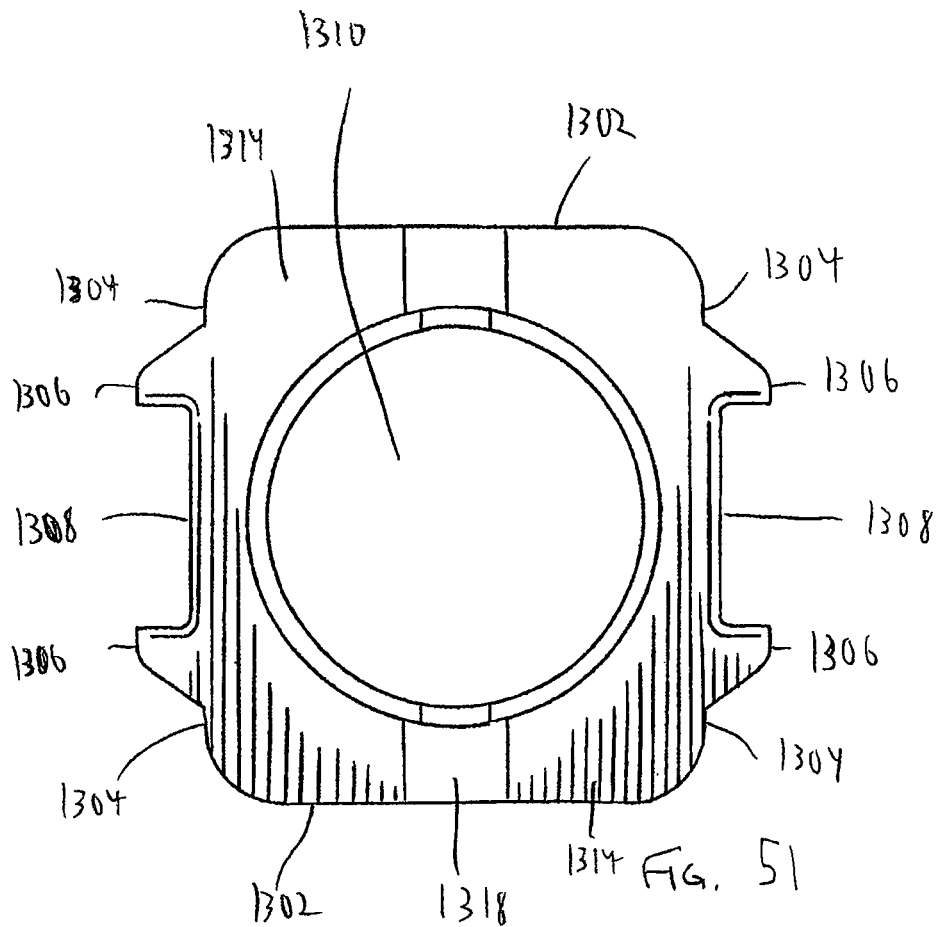
FIG. 51 is a top plan view of the pivot base of FIG. 48.
Figure 52:
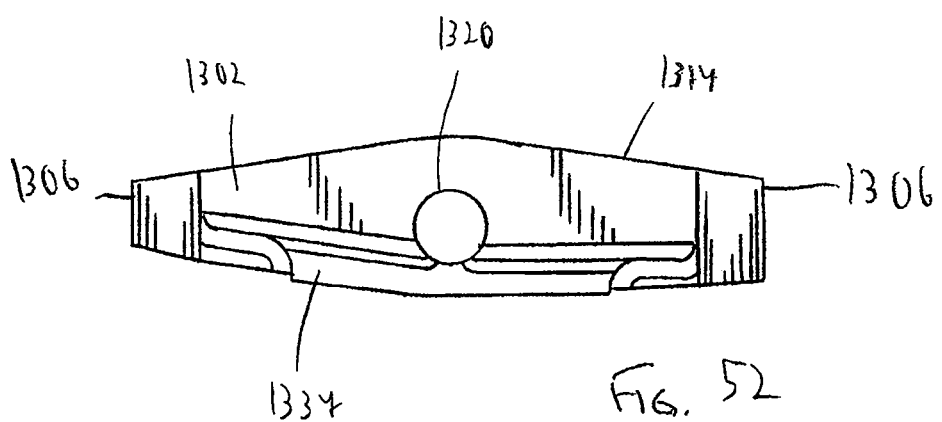
FIG. 52 is a side view of the pivot base of FIG. 49.

Referring now to FIGS. 45, 46, another embodiment according to the present invention is shown in the form of a bone plate system 1700. The present bone plate system 1700 may be referred to as a single-level or two-tiered bone plate system because a plate member 1702 features only one throughbore 1708 in addition to a standard throughbore 1706 that is generally placed over the bone 12 that the surgeon desires to keep stationary. The dynamized or elongated throughbore 1708 would feature the same general dimensions as the dynamized throughbores 108, 1108 of the previously discussed dynamized bone plate systems 100, 1100, which may allow, for example, approximately 1.25 millimeters of translation in addition to a predetermined range of pivoting. The bone plate 1702 also features indented regions 1760 similar to the indented regions 1160, 1260 of the previously discussed bone plates 1102, 1202. In many other aspects, the bone plate system 1700 is generally the same as the previously discussed bone plate system 1100. Though the bone plate system 1700 is shown as a dynamized system, it will be appreciated that the throughbore 1708 may be a standard, non-dynamized throughbore similar to the standard throughbores 1106, 1206, 1208, 1210, 1706 discussed previously.

The materials to be used for the bone plate systems 100, 200, 1100, 1200, 1700 described above must be sufficiently strong and demonstrate desirable mechanical characteristics while also fulfilling other requirements such as biocompatibility and galvanic corrosion considerations. For example, the bone plate members 102, 202, 1102, 1202, 1702 may be composed at least partially of titanium, a titanium alloy, or carbon-fiber polyetheretherketone (PEEK). The pivot bases 300, 1300 and pivot pins 600, 1600 may be composed at least partially of titanium, a titanium alloy, or a cobalt-chrome alloy. The bone anchor members or bone screws 400, 1400; rescue screw 1400'; and locking members or locking screws 1450, 1450' may be composed at least partially of titanium or a titanium alloy. The retaining member or clip 500 may be composed at least partially of either Nitinol (Nickel Titanium Navel Ordnance Laboratory) or Elgiloy, but the retaining member 500 could be composed of any biocompatible material demonstrating a degree of resilience that is suitable for use in the described manner by virtue of the considerations described above. It will, of course, be appreciated that the materials listed herein are listed for exemplary purposes only, and the components described above could be composed of any materials that satisfy the mechanical, chemical, galvanic, and biocompatibility considerations necessary for the present invention.

In another aspect, to determine the proper plate size for a particular patient, a plate sizer such as a sizing caliper or calipers 2000, shown in FIGS. 64-74, may be utilized. In the present embodiment, the sizing calipers 2000 include a pair of legs 2004 adjustably positioned to align with points of interest on the surgical site, such as bone anchor insertion points on one or more vertebrae 12 to determine the proper distance between the bone anchor insertion points and/or the proper length of the plate member required for the patient's anatomy.

The measuring legs 2004 have ball-shaped tips 2008 for being placed on first and second desired location points on vertebrae 12, which may be the locations where bone anchors are to be inserted, other points used in judging proper plate sizes, or other reference points according to the preferences of the surgeon. A pilot hole may be made in a vertebra 12 denoting the desired point of insertion for a bone anchor, and a portion of a ball-shaped end 2008 may be set in place over pilot hole so that the position of one of the measuring legs 2008 is more easily retained in place on the vertebra 12 while using the calipers 2000 to obtain the desired measurement. Though the caliper 2000 is shown with two ball-shaped tips 2008, it will be appreciated that one or both tips could be pointed or sharp reference tips that create a small indentation on the bone 12 as are known in the art.

The sizing caliper 2000 may be adjusted by rotating a knob 2010. This rotation causes one of the measuring legs 2004 to move towards or away from the other measuring leg 2004 positioned at the first desired location point. The ball-shaped tip 2008 is shaped as such so that it may move across the surface of the vertebra 12 or other tissue, for instance, with minimal catching on the surface of the vertebra 12 or other, possibly soft, tissue attached thereto. The position of the free measuring leg 2004 is adjusted until the ball tip 2008 is located at the second desired location point. In a preferred embodiment, the measurement taken by the legs 2004 may be obtained by way of an indicator sleeve 2020 having a plurality of markings such as notches or etchings 2026, shown in FIGS. 71-73. Alternatively, a measurement of the distance between the ends 2008 may be obtained by holding the ends up to a scale, or a plate size may be chosen by comparing the caliper legs 2004 directly to at least one of a bone plate available for use at the time of surgery.

The sizing caliper 2000 includes a housing sleeve 2030 with the knob 2010 and indicator sleeve 2020 located at a proximal end 2032 and the legs 2004 generally secured at a distal end 2034. The legs 2004 are secured together at a pivot point 2040 through which a pin 2042 is inserted to retain the legs 2004 on the body or housing 2030. When the knob 2010 is rotated, the legs 2004 are actuated and the ends 2008 move either farther apart or closer together depending on the direction of knob rotation by pivoting about the pivot point 2040.

Both legs 2004 include a pivot arm 2056 that is outwardly angled in the proximal direction from the rest of the leg 2004 such that force on a terminal end of the pivot arm 2056 causes the legs 2004 to rotate around the pivot point 2040. The respective pivot arms 2056 of the legs 2004 are angled away from each other and, when force is applied to both pivot arms 2056, the legs 2004 pivot in opposite directions. The legs 2004 thus operate in a scissors-like fashion.

To effect such movement with the knob 2010, the pivot arms 2056 are pivotally connected to a central reciprocating member 2060. The knob 2010 is in threaded engagement to a first threaded region 2075 of an advancing shaft 2074, and a shaft-engaging threaded throughbore 2022 of the indicator sleeve 2020 is in threaded engagement with a second threaded region 2076 of the shaft 2074. The position indicator sleeve 2020 is engaged with the threaded region 2076 and further retained in position by a setscrew 2025 that is inserted into a threaded setscrew throughbore 2024 on the indicator sleeve 2020. A third, larger threaded region 2077 is engaged with the housing sleeve 2030.

The advancing shaft 2074 has an extended portion 2097 extending therefrom. The extended portion 2097 defines a plurality of resilient teeth 2098 featuring hook portions 2099. The extended portion 2097 extends at least partially into a pinned shaft 2083 that defines a bore 2085 featuring an inner annular groove 2086. The resilient teeth 2098 are compressed as the extended portion 2097 of the advancing shaft 2074 is inserted into the bore 2085, the teeth 2098 able to expand when the hook portions 2099 enter the annular groove 2086 of the pinned shaft 2083. This configuration locks the advancing shaft 2074 to the pinned shaft 2083 while allowing rotational motion therebetween with respect to one another. In a preferred form, a resilient member 2092 and a bearing member 2093 are disposed between a lower surface 2096 on the advancing shaft 2074 and an upper surface 2084 on the pinned shaft 2083, the bearing member 2093 having an upper surface 2094 and a lower surface 2095. The resilient member 2092 may compensate for possible gaps due to tolerance stack-ups between various components of the measuring calipers 2000, and the bearing member 2093 is intended to enable the advancing shaft 2074 and the pinned shaft 2083 to rotate relative to one another. Also in a preferred form, the resilient member 2092 is disposed between the lower surface 2096 of the advancing shaft 2074 and the upper surface 2094 of the bearing member 2093 while the bearing member 2093 is disposed between the resilient member 2092 and the upper surface 2084 of the pinned shaft 2083, though it will, of course, be appreciated that other configurations are possible.

As the knob 2010 is rotated, the advancing shaft 2074 and indicator sleeve 2020 rotate therewith, rotating relative to the housing 2030 and causing the advancement shaft 2074 and pinned shaft 2083 to translate relative to the housing 2030 and compress the bias member 2082. Thus, rotation of the knob 2010 causes translation of the reciprocating member 2060. Movement of the reciprocating member 2060 in one direction causes the legs 2004 to move towards each other, while movement in the other direction causes the legs 2004 to move apart. The path of the reciprocating member 2060 is defined by the path of motion for the pin 2090 that joins a slot or guide rail 2073 to an aperture 2081 in the drive end 2089 of the pinned shaft 2083 so that the path is generally linear.

During assembly of the calipers 2000, the measuring legs 2004 are spread such that the ball-shaped tips 2008 are a predetermined distance apart from one another. This distance may be, for example, 10 millimeters. At this time, the setscrew 2025 is inserted into the threaded setscrew orifice 2024 of the position indicator sleeve 2020 and driven into firm contact with an unthreaded portion of the advancing shaft 2074 defined between the first and second threaded portions 2075, 2076, thereby acting as a calibration device to properly align the correct relative angular positions of the indicator sleeve 2020 and the advancing shaft 2074 so that the indicator sleeve 2020 will retract to the proper neutral position when the legs 2004 are at their minimally spread position, and furthermore so that the legs 2004 are calibrated to indicate the correct distance between the ball-shaped ends 2008 when the caliper 2000 is used in practice.

The reciprocating member 2060 has a connection end 2061 pivotally attached to proximal ends 2062a of links 2062, which are then pivotally attached at distal ends 2062b to the outwardly angled pivot arms 2056. Being attached to the connection end 2061 and to the outwardly angled pivot arms 2056, the links 2062 are inwardly angled in the proximal direction. As the connection end 2061 moves towards the pivot point 2040 common to both legs 2004 and the distance therebetween is decreased, the links 2062 attached to the connection end 2061 are further spread outward relative to each other. Conversely, when the connection end 2061 is retracted along with the reciprocating member 2060, the links 2062 are drawn together to draw the legs 2004 together.

The reciprocating member 2060 includes a proximal, drive end 2070 having a recess or cavity 2072 for receiving therein a drive end 2089 of the pinned shaft 2083. The cavity 2072 includes a distal wall 2078 generally facing an end surface 2080 of the drive end 2089. A bias or compression member 2082 is located within the cavity 2072 in between the distal wall 2078 and the end surface 2080. When the drive end 2070 is directed in a distal direction, the end surface 2080 of the drive end 2070 applies force to the compression member 2082, which is translated to the distal wall 2078 and, hence, to the reciprocating member 2060. In this manner, advancement of the drive member 2074 and pinned shaft 2083 forces the reciprocating member 2060 to advance, which in turn spreads the legs 2004 towards an open position.

To retract the legs 2004, the drive member 2074 is withdrawn, thereby retracting the reciprocating member 2060. The reciprocating member cavity 2072 is provided with the transversely oriented slot or guide rail 2073 for guiding the motion of the drive member 2074 and pinned shaft member 2083. The drive end 2089 of the pinned shaft 2083 is secured within the cavity 2072 by inserting the pin 2090 through the opening 2073 and through the aperture 2081 of the pinned shaft member 2083. When the drive member 2074 is retracted, the pin 2090 interferes with a rear wall 2071 in the opening 2073 so that the reciprocating member 2060 is also retracted.

The minimally invasive sizing caliper 2000 may be utilized over a span of vertebrae 12 for which the surrounding tissue is not completely removed or resected. The minimally invasive sizing caliper 2000, as well as other instruments, preferably may access the implant site without requiring an opening in the patient as large as the implant site. The sizing caliper 2000 may be directed into the patient opening, and the legs 2004 may then be opened. In addition, the caliper 2000 may be configured to be used in conjunction with a retractor or other instrument to further ensure that the caliper 2000 is minimally invasive.

When the legs 2004 are opened, they are often spread over a distance larger than the patient opening. So that the sizing caliper 2000 may be removed prior to comparing the calipers 2000 to, for instance, the desired distance between throughbores on a plate, the legs 2004 may pivot to be separated by a smaller distance as the caliper 2000 is being withdrawn. Once the legs 2004 are clear of the patient opening, the legs 2004 may return to the position they were in prior to removal and positioned at measuring points. This is achieved by use of the compression member 2082. After the instrument 2000 is removed from the patient, it may be compared directly to the plates of different sizes or may be compared to a scale to determine the required plate size. This is, of course, an optional step as the surgeon could obtain a measurement from the marked or notched indicator sleeve 2020 and choose a plate size accordingly based on the measurement obtained therefrom.

Should the surgeon or clinician choose to measure using the measuring legs 2004 directly (e.g. to double check the measurement obtained from the marked or notched indicator sleeve 2020, to compare the distance directly with available bone plates, or in the case that the indicator sleeve 2020 is absent), the calipers 2000 offer other advantageous features. When the caliper 2000 is withdrawn, the patient's flesh may force the legs 2004 together, or a surgeon may alternatively force them closed to ease removal of the caliper 2000. As can be seen, in order to force the legs 2004 together, the reciprocating member 2060 must retract towards the proximal end of the caliper 2000. The compression member 2082 permits such retraction.

As the legs 2004 are forced together, the reciprocating member 2060 compresses the bias or compression member 2082 against the pinned shaft 2083. The drive member 2074 and pinned shaft 2083 remain stationary so that, once the caliper 2000 is removed and the force applied to the legs 2004 is relieved, the legs 2004 return to the position in which they were when measuring the implant site. An accurate measurement may then be taken from the legs 2004. The enlarged threaded region 2077 of the advancing shaft 2074 would, of course, be configured such that under normal conditions of use, the shaft 2074, knob 2010, and indicator sleeve 2020 are only rotated by the surgeon or clinician and not by the force of the compression member 2082. In this manner, the knob 2010 may be used to alter the compressive force of the compression member 2082 but the alternative arrangement would not hold true.

To advance or retract the drive member 2074 and pinned shaft 2083, the knob 2010 is rotated in one direction or the other, as previously noted. The knob 2010 does not change position relative to the housing sleeve 2030, other than by rotating. The drive member 2074 rotates and advances the pinned shaft 2083 with the pin 2090 being received by the slot or guide rail 2073 of the reciprocating member 2060, which guides the reciprocating member 2060 along the general longitudinal axis of the calipers 2000. As the reciprocating member 2060 is advanced or retracted, and the legs 2004 are opened or closed.

Figure 75:
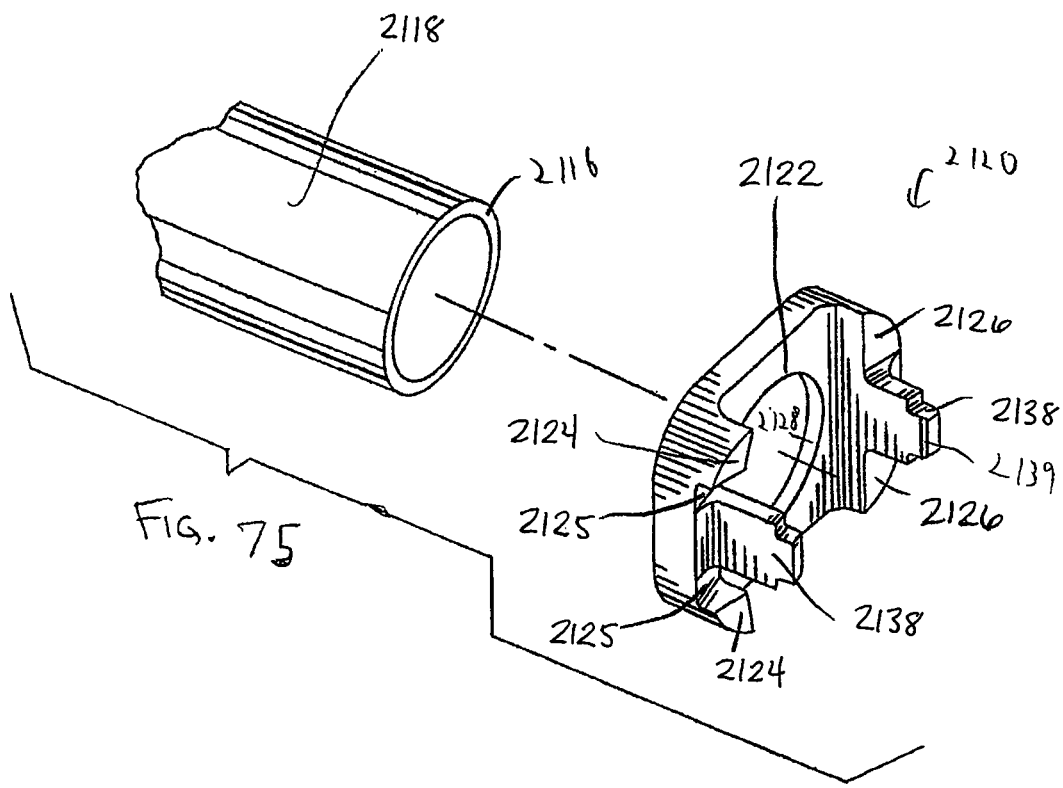
FIG. 75 is a close-up perspective view of a portion of a fixed guide including features in accordance with another aspect of the present invention.
Figure 74:
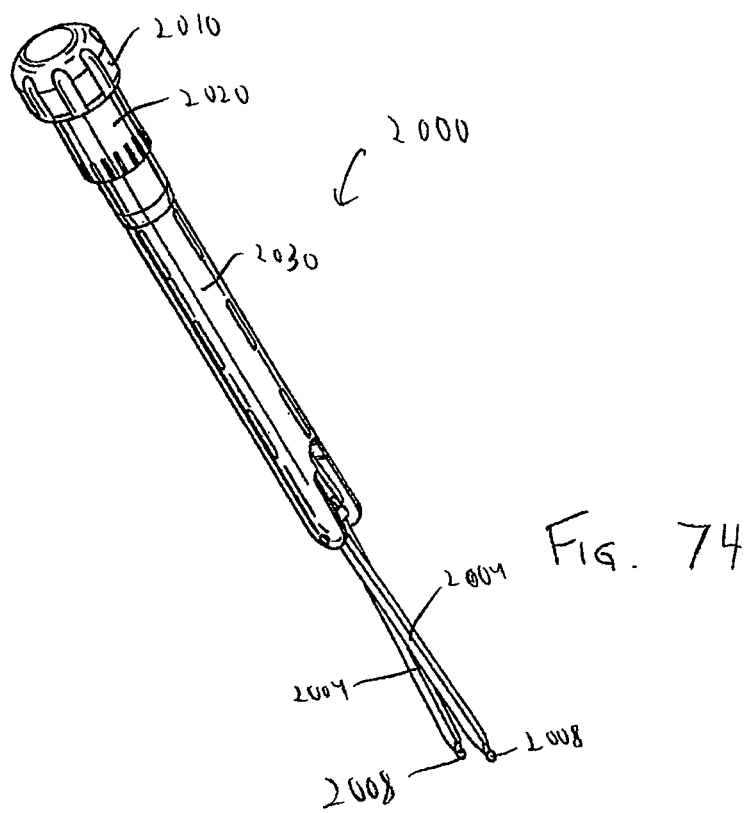
FIG. 74 is a perspective view of the measuring calipers of FIG. 64.
Figure 76:
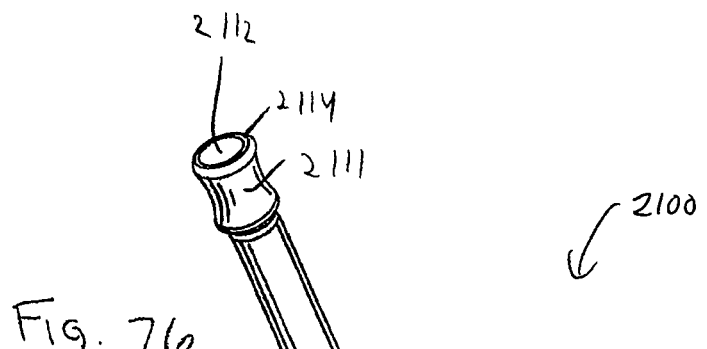
FIG. 76 is a perspective view of the fixed guide of FIG. 75 engaged with a pivot base in the standard bone plate system of FIG. 3.
Figure 77:
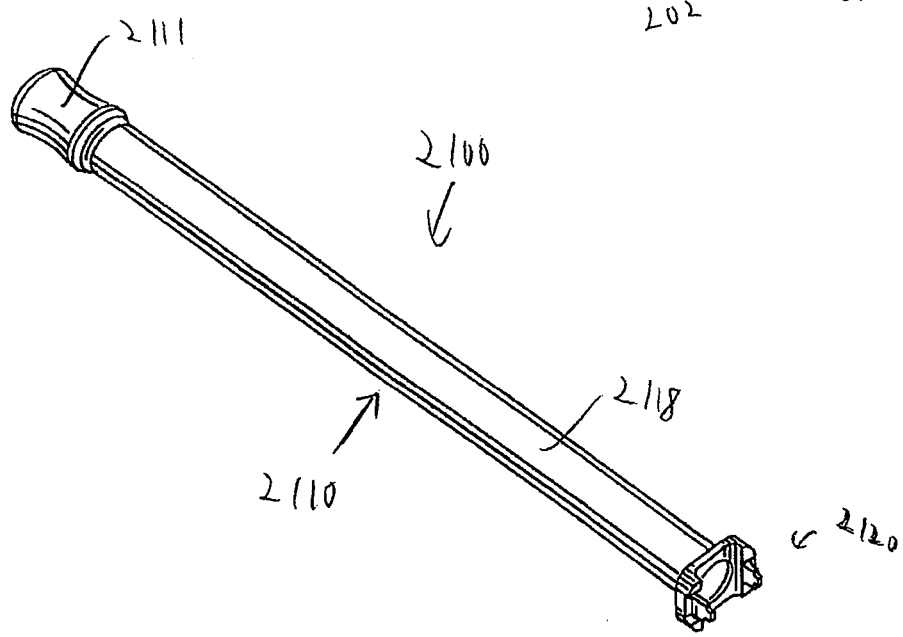
FIG. 77 is a perspective view of the fixed guide of FIG. 76.
Figures 96, 97:
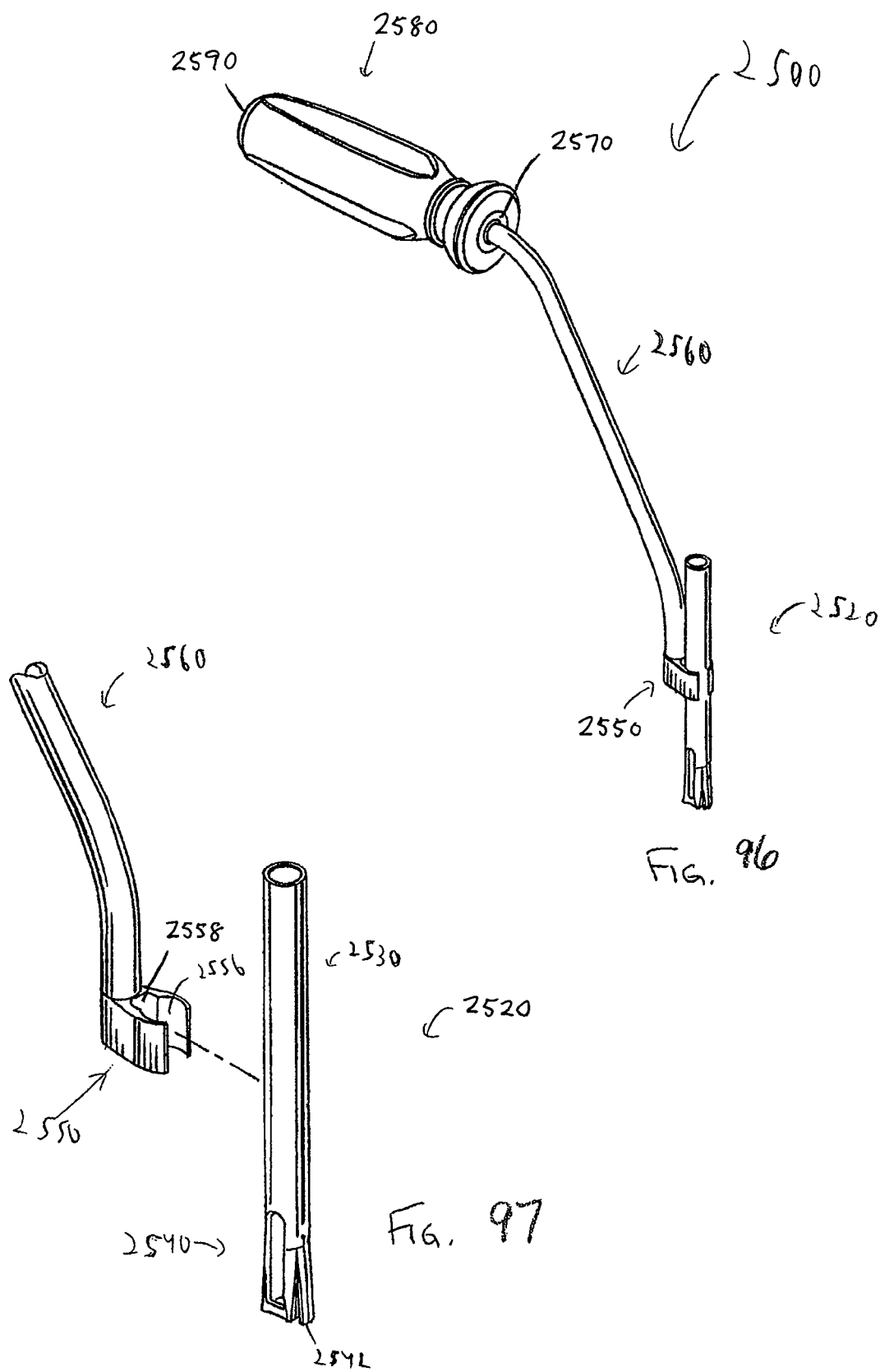
FIG. 96 is a perspective view of a guide including features in accordance with another aspect of the present invention.
FIG. 97 is a partially exploded perspective view of a portion of the guide of FIG. 96.
Figure 9B:
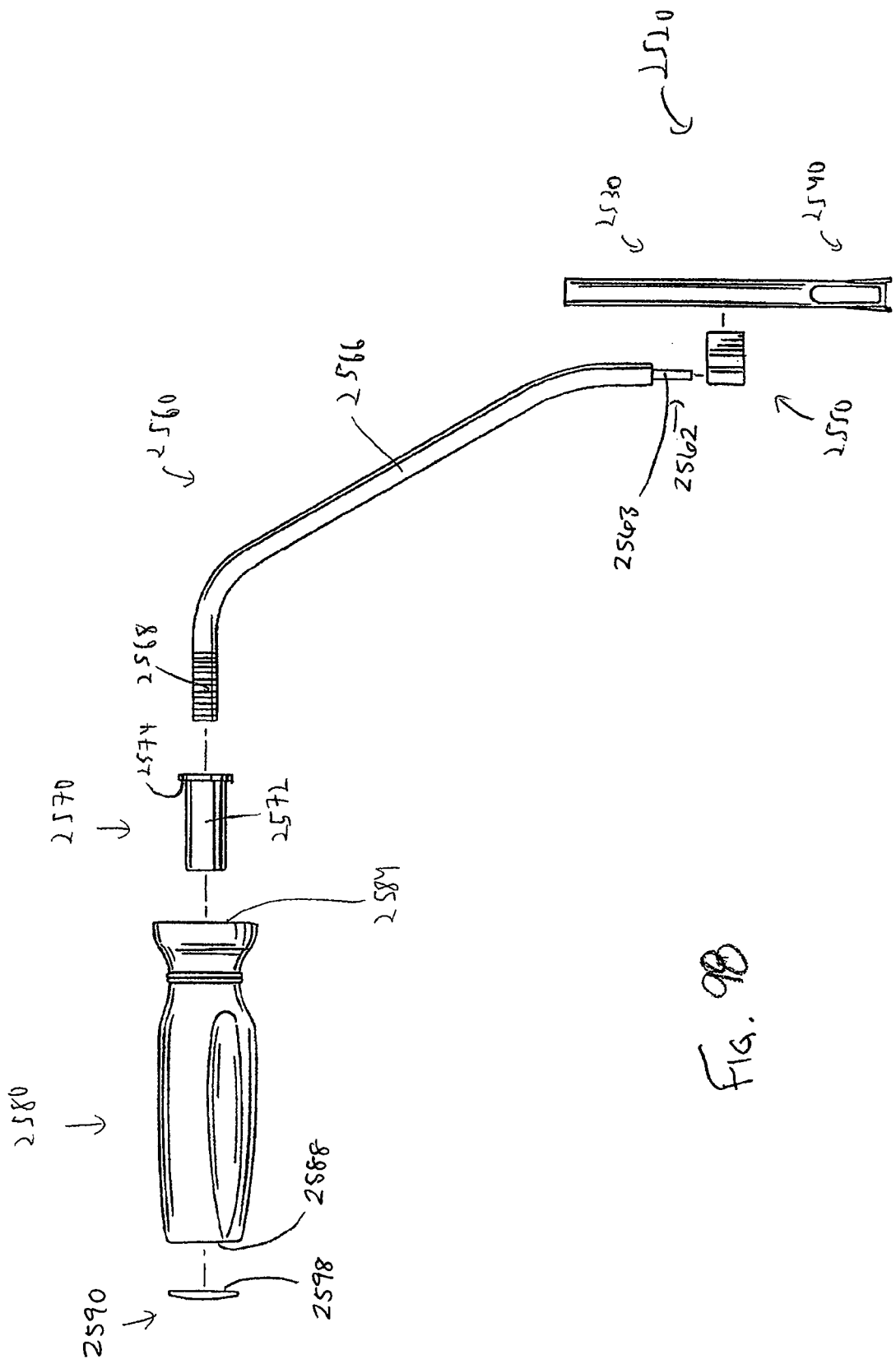

Once the surgeon has chosen the appropriate plate size, a fixed guide 2100, shown in FIGS. 75-77, is configured for use with the bone plate systems 100, 200 that use the pivot bases 300 employing retaining members 500. The fixed guide 2100 comprises a shaft or tube portion 2110 and a base or tip 2120. The tube portion 2110 is generally a hollow cylinder intended to aid a surgeon by guiding at least one of a plurality of tools and instruments during preparation of the surgical site or installation of the bone plate systems 100, 200 that employ retaining members 500. The tube 2110 has an upper portion 2111 which may feature predetermined dimensions to prevent a tool from translating further than a predetermined distance in the direction of the longitudinal axis of the fixed guide 2100. At the top of the upper portion 2111, the tube 2110 has a first end 2114, and the tube 2110 further defines a throughbore 2112 which continues along the longitudinal axis of the tube 2110 to a second end 2116. The base 2120 is configured to have a through hole 2122 which defines an inner surface 2128 that forms a tight fit with an outer surface 2118 of the tube 2110. The tip 2120 further defines at least one of a support leg 2124 and a support shelf 2126, both of which may be angled or curved to complement the convex shape of the top face 314 of the pivot base 300. The tip 2120 features a support shelf 2126 one side and support legs 2124 on the other so that at least one of a slot or gap 2125 may accommodate the retaining member 500 that is secured in place by the bone plate 102, 202, pivot base 300, and pivot members 600. The base 2120 further defines a plurality of teeth 2138 configured to engage the pivot base 300 within the gap 308 between forked projections 306, and a curved portion 2139 to aid the surgeon while aligning the fixed guide 2100 and pivot base 300 for the teeth 2138 to be brought into engagement. Thus, the fixed guide 2100 is not only configured to guide instruments or tools toward the desired position on the surgical site, but the surgeon may also engage a pivot base 300 to either slide the pivot base 300 to the desired location (e.g. in a dynamized throughbore 108, 110), hold the pivot base 300 at a desired angle during the installation of a bone screw 400 to achieve the desired screw trajectory (e.g. in any standard throughbore 106, 206, 208, 210 or dynamized throughbore 108, 110), or both (e.g. in a dynamized throughbore 108, 110). Generally, the uppermost bone screw 400, which is installed within the uppermost throughbore 106, 206 and the lowermost bone screw 400, which is installed within the lowermost throughbore 110, 210 are installed at diverging angles with respect to one another with the center bone screw 400, which is installed within the center throughbore 108, 208 being installed generally perpendicular to the longitudinal axes of the bone plate 102, 202 and the spine. During the recovery period after the bone plate system 100, 200 is installed, the diverging angle of the uppermost and lowermost bone screws 400 becomes less pronounced and the pivot bases 300 facilitate the settling of the spine through pivoting or, in the case of dynamized throughbores 108, 110 pivoting and translating.

When the surgeon has placed the bone plate 102, 202 employing retaining members 500 in the desired position and the bone anchor insertion points are prepared according to the surgeon's preferences (which may mean no preparation whatsoever if self-drilling screws are to be used), the surgeon may then begin to drive in the bone screws 400 using the driver 2200 shown in FIGS. 78-82. The driver 2200 features a shaft 2210 with a transition region 2212 that transitions to a tip or end portion 2220 which, in a preferred form, comprises a hex portion 2222, but it will be appreciated that many bone anchor engagement configurations are possible. The hex portion 2222 has an end surface 2224 and a plurality of grooves 2225, each groove 2225 defining groove walls 2226, a curved leading edge 2227, a generally flat portion 2228, and a curved end 2229. The hex portion 2222 and groove 2225 are configured to accommodate a bone screw retaining spring 2230.

The bone screw retaining spring 2230 comprises a main body 2232 which, when seated, is held generally flush to the end surface 2224 of the shaft tip 2220. With the retaining spring 2230 seated, the body 2232 is permanently joined to the end surface 2224 of the shaft tip portion 2220, such as, for example, by laser welding. The spring 2230 also features a plurality of resilient arms 2234 extending therefrom and configured to be seated within the grooves 2225, the curved leading edge 2227 aiding in seating the arms 2234 within the grooves 2225, and the arms 2234 defining a raised portion 2236 that rises above the profile of the groove walls 2226, as shown in FIG. 81.

In this way, the shape of the driver tip 2220 is configured to be inserted within the center hex aperture 408 of the bone screw 400. Upon entry of the tip 2220 into the aperture 408, the curvature of the curves 2236 is reduced, the ends 2235 of the spring arms 2234 slide further into the grooves 2225 as the curved portions 2236 are depressed, and the retaining spring 2230 aids in creating a tight fit between the driver 2200 and the bone screw 400. Thus, the bone screw 400 is biased to remain attached the driver 2200 prior to installation until the threaded shank 402 is held securely such that the load required to pull the driver tip 2220 out of the aperture 408 is less than the load required to remove the bone screw 400 from the bone 12 or other tissue. In this manner, the surgeon may move the driver 2200 and bone screw 400 together over the surgical site and down the fixed guide 2100 or other guide tube with little risk of the bone screw 400 falling off of the driver 2200. Similarly, the retaining spring 2230 is configured such that an advantageous retainment load is applied to the screw head 404, but the load required to remove the shaft tip 2220 and spring 2230 from the aperture 408 is less than the load required to remove the retaining spring 2230 from the shaft tip 2220 so that the spring 2230 will not become loose or pull out of its seated position during surgery. Preferably, the bone screw 400 is held in engagement by the spring 2230 until the bone screw 400 has been driven past the retaining member 500 and the resilient member 500 has returned at least partially to its original shape and covers at least a portion of the top surface 414 of the bone screw 400. When the bone screw 400 is driven in to the proper depth, the driver tip 2220 and spring 2230 are together removed from the screw aperture 408 and the driver 2200 is cleared of the surgical site.

As shown in FIG. 82, the driver 2200 also comprises a threaded insert 2240, a handle insert 2250, a thrust bearing 2260, a jeweler's knob 2270, a shoulder screw 2280, and a handle cover 2290, forming a handle 2295 assembly for the surgeon to manipulate while driving the bone screw 400. The shaft 2210 defines an upper threaded region 2214 which is threaded into the threaded insert 2240 until an annular wall 2216 of the shaft 2210 abuts to a front surface 2246 of the threaded insert 2240. The threaded insert 2240 forms a fixed connection with the handle insert 2250, and the handle insert 2250 contacts a thrust bearing 2260 that is in fixed connection with a jeweler's knob 2270 by a shoulder screw 2280. The handle insert 2250 and threaded insert 2240 are also in connection with a handle cover 2290, which in a preferred form is ergonomically configured to be controlled by a surgeon's hand. Thus, the handle 2290 and shaft 2210 rotate commonly with one another, but the jeweler's knob 2270 may be held stationary relative to the rotation of the handle 2290 by virtue of the thrust bearing 2260. In this way, the surgeon may hold the knob 2270 in the palm of his hand and rotate the handle 2290 with his fingers. This motion will rotate the handle 2290, insert 2250, threaded insert 2240, and shaft 2210 all in kind, driving the attached screw 400 into the bone 12. As mentioned previously, when the bone screw 400 is seated such that it can be properly retained by the retaining member 500, the screw tip 2220 and spring 2230 are removed from the aperture 408 and the bone screw 400 is then fully installed.

In the case of the bone plate systems 1100, 1200, 1700 that do not employ retaining members 500 to prevent bone screw back out, a guided sleeve 2300, shown in FIGS. 83-90, may be employed to aid the surgeon or clinician in preparing the surgical site prior to installing bone screws 1400.

The guided sleeve 2300 has an end cap 2310 which is threaded to a housing member 2320. The housing member 2320 is generally concentric with and surrounds a portion of a shaft or tube portion 2330, and a base 2340 is interconnected with the lower portion of the guide tube portion 2330. An annular groove 2318 of the cap 2310 houses an o-ring 2350, the housing 2320 is configured to have a bias or compression member 2360 disposed therein within a cavity 2323, and a pin 2370 is connected with and aids in aligning the housing member 2320 and the guide tube 2330.

Looking now to FIG. 87, the cap 2310 defines a throughbore 2312 and a threaded region 2314 which terminates in an end surface 2315. The cap 2310 is threaded into an internal threaded region 2324 of the housing 2320 an annular lip 2316 of the cap contacts a top face 2321 of the housing 2320. The compression member 2360 is seated at a top end 2331 of the tube 2330 and remains in compression between the tube 2330 and the end surface 2315 of the cap 2310, the compression member 2360 being disposed within the cavity 2323 defined by the housing member 2320.

The tube 2330 is held in relationship with the housing member 2320 and is prevented from translating further than a predetermined distance by an annular ledge 2332 on the tube 2330 that contacts an annular lip 2322 of the housing 2320. The ledge 2332 is biased towards the lip by the bias or compression member 2360 that is held in compression within the cavity 2323 between end face 2315 of the cap 2310 and the top face 2331 of the tube 2330. The tube 2330 extends down the longitudinal axis of the guided sleeve 2300 and further defines an insertion portion 2336 at the end that is not generally disposed with within the housing 2320, as shown in FIG. 85. The insertion portion 2336 is configured to form a tight fit with a reception portion 2346 of the base 2340. The base 2340 defines a top face 2348 that abuts to the lip 2338 of the shaft or tube portion 2330, the top face 2348 terminating in a chamfer 2347 that aids in inserting the insertion portion 2336 of the tube member 2330 into the reception portion 2346 of the base 2340.

The base portion 2340 also features pivot base engagement teeth 2342, shown in FIGS. 88, 89, which are configured to engage the pivot base 1300 in the indentation 1308 defined by the forked projections 1306. To aid in this engagement, the base 2340 further defines gaps 2343 to aid as at least a portion of the base 2340 member expands elastically as the teeth 2342 are brought into engagement with the pivot base 1300, the at least a portion of the base 2340 retracting at least partially when fully engaged therewith to form a resilient engagement configuration therebetween. The gaps 2343 terminate in stress mitigation apertures 2344 so that the expansion of the gaps 2343 during engagement will be prevented from creating a stress concentration that is large enough to permanently deform and/or cause failure of at least a portion of the base 2340 as the teeth 2342 are brought into engagement the pivot base 1300. The base 2340 may be contoured or sloped between opposing pairs of teeth 2342, as shown in FIG. 86, to complement the convex curvature of the top face 1314 of the pivot base 1300. Once the base 2340 is fully engaged with the pivot base 1300, the guided sleeve 2300 may be employed to pivot and/or, in the case of dynamized throughbores 1108, 1110, 1708, translate the pivot base 1300 to the desired angle of trajectory and/or longitudinal location wherein the surgeon wishes to insert a bone anchor such as a bone screw 1400 into a bone 12.

The base portion 2340 may also feature at least one of an aperture 2341 to aid in visualizing the bone anchor insertion site on the bone 12. The apertures 2341 may allow the surgeon or clinician to monitor the preparation of the bone anchor insertion site and work with more confidence as the guided sleeve 2300 will not force the surgeon or clinician to prepare the bone anchor insertion site solely by feel. In this way, the preparation tools are advantageously guided, but at least a portion of the bone screw insertion site may be viewed by the surgeon during preparation.

Further, the housing 2320 defines a pin aperture 2324 which features an enlarged upper portion 2326 and a more narrow lower portion 2328, and the tube 2330 defines a slot or guide rail 2334 that is designed to be held in substantial alignment with the pin aperture 2324. A pin 2370, which comprises an enlarged upper segment 2376 and a narrowed lower segment 2378 complements the configuration of the pin aperture 2325 and extends into the slot 2334, as shown in FIGS. 85, 86. Thus, when the guided sleeve 2300 is fully assembled, a load applied to the base 2340 in the direction of the cap 2310 will cause the base 2340 and tube 2330 to translate relative to the housing 2320, sliding the guide rail or slot 2334 relative to the narrowed segment 2378 of the pin 2370 and compressing the bias or compression member 2360 accordingly.

It will, or course, be appreciated that an apparatus employing many of the features of the guided sleeve 2300 could be used with the previously discussed bone plate systems 100, 200 if configured to accommodate the retaining member 500 in a manner similar to the slots 2125 on the base 2120 of the previously discussed fixed guide 2100.

The guided sleeve 2300 is designed to be used with a preparation tool 2400 which comprises a shaft 2410, and the shaft 2410 may end in various tips such as an awl 2430, drill 2440, or tap 2450, as shown in FIGS. 90-95, but it will be appreciated that various other tip configurations are possible. The various possible tips 2430, 2440, 2450 would be available for the surgeon to use, but based on the preference of the surgeon, it is possible that all, none, or any combination of the preparation tips 2430, 2440, 2450 would be employed to prepare the bone anchor insertion site. The awl 2430 may be employed to create a small indentation to aid in forming a later hole, the drill 2440 may be used to form an unthreaded pilot hole, and the tap 2450 may be used to create a threaded hole to aid in the installation of a bone anchor 1400. The tips 2430, 2440, and 2450 may be portions of three separate instruments 2400. Alternatively, the tips 2430, 2440, 2450 could be used with one instrument 2400 in which different shafts 2410, each featuring one variety of tip as shown in FIGS. 93-95, may be disconnected and used with a common handle assembly 2495, or the tips 2430, 2440, 2450 could themselves be interchangeable by being connected to the shaft 2410 in a manner other than being formed as a portion thereof.

The shaft 2410 further comprises an elongate portion 2412, which terminates at an enlarged o-ring engagement portion 2414, the o-ring engagement portion 2414 terminating at a first annular lip 2415 that forms a transition between the o-ring engagement portion 2414 and an enlarged portion 2416. As seen in FIG. 92, the enlarged portion 2416 continues until a second annular lip 2417. Finally, the shaft 2410 features a threaded region 2418, which may be engaged with an internal threaded region 2468 of a bore 2462 in a threaded insert 2460. The shaft 2410 may be threaded into the bore 2462 until an end surface 2467 of the threaded insert 2460 abuts the second annular lip 2417 of the shaft 2410, as shown in FIG. 90.

Referring now to FIGS. 90-92, the threaded insert 2460 is disposed within a first bore 2472 of a handle insert 2470 such that an end surface 2465 of the threaded insert 2460 abuts to an end surface 2475 of the handle insert 2470. The handle insert 2470 is inserted into cavity 2482 in a handle cover 2480 until the end surface 2475 of the handle insert 2470 abuts an inner annular surface 2485 of the handle 2480. The insert 2470 is held securely therein, with an outer surface 2474 being generally concentric to an inner surface 2484, and the assembly is capped by a cap 2490. The cap 2490 features an insertion portion 2492 which is disposed within a second bore 2476 of the handle insert 2470, the insertion portion defining an outer surface 2493 that is generally concentric to and in tight frictional engagement with an inner surface 2478. The cap 2490 is inserted therein until an annular lip 2491 of the cap 2490 abuts an end surface 2481 of the handle cover 2480.

As shown in FIG. 90, the preparation tool 2400 and guided sleeve 2300 are configured so that the two may be used in conjunction with one another. Though the preparation tool 2400 will described largely in terms of use in conjunction with the guided sleeve 2300, it will, or course, be appreciated that at the discretion of the surgeon, the bone anchor insertion site preparation tool 2400 may be used with or without the guided sleeve 2300, and may not be used at all according to the preferences of the surgeon or clinician.

To prepare a bone anchor insertion site, the shaft 2410 of the preparation tool 2400 is inserted through the throughbore 2312 of the end cap 2310 of the guided sleeve 2300 so that the o-ring engagement portion 2414 of the shaft 2410 is brought into contact with an inner diameter surface 2354 of the o-ring 2350 and may continue to be inserted until the contact surface 2415 abuts a top surface 2311 of the cap 2310, as indicated in FIG. 90. At this point, further downward translation of the tool 2400 will push the cap 2310 and housing 2320 down along with the instrument 2400, all translating relative to the tube 2330 and base 2340 with alignment being retained by the pin 2370 that is generally in alignment with and guided by the slot 2334.

It should be noted that the configuration described above allows the instrument 2400 to be brought into engagement with the guided sleeve 2300 whether the guided sleeve 2300 is free of the pivot base 1300 or fully engaged therewith. If the tool 2400 is inserted into the guided sleeve 2300 when the base 2340 portion is free of the pivot base 1300, the surfaces

2415, 2311 may be abutted and the instrument 2400 will be biased away from the bone surface while the base 2340 engages the pivot base 1300. Furthermore, the o-ring 2350 and the o-ring engagement portion 2414 of the shaft 2410 may be configured to form a tight fit such that the guided sleeve 2300 will not easily be jostled and/or slide off of the tool 2400 when the guided sleeve 2300 and tool 2400 engaged therewith are moved over the surgical site to be brought into engagement with the pivot base 1300.

If the tool 2400 is inserted into the guided sleeve 2300 while the base 2340 is already engaged with the pivot base 1300, the tip 2430, 2440, 2450 will contact the bone 12 and the shaft or tube portion 2330 of the guided sleeve 2300 will begin to translate such that a progressively greater portion of the tube 2330 retracts into the housing 2320, causing the o-ring engagement portion 2414 to slide further through the o-ring 2350 and further compressing the bias member 2360 in kind. Once the o-ring engagement portion 2414 is positioned and the surfaces 2415 and 2311 abut, the load may be removed and the tool 2400 and guided sleeve 2300 will revert to their neutral, upwardly biased positions as shown in FIGS. 85, 90. In this manner, the tool 2400 is biased away from the bone anchor insertion site when the surgeon is not applying an affirmative load toward the bone 12.

Looking now to FIGS. 96-107, a guide 2500 may also be available for use with the bone plate systems 1100, 1200, 1700 that do not employ a retaining member 500. The guide 2500 may be used with the preparation tool 2400, but differs from the guided sleeve 2300 because the guide 2500 may also be used to guide a bone anchor such as a bone screw 1400 attached to the driver 2600 toward a bone anchor insertion site. The guide 2500 features a guide tube 2520 with an upper shaft or tube portion 2530 and a lower pivot base engaging or base portion 2540. The base portion 2540 is similar in many respects to the base 2340 of the guided sleeve 2300, but, in a preferred form, the tube portion 2530 and base portion 2540 are formed as one unit, not two adjoining units as depicted in a preferred form of the tube portion 2330 and base portions 2340 of the guided sleeve 2300 shown in FIG. 85. The base portion 2540 features apertures 2541, pivot base engagement teeth 2542 with gaps 2543 and stress mitigation apertures 2544.

The guide 2500 may also feature a coupling member 2550, a connection portion or arm 2560, a threaded insert 2570, a handle 2580, and a cap 2590, all seen in FIG. 98. This arrangement allows the surgeon or clinician to engage and actuate the pivot base 1300 while causing only limited obstruction of the view of the surgical site. In using the guide 2500, the surgeon may grip the offset handle 2580 and move the guide 2500 therewith. The handle 2580 features a first end 2588 which is abutted to an end surface 2598 of the cap 2590. The handle 2580 also features a second end 2584 that defines a bore 2582 into which a threaded insert 2570 is inserted, abutting an annular surface 2574 of the threaded insert 2570 and the second end surface 2584 of the handle 2580, and the bore 2582 engaged with an outer surface 2572 of the insert 2570. The insert 2570 further defines an internally threaded bore 2578 which is in threaded engagement with a threaded portion 2568 of the connection arm 2560. The arm 2560 further features an elongate portion 2566 which extends between the handle 2580 and the guide tube 2520. The connection arm 2560 terminates in an insertion portion 2562, which features an outer surface 2563, the insertion portion 2562 configured to connect the elongate member 2560 to the coupling member 2550.

Figure 101:
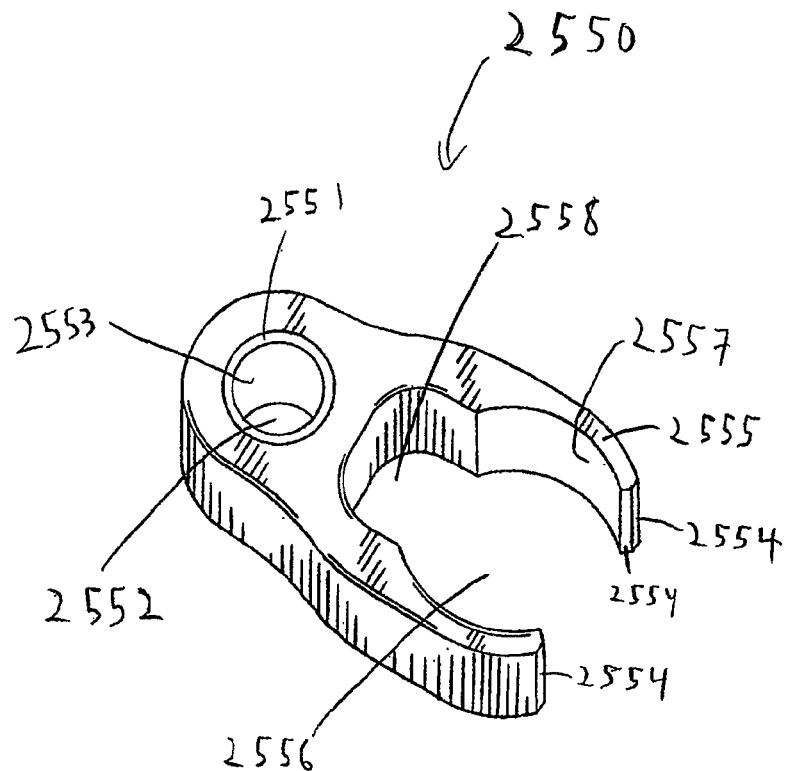
FIG. 101 is perspective view of the coupling member of the guide of FIG. 96.
Figure 102:
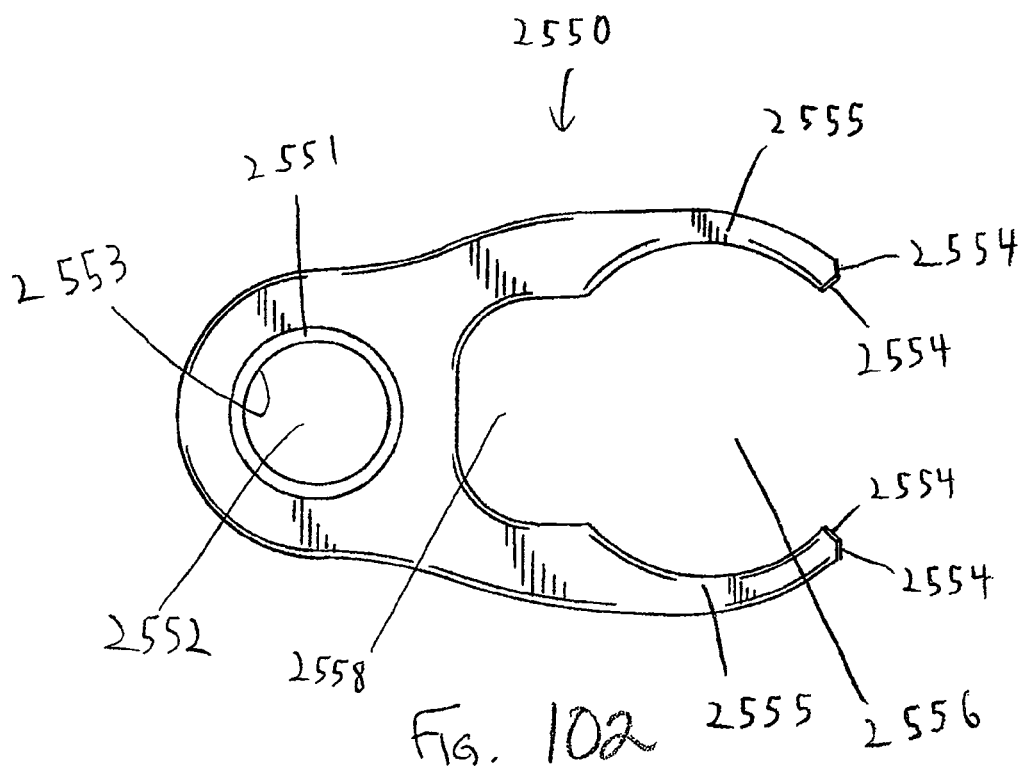
FIG. 102 is a top plan view of the coupling member of FIG. 101.
Figure 106:
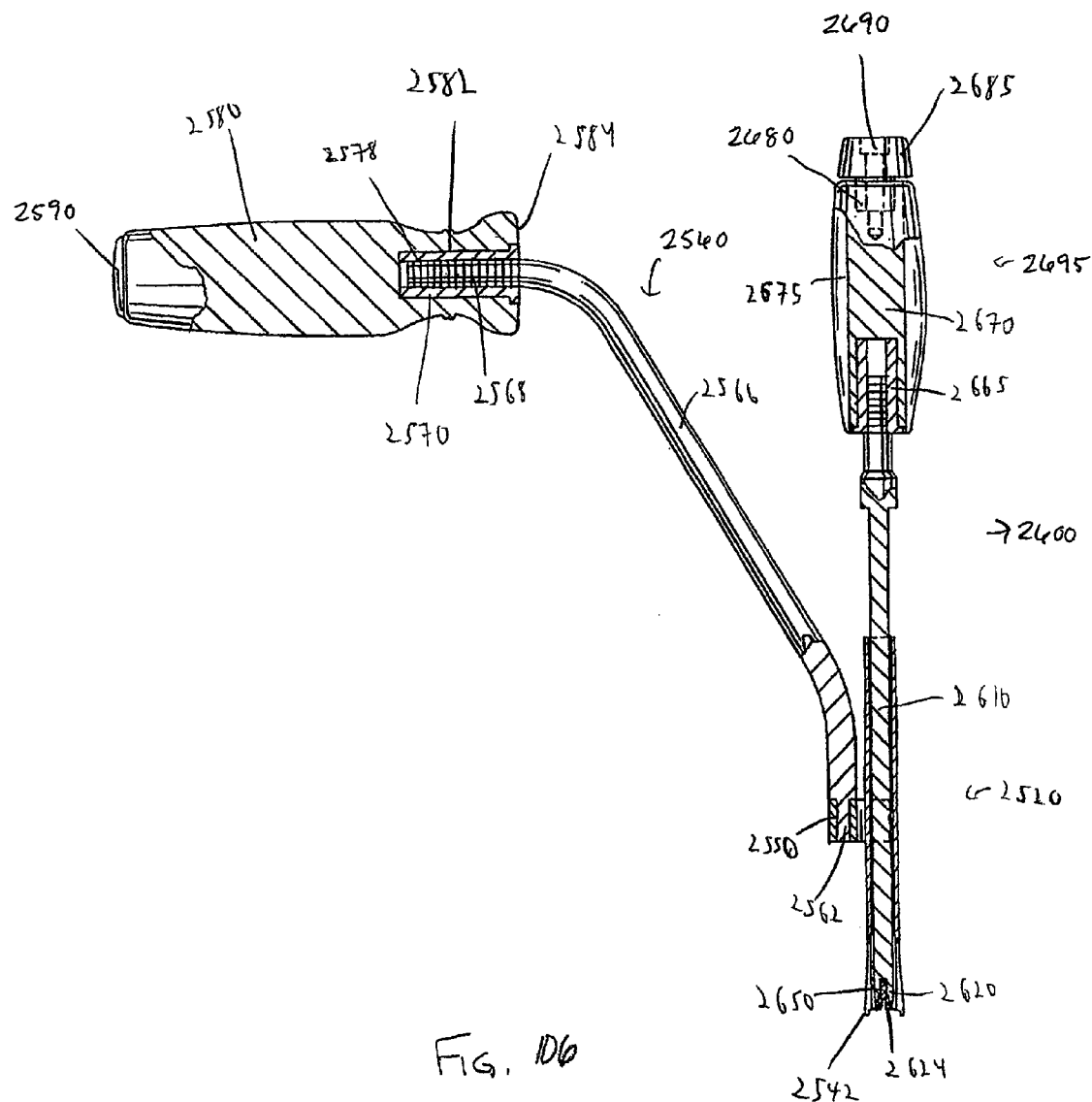
FIG. 106 is a cross-sectional side view of the guide of FIG. 96 engaged with a bone anchor driver including features in accordance with another aspect of the present invention, the driver configured to drive the bone screws of FIGS. 58 and 61.
Figure 107:
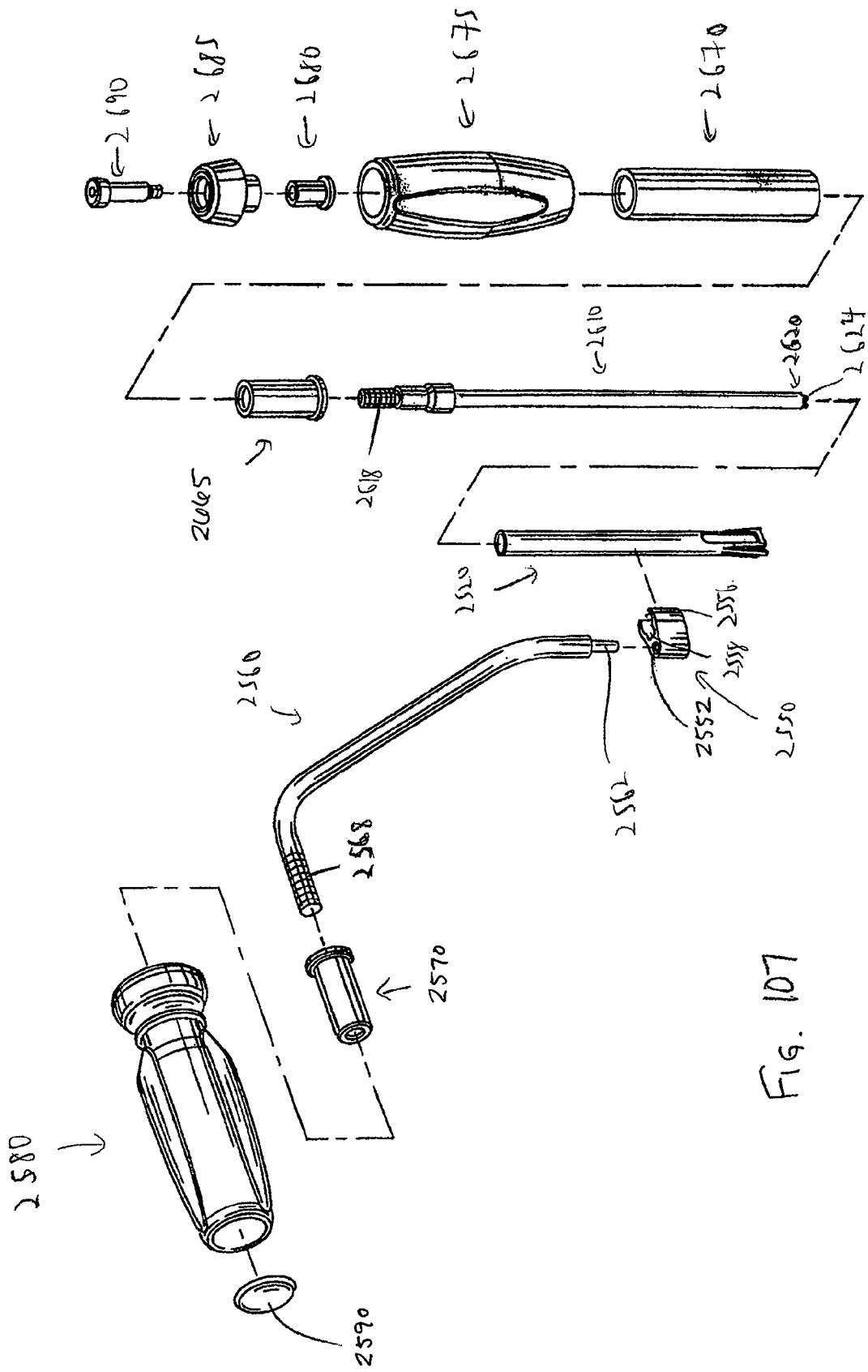
FIG. 107 is an exploded perspective view of the guide and driver of FIG. 106

The coupling member 2550 couples the guide tube 2520 to the elongate member 2560, thereby allowing the surgeon to use the handle 2580 to actuate the guide tube 2520 and therefore control the pivot base 1300 while the base portion 2540 is in engagement therewith. As seen in FIGS. 101, 102, the coupling member 2550 features a chamfer 2551 at the upper portion of a throughbore 2552, which defines an inner surface 2553. The chamfer 2551 aids when inserting the insertion portion 2562 of the elongate member 2560. The insertion portion 2562 slides into the throughbore 2552, creating a connection between the inner surface 2553 of the throughbore 2552 and the outer surface 2563 of the insertion portion 2562. With the insertion portion 2562 seated therein, the insertion portion 2562 of the elongate member 2560 is permanently bonded to the coupling member, such as, for example, by laser welding. Further, the coupling member 2550 defines chamfers 2554 on curved arm portions 2555, the curved arm portions 2555 defining a tube retainment cavity 2556 and retainment surfaces 2557. As shown in FIG. 102, next to the cavity 2556, a generally U-shaped window portion or aperture 2558 is defined. In a preferred form, the shaft or tube portion 2530 of the guide tube 2520 is brought into substantial alignment with the cavity 2556 with the chamfers 2554 aiding in guiding the tube 2520 into position. The tube portion 2530 is then permanently bonded to the coupling member 2550, such as, for example, by a laser welding bonding the retainment surfaces 2557 of the arm portions 2555 to an outer surface 2557 of the tube portion 2530.

The configuration described above, depicted in FIG. 103, offers a guide apparatus with the novel feature that the aperture 2558 offers a partial view of the pivot base 1300 and engagement teeth 2542, which may be very helpful when aligning the engagement teeth 2542 to the impression 1308 defined by the forked projections 1306 of the pivot base 1300. If the aperture 2558 were not present during engagement of the pivot base 1300, the guide 2500 would be more difficult to align properly and any difficulty in this regard may prolong the time it takes to complete the surgical operation wherein the bone plate 1100, 1200, 1700 is installed.

Also similar to the guided sleeve 2300, the guide 2500 may be used to pivot and, in the case of dynamized throughbores 1108, 1110, 1708, translate the pivot bases 1300. It will, of course, be appreciated that an apparatus employing many of the features of the guide 2500 could be used with the previously discussed bone plate systems 100, 200 if configured to accommodate the retaining member 500 in a manner similar to the slots 2125 on the base 2120 of the fixed guide 2100.

While the preparation instrument 2400 may be used with the guided sleeve 2300 or the guide 2500, the guide 2500 is also configured to be used in conjunction with the driver 2600 seen in FIGS. 106-111. The driver 2600 has a handle assembly portion 2695 with a shoulder screw 2690, a jeweler's knob 2685, a thrust bearing 2680, a handle cover portion 2675, a handle insert 2670, and a threaded insert 2665. In this way, the present driver 2600 employs much the same general handle configuration as the previously described driver 2200 that is intended to be used with the bone plate systems 100, 200 employing retaining members 500, in which the jeweler's knob 2685 is held in the palm of the surgeon's hand and is linked to the remainder of the handle assembly 2695 by a thrust bearing 2680, which allows the surgeon to drive the bone screw 1400 by rotating the handle cover 2675 with his fingertips and therefore rotating a handle insert 2670, threaded insert 2665, and shaft 2610 all in kind with a threaded portion 2618 of the shaft 2610 connecting the shaft 2610 to the handle assembly 2695. The present driver 2600, however, retains the bone anchor 1400 to the driver 2600 in a different, however still resilient manner and accounts for the locking member 1450 of the back out prevention method of the bone screw 1400.

The shaft 2610 of the driver 2600 features an outer surface 2612 and an end portion or tip 2620. The shaft 2610 of the driver 2600 and a bone screw 1400 may be directed down a throughbore 2522 of the guide 2500 and thereby be directed to the correct configuration in terms of location and angle of trajectory with respect to the pivot base 1300 and the desired bone anchor insertion site on the vertebra 12.

Figure 10:
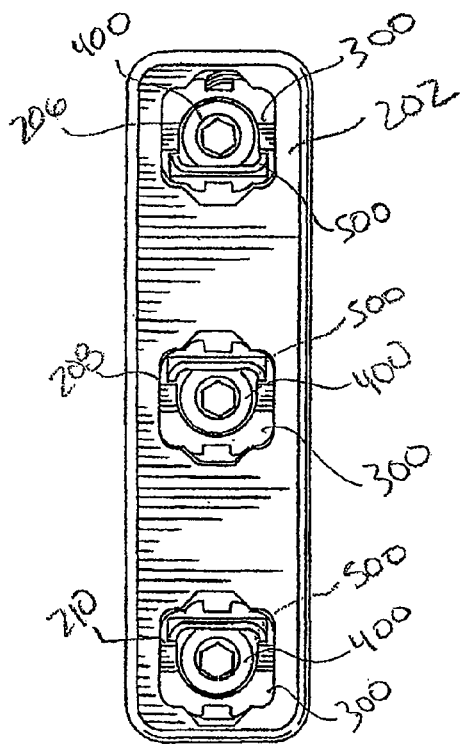
FIG. 10 is a top plan view of the standard bone plate system of FIG. 8.
Figure 12:
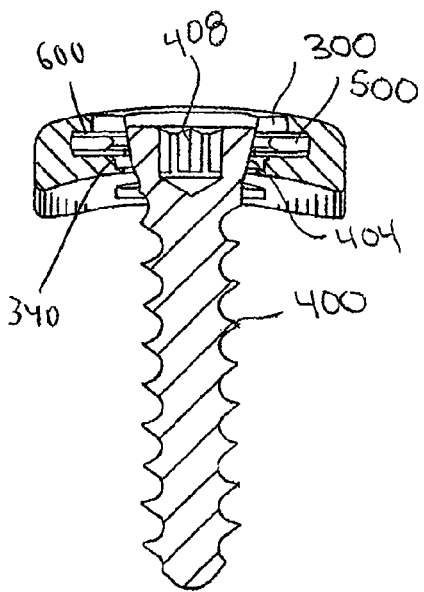
FIG. 12 is a cross-sectional end view of the dynamized or standard bone plate systems of FIG. 2 or 8.
Figure 11:
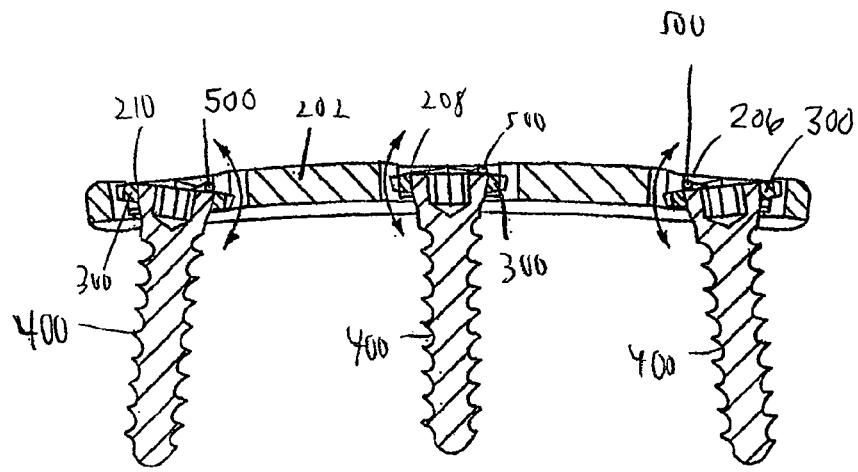
FIG. 11 is a cross-sectional side view of the standard bone plate system of FIG. 8 taken along 11-11 thereof.
Figure 13:
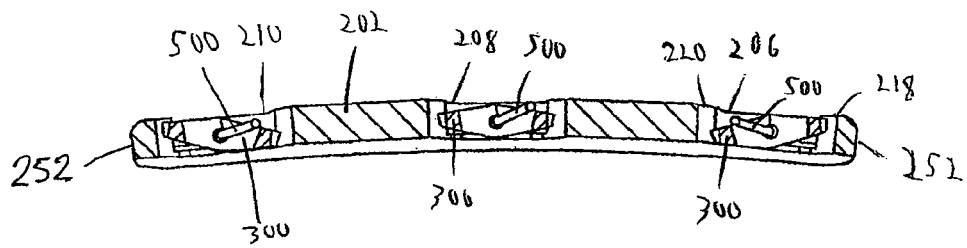
FIG. 13 is a cross-sectional side view of the standard bone plate system of FIG. 9 taken along line 13-13 thereof.

Furthermore, the tip portion 2620 of the driver 2600 features a plurality of bone anchor engagement projections 2624 that are configured to fit within the driver engagement slots 1430 in the screw head 1404. The driver 2600 further comprises a chamfer 2621 which leads into a bore 2622, as seen in FIG. 111. The bore 2622 is designed to house an insert 2650, the insert 2650 also defining a chamfer 2651 in addition to an enlarged portion 2652. The insert 2650 further features an elongate portion 2656, a second enlarged portion 2657 which terminates in a lower surface 2654, and, in a preferred form, the insert 2650 features a plurality of resilient teeth 2658 each having a sloped or curved portion 2659. The insert 2650 may be inserted into the bore 2622 of the tip portion 2620, as shown in FIG. 10, with the enlarged portion 2652 of the insert 2650 creating a tight fictional or, alternatively, threaded engagement with the bore 2622.

Upon initial engagement with the bone anchor 1400, the engagement projections 2624 slide into the engagement slots 1430, and the resilient teeth 2658 of the insert 2650 slide into the hex aperture 1458 of the locking screw 1450 and are compressed, creating an outward hoop stress and thereby retaining the locking screw 1450 to the driver 2600. The curved portions 2659 of the resilient teeth 2658 aid in aligning the insert 2650 to the hex aperture 1458, as indicated in FIG. 112. The driver 2600 is brought into full engagement with the bone anchor 1400 either when a bottom surface 2614 of the shaft 2610 contacts the top surface 1414 of the screw head 1404, or alternatively when end surfaces 2625 of the engagement projections 2624 contact bottom surfaces 1431 of the engagement slots 1430. This configuration allows the surgeon to move the screw 1400 and driver 2600 over the surgical site and down the guide tube 2520 with the screw 1400 being unlikely to loosen and become free of the driver 2600. This engagement configuration also allows the driver 2600 to drive the bone screw 1400 while keeping the locking screw 1450 proud. After the bone screw 1400 is driven to the desired depth, the driver 2600 is pulled out of engagement with the screw 1400, removing the engagement projections 2624 from the engagement slots 1430 and the resilient teeth 2658 from the hex aperture 1458 of the locking member 1450. The insert 2650 is configured such that the load required to remove the resilient teeth 2658 from the hex aperture 1458 is less than the load required to remove the insert 2650 from the bore 2622, and thus the insert 2650 will not become loose or remain in engagement with the locking screw 1450 as the driver 2600 is pulled away from the bone screw 1400 after the bone anchor 1400 has been driven into bone 12 and the head portion 1404 has been seated within the opening 1310 of a pivot base 1300.

When the screw 1400 has been driven into the bone 12, the locking screw 1450 may be seated by a hex driver (not shown), which may be similar in form to the hex driver 2200 but configured and sized to engage the hex aperture 1458 of the locking screw 1450. When the locking member 1450 is properly seated, the resilient screw head 1404 will be expanded and a hoop stress will be applied to the annular walls of the opening 1310 in the pivot base 1300, serving to retain the screw head 1404 therein and inhibit bone anchor back out.

As previously indicated, the rescue screw 1400' configured for use with the bone plate systems 1100, 1200, 1700 that do not employ retaining members 500 may be configured to be driven by the present driver 2600, as well.

Figure 116:
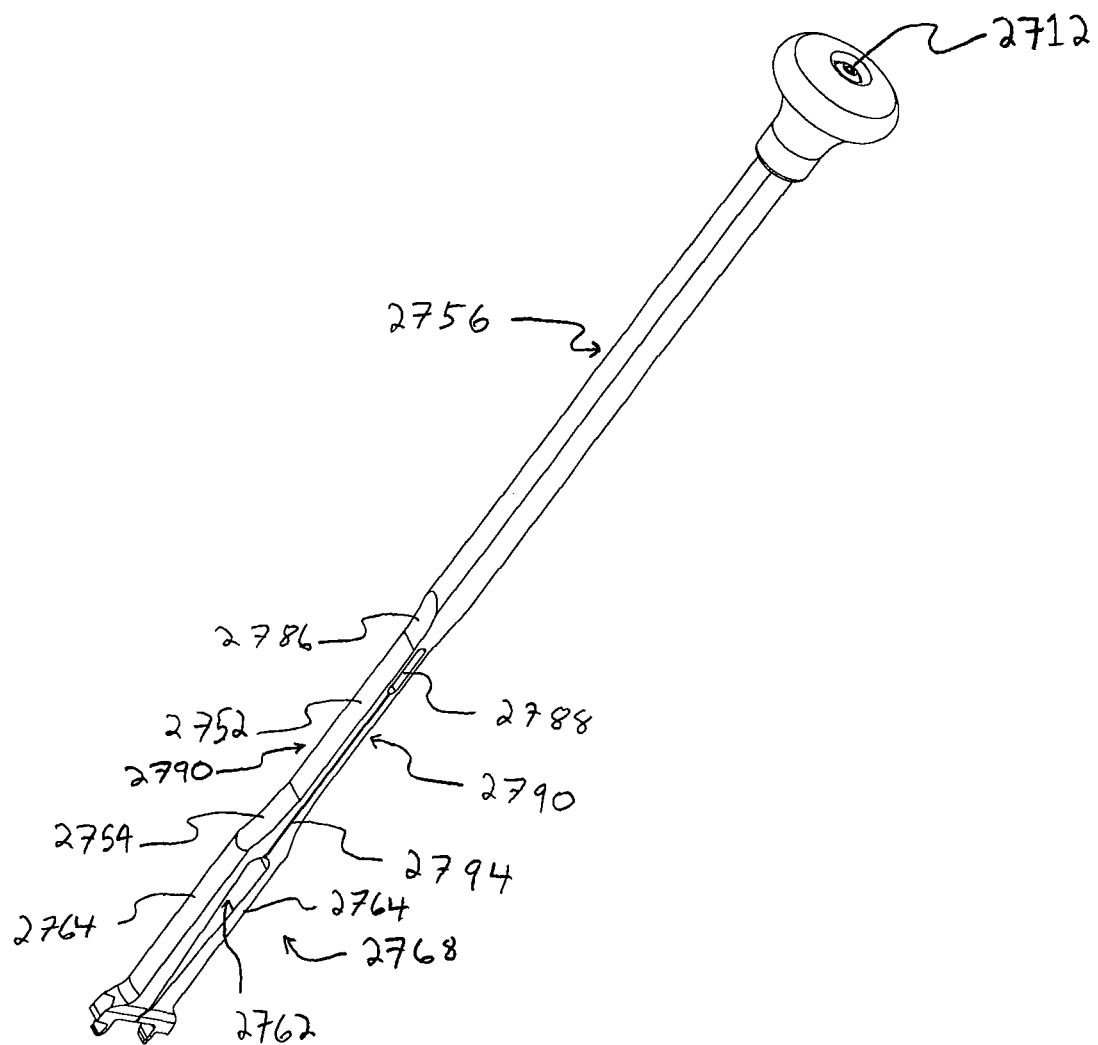
FIG. 116 is a perspective view of the clamping mechanism of the plate holder of FIG. 113.
Figure 117:
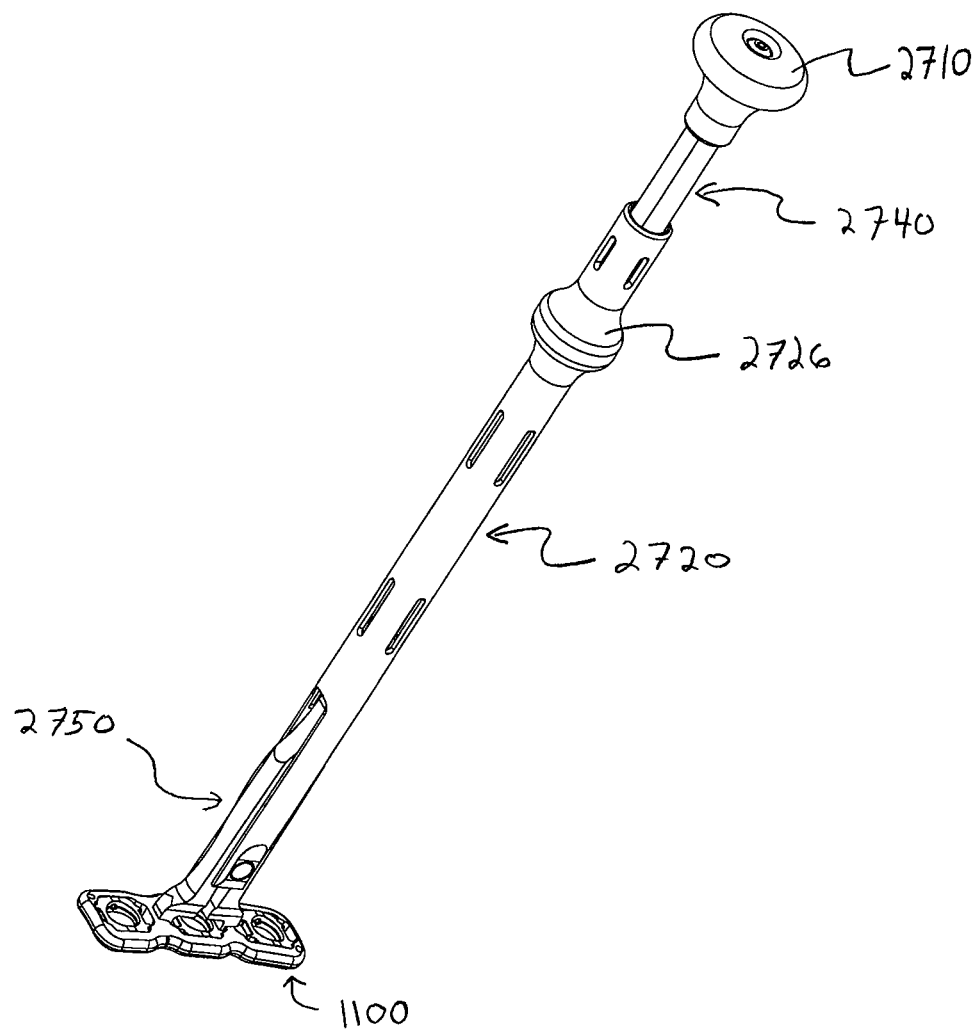
FIG. 117 is a perspective view of the plate holder of FIG. 113 engaged with the bone plate system of FIG. 39.
Figure 118:
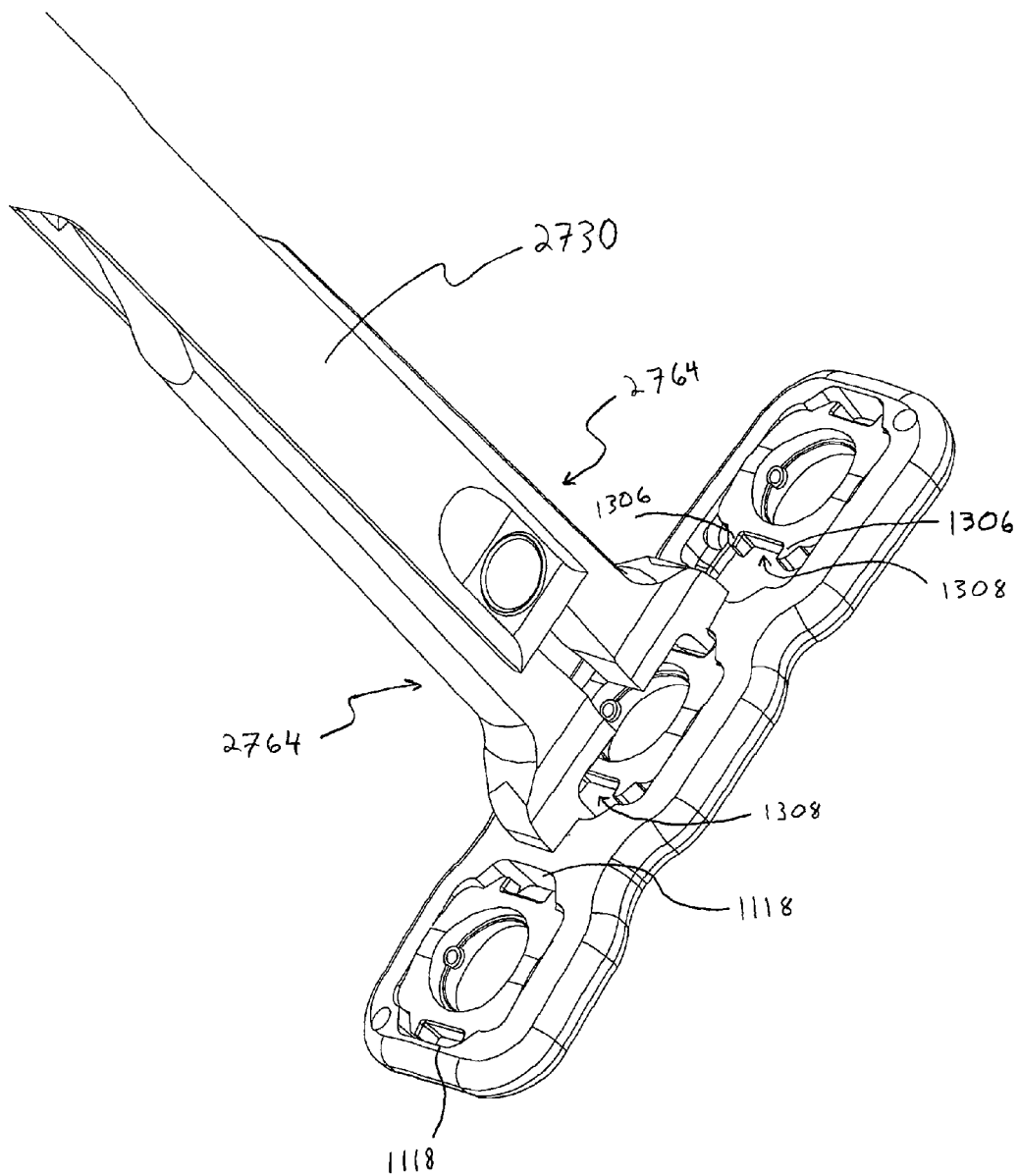
FIG. 118 is a close-up perspective view of the plate holder and bone plate system of FIG. 117.
Figure 119:
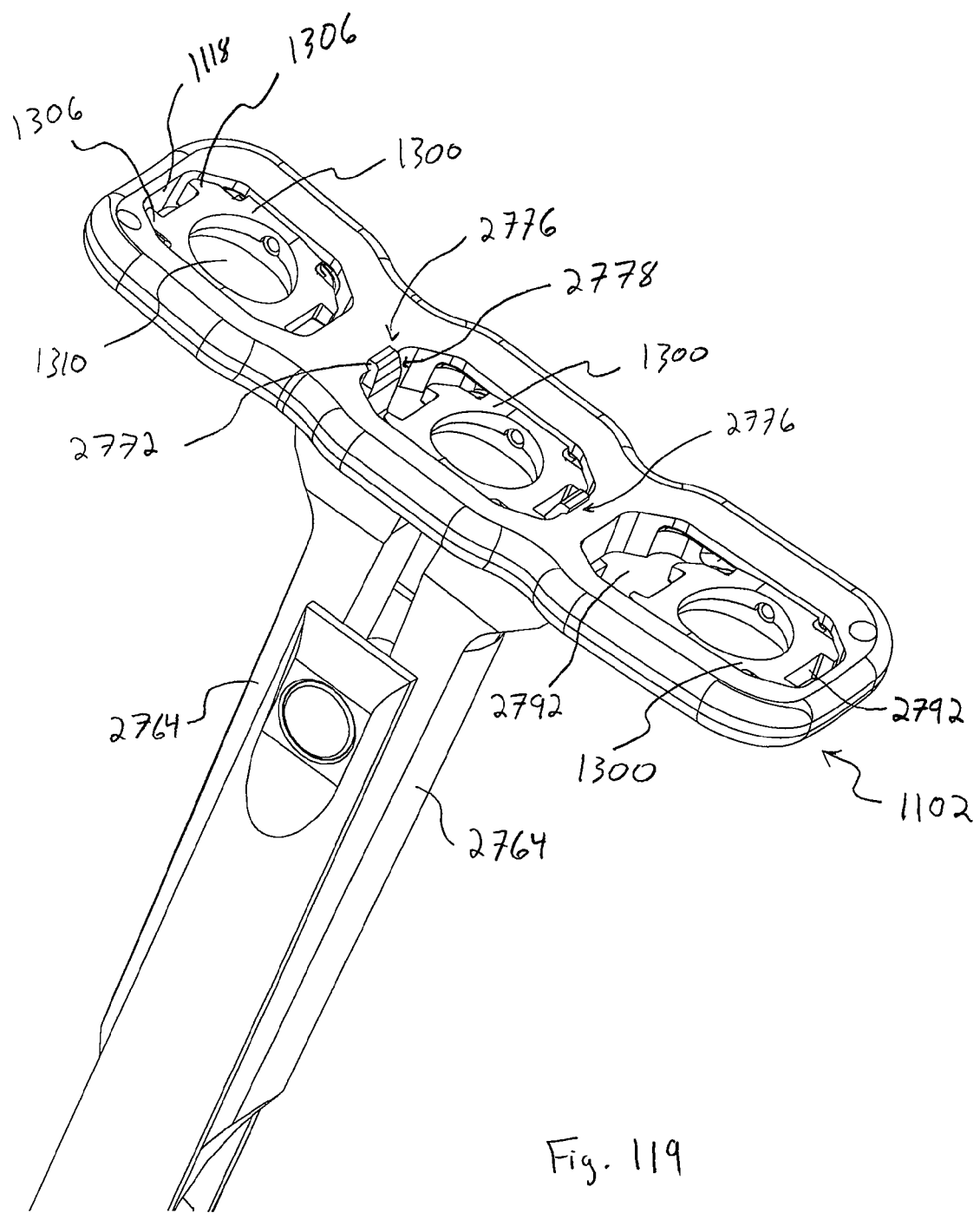
FIG. 119 is a close-up perspective view of the plate holder and bone plate system of FIG. 117.

Turning to FIGS. 113-119, a surgeon may use a plate holder 2700 to position bone plate systems 100, 200 that use pivot bases 300, as well as bone plate systems 1100, 1200, 1700 that use pivot bases 1300. The plate holder 2700 engages a bone plate and allows the surgeon to maneuver the bone plate into the desired position along the vertebrae before the bone plate is secured thereto. FIGS. 117-119 show plate holder 2700 engaging bone plate system 1100, but this configuration is provided as merely an example and should not be considered limited to this bone plate system.

Figure 114:
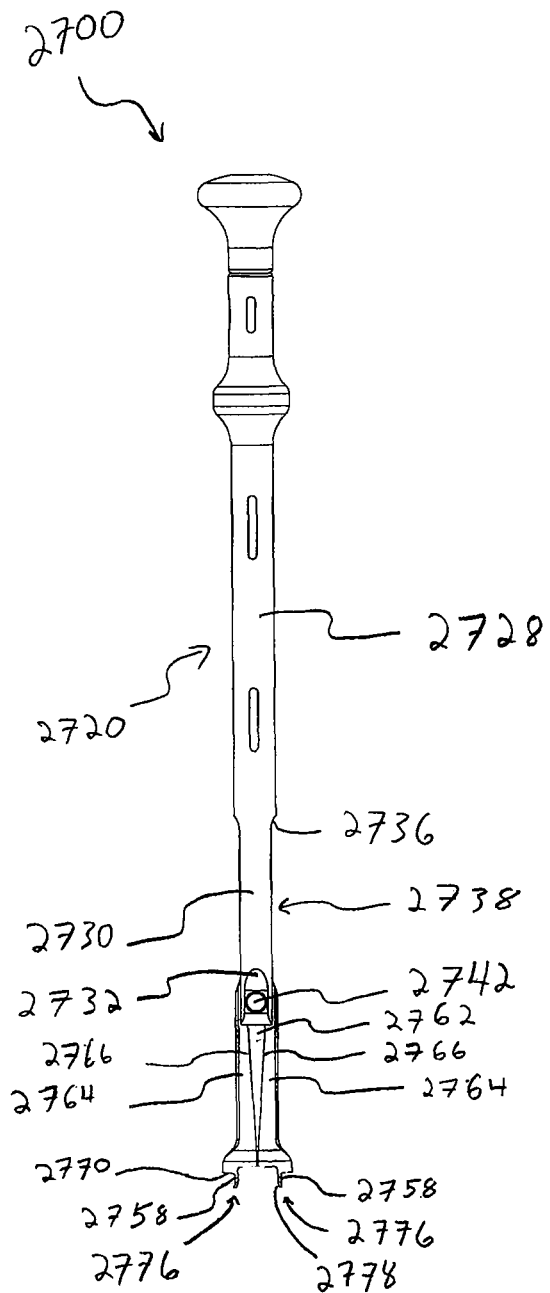
FIG. 114 is a front view of the plate holder of FIG. 113.
Figure 115:
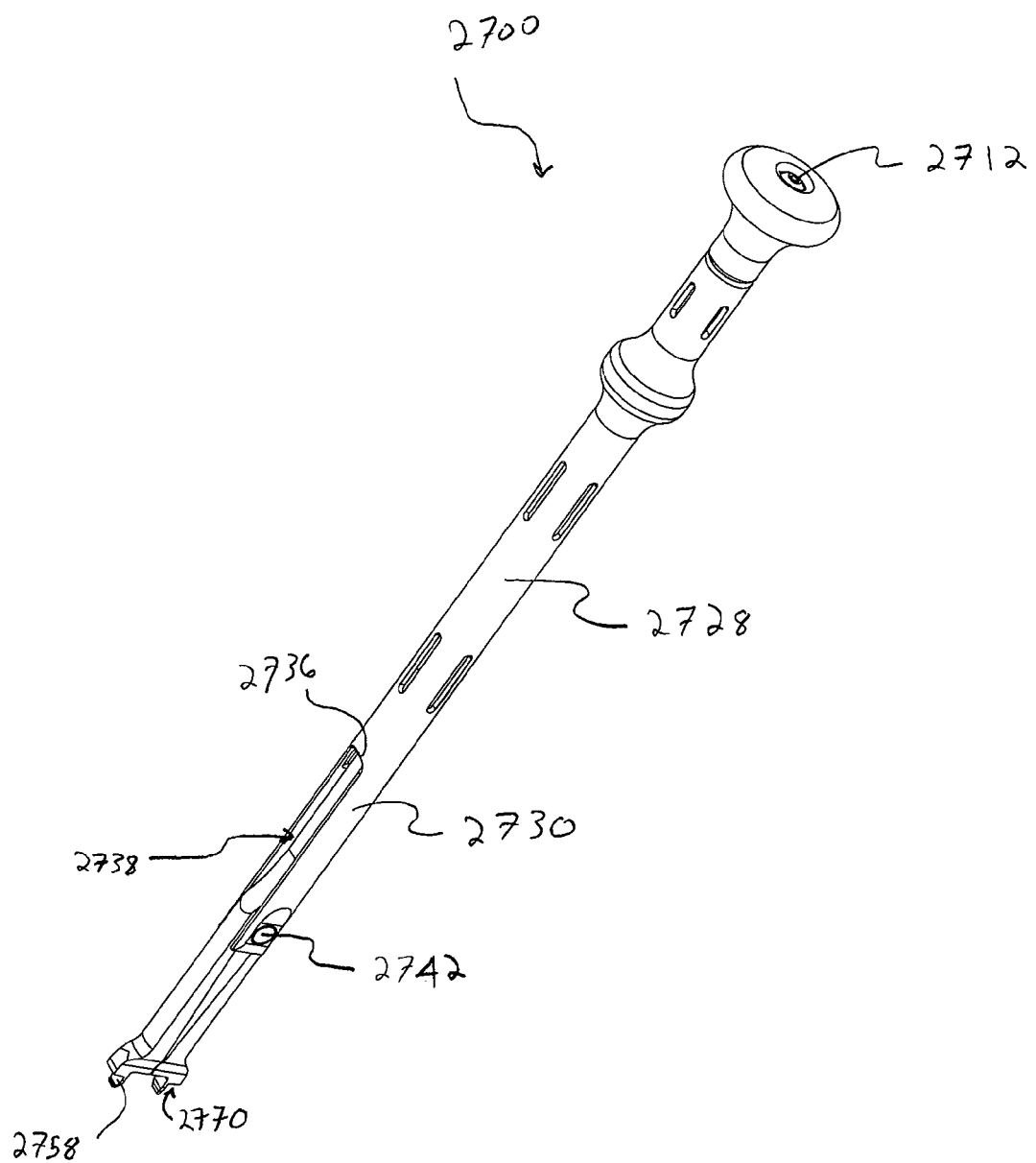
FIG. 115 is a perspective view of the plate holder of FIG. 113.

The plate holder 2700 comprises a handle 2710, an expansion sleeve 2720, and a clamping mechanism 2750. The handle 2710 is secured to the clamping mechanism 2750 by a cap screw 2712. The clamping mechanism 2750 is received within the elongated expansion sleeve 2720 and may translate longitudinally therein. In operation, the surgeon inserts legs 2776 of the unexpanded plate holder 2700 into openings 2792 on both sides of the pivot base 1300, as shown in FIG. 119. To shift the plate holder 2700 into an expanded configuration that engages the bone plate system, the surgeon grasps the handle 2710 in the palm of his hand and uses his fingers to push an enlarged grip 2726 of the expansion sleeve 2720 away from the handle 2710, which creates a spacing 2740 between the expansion sleeve 2720 and the handle 2710, as shown in FIG. 117. Turning to FIG. 114, the translation of the expansion sleeve 2720 along the clamping mechanism 2750 shifts the plate holder 2700 between the unexpanded and expanded configuration by ramping an expansion pin 2742 against inclined regions 2766 of clamping arms 2764, which forces the arms apart. The expansion of clamping arms 2764 causes the outer face 2758 of each leg 2776 to contact a relief area 1118 of the bone plate 1102, as shown in FIG. 118. The expansion force of the outer faces 2758 against the relief areas 1118 enables the plate holder 2700 to rigidly grasp the bone plate system 1100. Preferably, the surgeon must continue to apply a force to the expansion sleeve 2720 to overcome the resilient nature of the clamping arms 2764 and maintain the legs 2776 in their expanded state. Once the bone plate system is properly aligned along the vertebrae, the surgeon may use bone pins 2900 described above to temporarily fasten the bone plate system 1100 to the vertebrae. The surgeon would then remove the plate holder 2700 by shifting the expansion sleeve 2720 toward the handle 2710 and withdrawing the plate holder 2700 from the surgical area. Alternatively, a surgeon may decide not to use bone pins 2900 and would fasten the bone plate system 1100 to the vertebrae through openings 1310 in the pivot bases 1300 that are not obstructed by the plate holder 2700.

Figure 113:
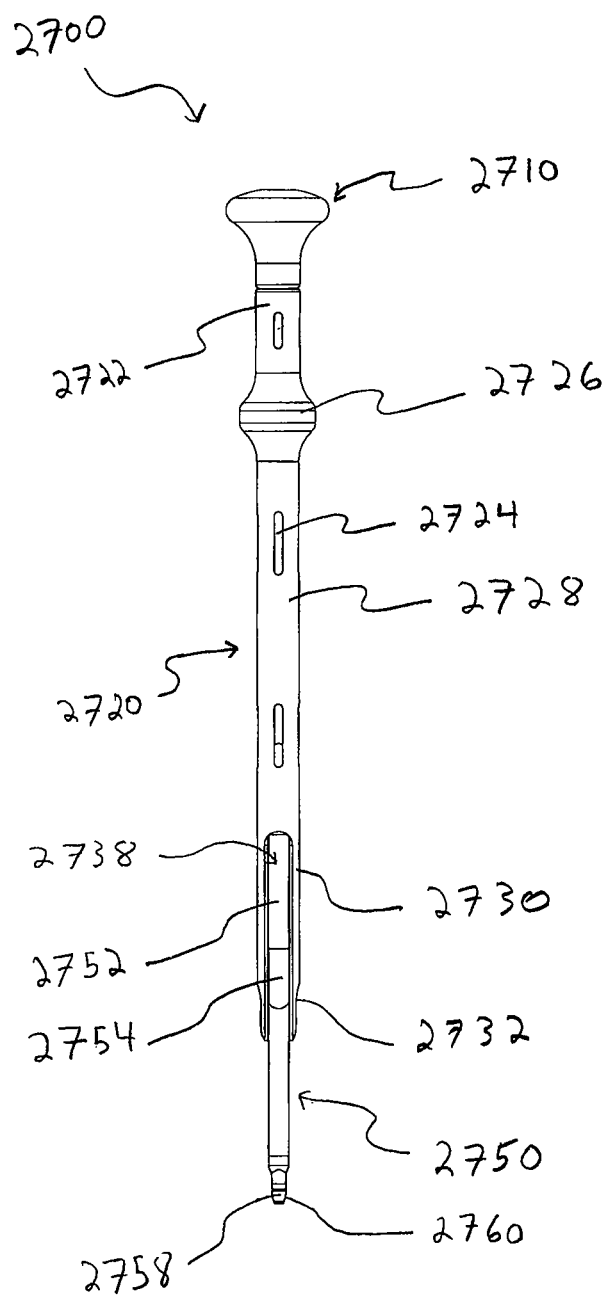
FIG. 113 is a side view of a plate holder including features in accordance with another aspect of the present invention.

The expansion sleeve 2720 comprises a proximal end 2722, an enlarged grip 2726, and a distal end 2728, as shown in FIGS. 113 and 114. The distal end 2728 includes fork members 2730 which define a gap 2738 and are joined by an arcuate cut-out 2736. The fork members 2730 each have a tapered portion 2732 adjacent the expansion pin 2742.

The clamping mechanism 2750 comprises a proximal end 2756 and a distal end 2768, as shown in FIG. 116. The distal end 2768 includes an upper tapered portion 2786, an intermediate flat portion 2752, a lower tapered portion 2754 and clamping arms 2764. The intermediate flat portion 2752 has a cavity 2788 and a spacing 2794 that define resilient arms 2790. The spacing 2794 extends from the cavity 2788 to a void 2762 which is defined between clamping arms 2764. The spacing 2794 and cavity 2788 are designed to allow the clamping arms 2764 to resiliently expand apart during operation of the plate holder 2700. Preferably, the cavity 2788, spacing 2794, and void 2762 are cut into the clamping mechanism 2750 during manufacturing by a wire electrical discharge machining process (EDM).

At the most distal end of the clamping arms 2764 are legs 2776 which are sized to fit in an opening 2792 formed between pivot base forked projections 1306 and the bone plate 1102, as shown in FIG. 119. In the case of an elongated bore, the openings 2792 are larger than in the case of a non-dynamized bore. Each leg 2776 includes a projection 2772 that holds the bone plate between the projection 2772 and a bottom surface 2770 of the respective clamping arm 2764 when the plate holder 2700 engages the bone plate system 1100. The projection 2772 has both a taper 2760 and a projection curvature 2778 that improve the ease with which the surgeon may insert the legs 2776 into the opening 2792.

Figure 120:
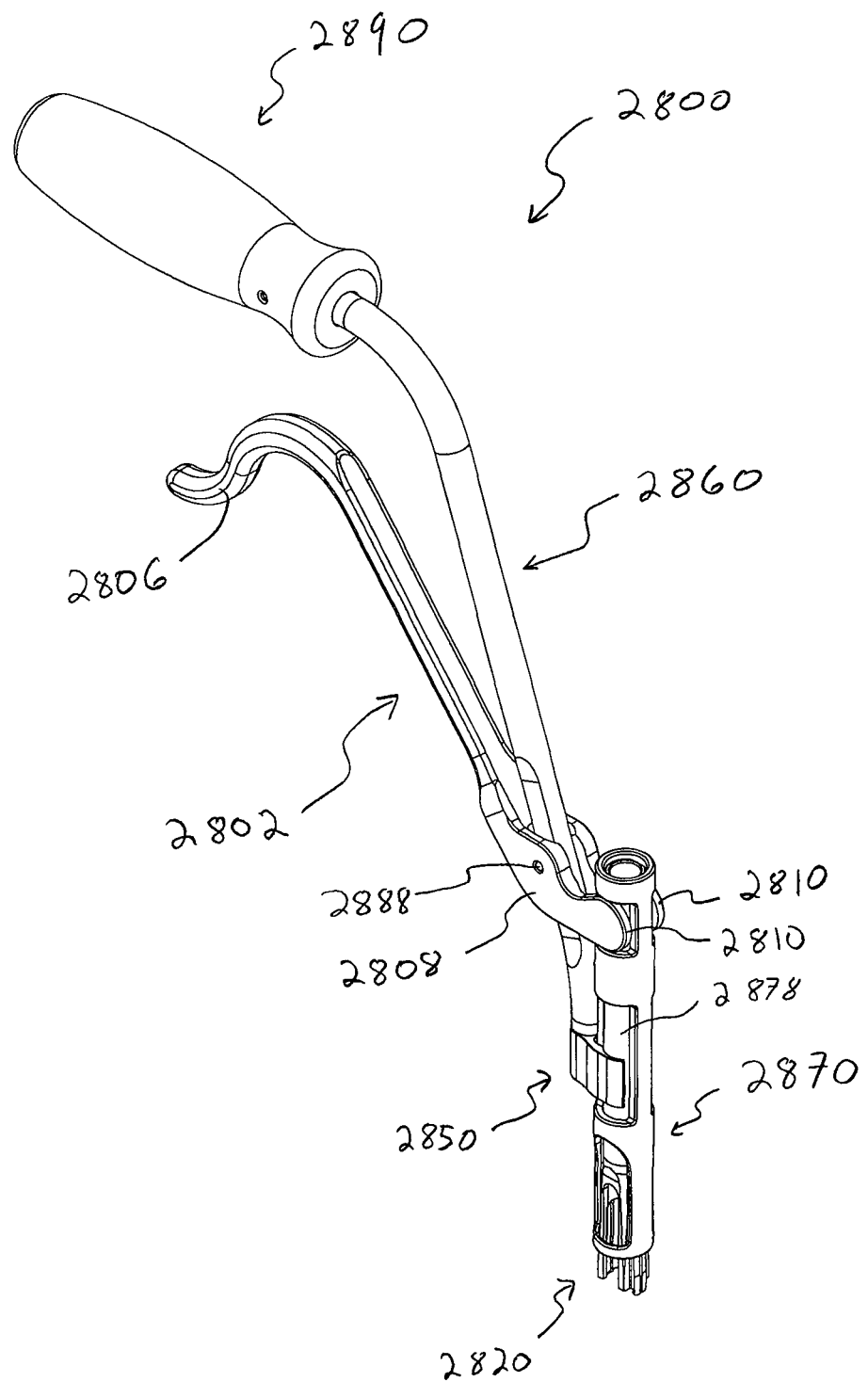
Figure 121:
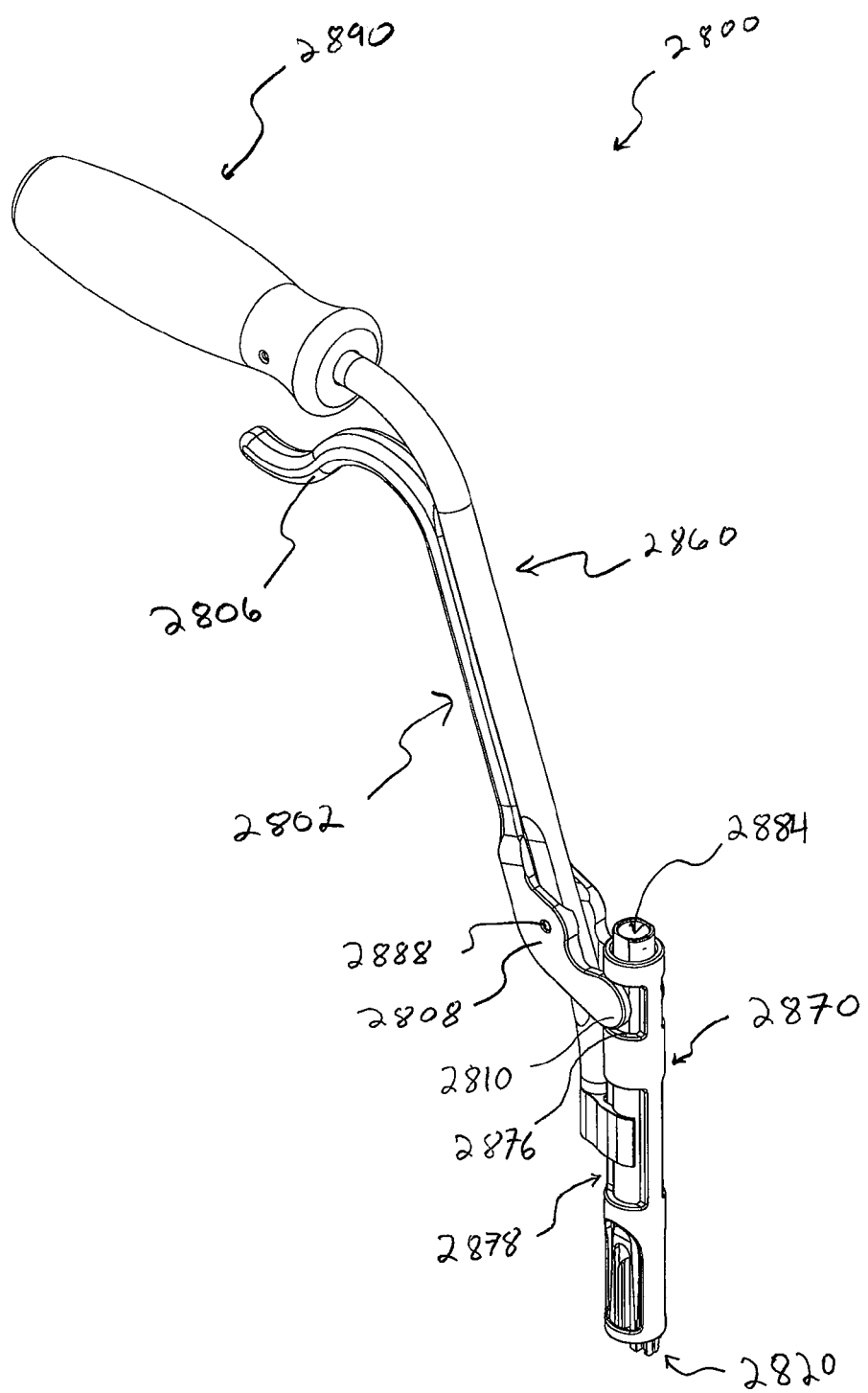
Figure 122:
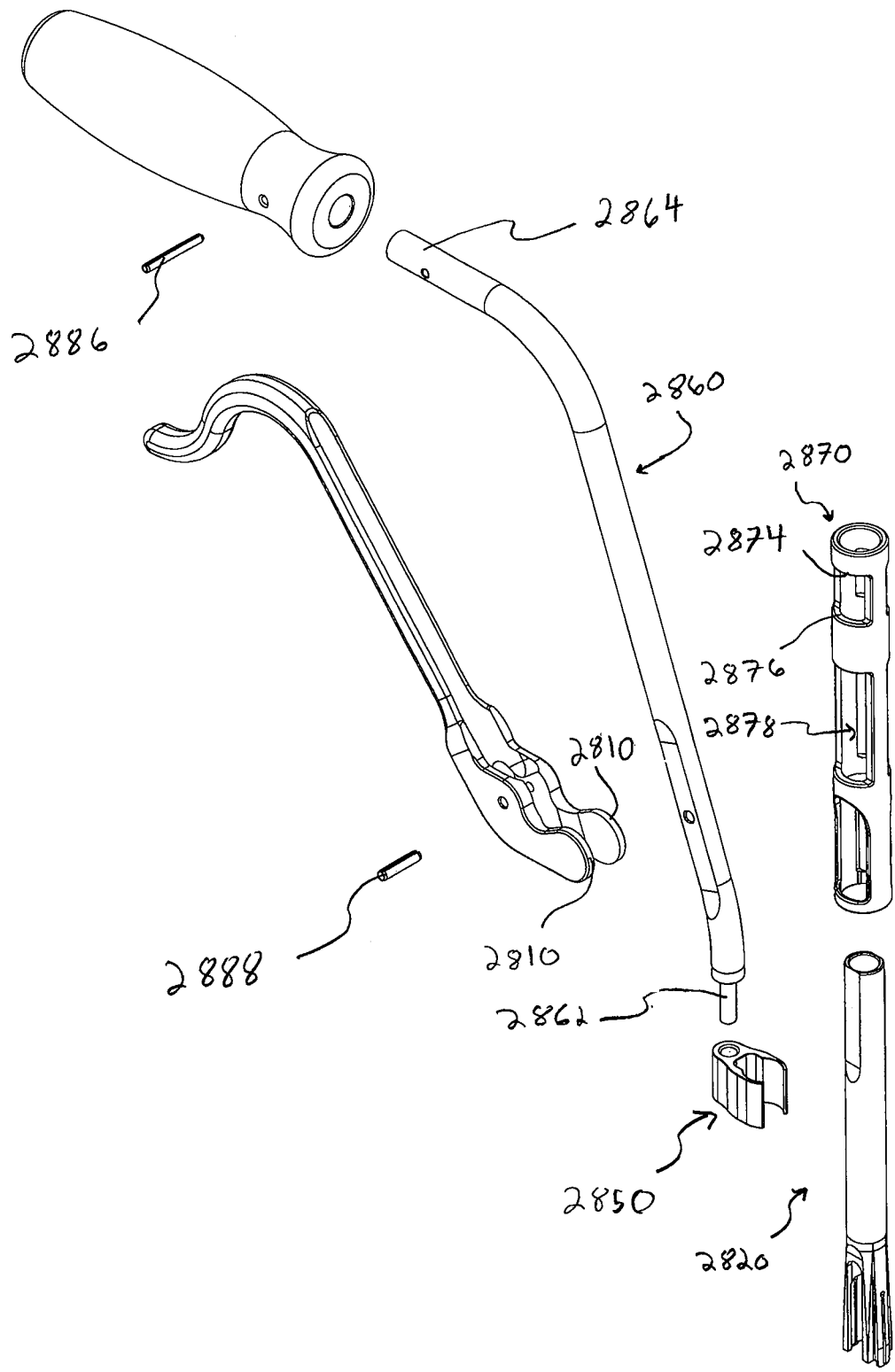
Figure 123:
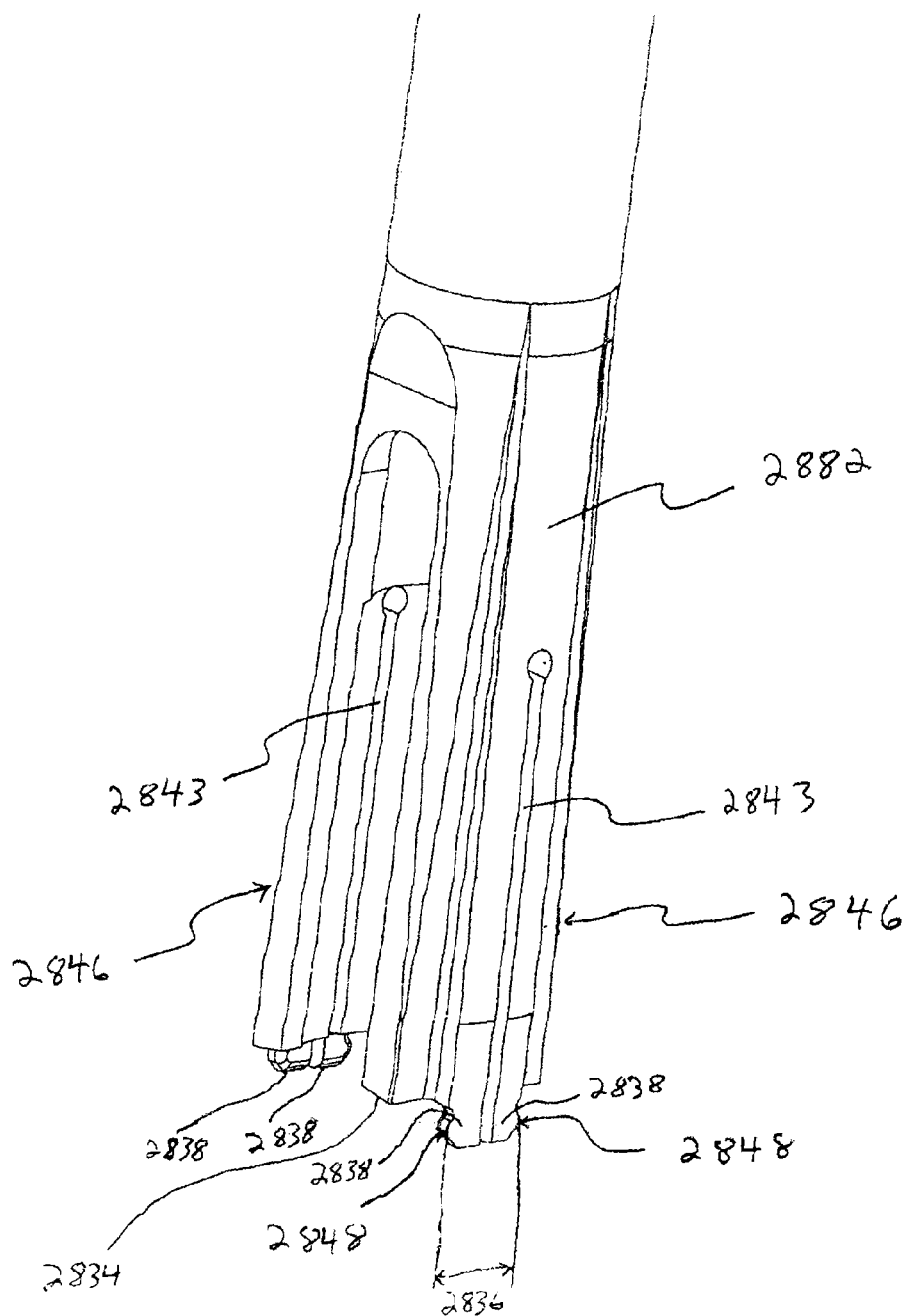
Figure 124:
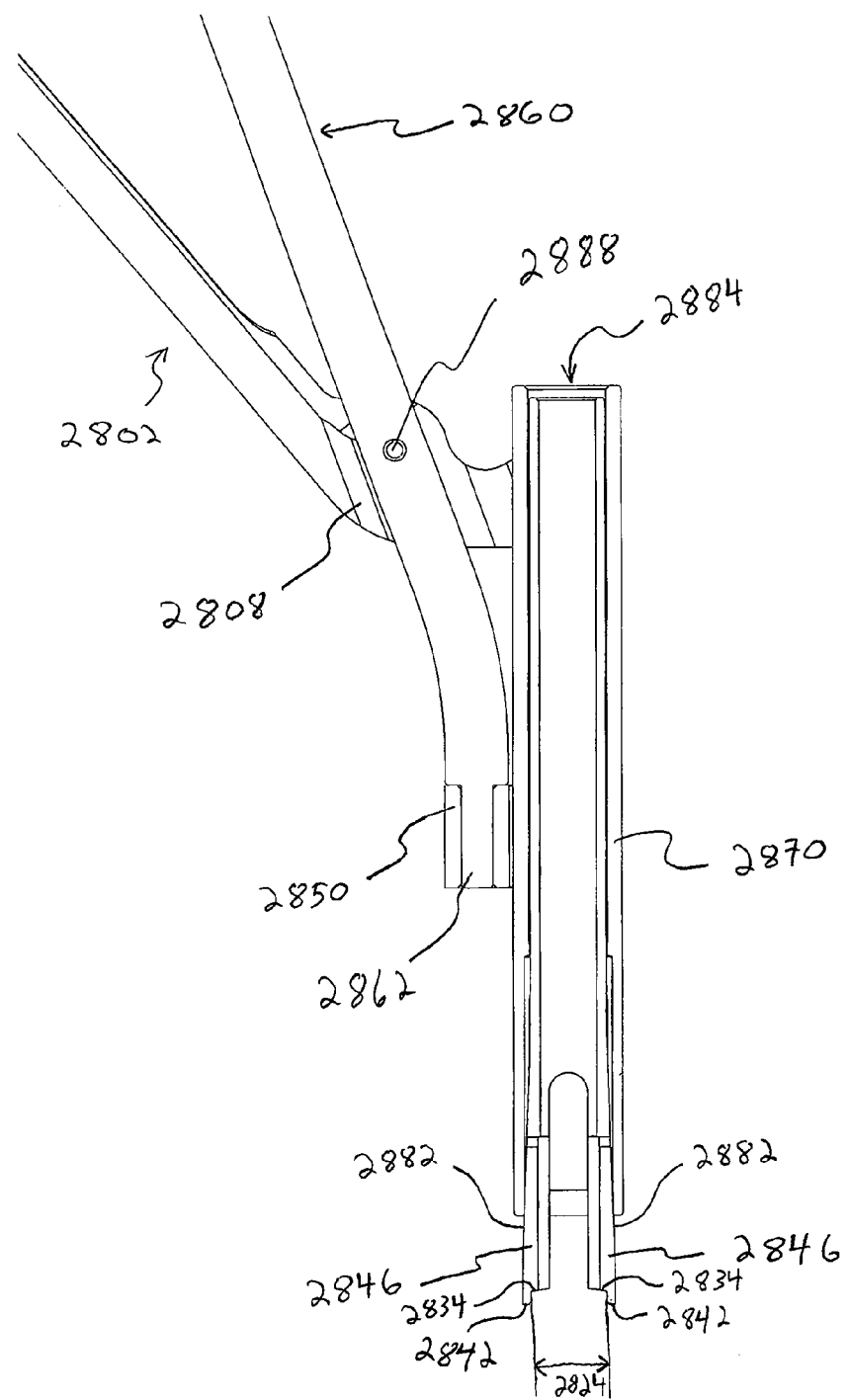
Figure 127:
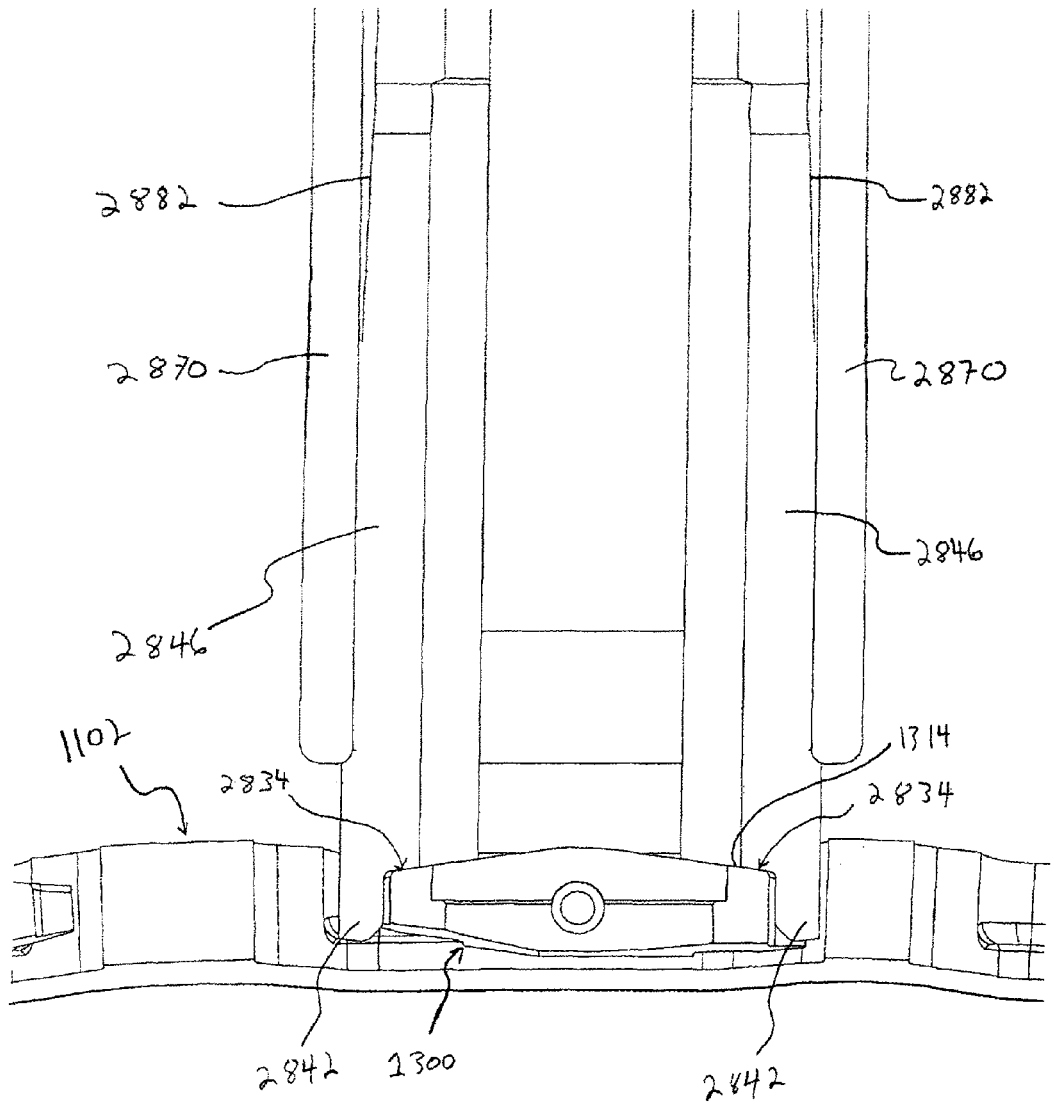
Figure 128:
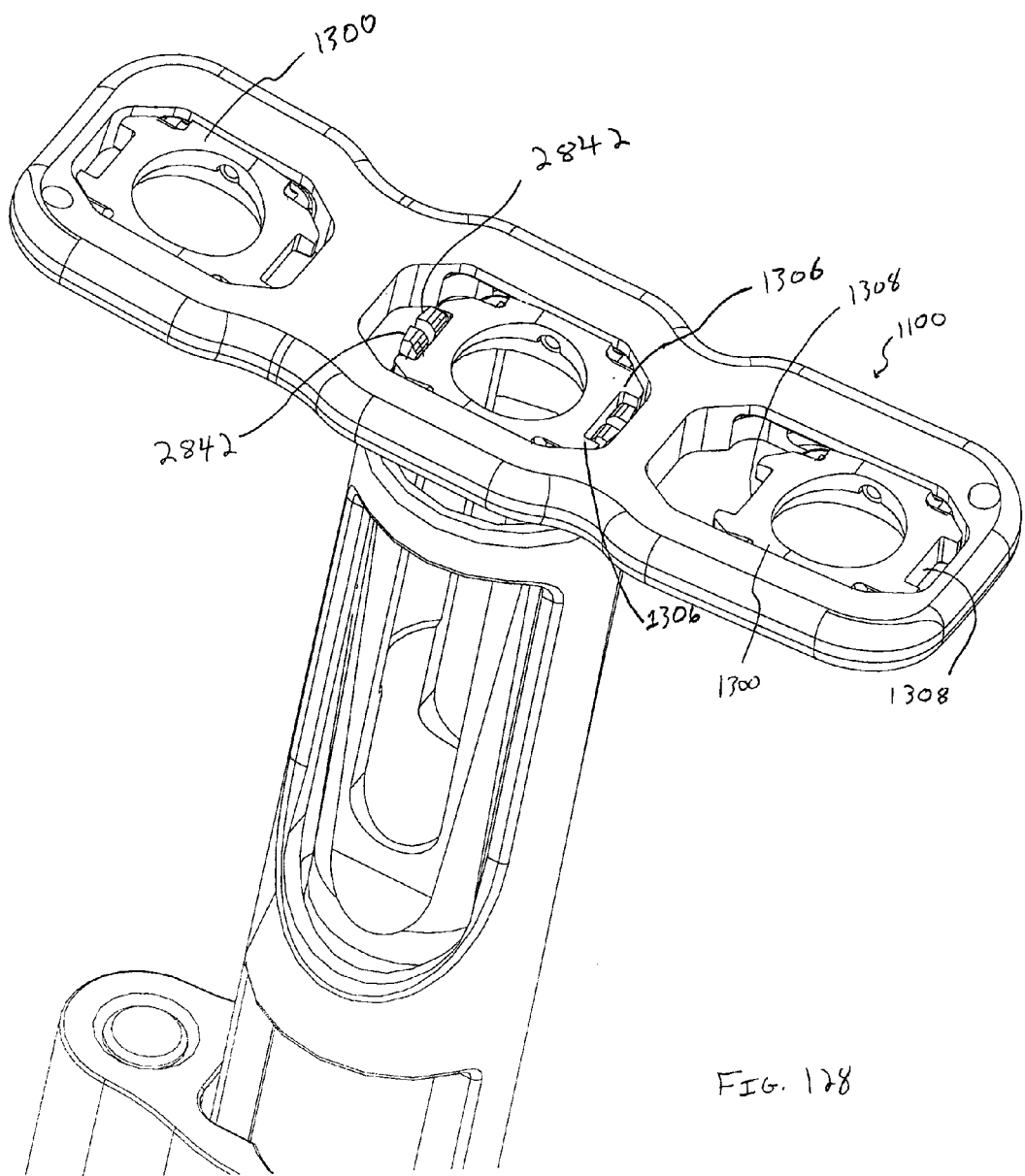

A surgeon may alternatively use a locking guide 2800, shown in FIGS. 120-128, to position bone plate systems 1100, 1200, 1700 that use pivot bases 1300. The locking guide 2800 may also be used with bone plate systems 100, 200 that use pivot bases 300, if the locking guide 2800 is configured to accommodate the upper surfaces of the pivot base 300 and the retaining member 500. The locking guide has an open configuration for positioning onto a bone plate system, as shown in FIGS. 120 and 124, and a locked position that engages a bone plate system, as shown in FIGS. 121, 127, and 128.

The locking guide 2800 is similar in many respects to the guide 2500 shown in FIGS. 96-107. Specifically, the locking guide 2800 allows the surgeon to maneuver a bone plate 1100 by engaging the pivot base 1300. Once the bone plate is in the desired position along the vertebra, the surgeon may insert a tool, such as the driver 2600, through a bore 2884 formed in the guide tube 2820 while the locking guide 2800 is still attached to the pivot base 1300.

The locking guide 2800 features a handle 2890, a connection arm 2860, a compression lever 2802, a guide tube 2820, and a compression sleeve 2870, as shown in FIG. 120. The surgeon operates the locking guide 2800 by grasping the handle 2890 and positioning the guide tube 2820 over the pivot base 1300 while the locking guide is in its unlocked configuration. The surgeon shifts the locking guide into a locked position about the pivot base by using his fingers to pull the finger grip portion 2806 of the compression lever 2802 toward the handle 2890, as shown in FIG. 121. When the finger grip portion 2806 is pulled toward the handle 2890, the compression lever 2802 pivots about a pin 2888 located in pivot portion 2808, which rotates rounded ends 2810 downward. The rounded ends, in turn, apply a force against a lower aperture surface 2876 formed in the compression sleeve 2870, which shifts the compression sleeve downward along the guide tube 2820. Turning to FIGS. 127 and 128, the guide tube 2820 has pivot base engagement arms 2846 with an outer taper 2882, so that translation of the compression sleeve 2870 downward along the pivot base engagement arms 2846 creates an inwardly directed force which collapses the pivot base engagement arms 2846 toward one another and engages the pivot base 1300. The surgeon disengages the locking guide 2800 from the pivot base 1300 by pushing the finger grip portion 2806 away from the handle 2890, which rotates rounded ends 2810 upward. The rounded ends apply a force against an upper aperture surface 2874 formed in compression sleeve 2870, which shifts the compression sleeve 2870 upward and allows the pivot base engagement arms 2846 to return to their undeflected state.

Figure 125:
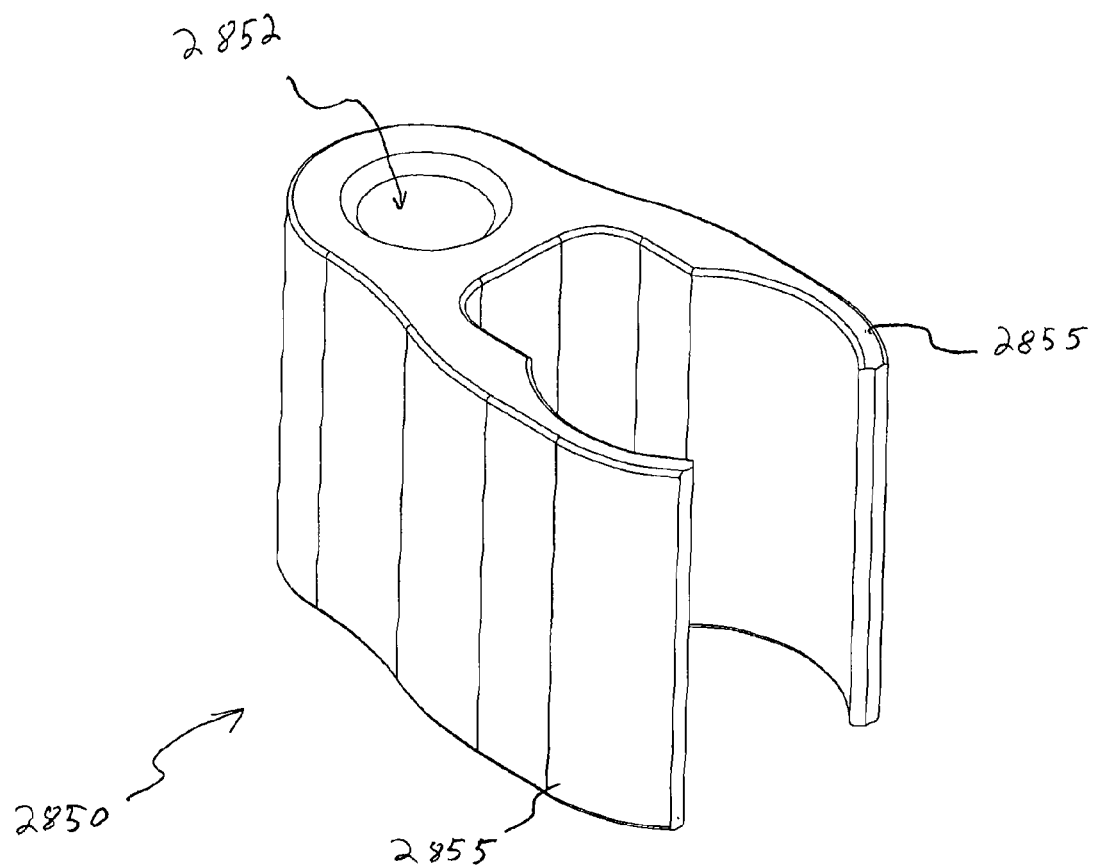
Figure 126:
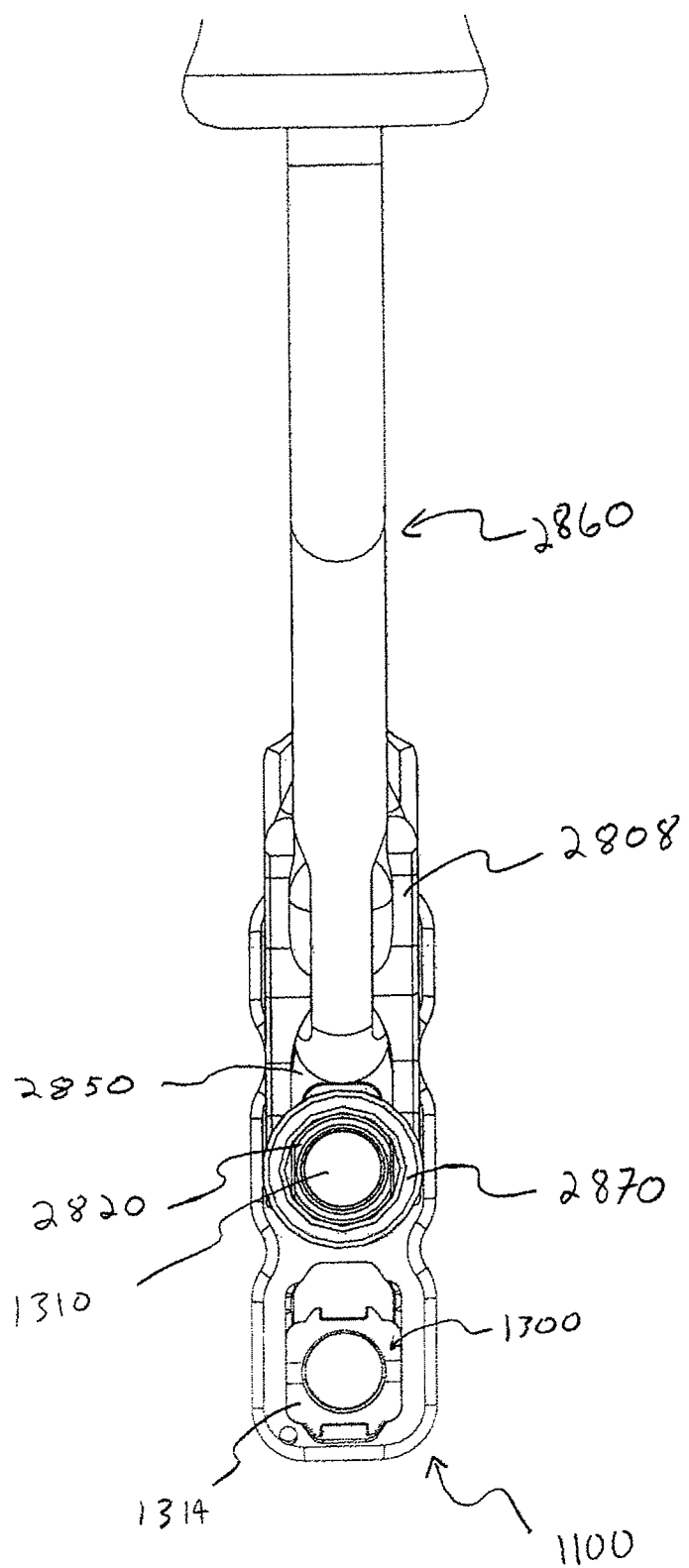

Furthermore, a handle extension base 2850 connects the guide tube 2820 and the connection arm 2860 in a manner similar to the coupling member 2550 shown in FIGS. 101 and 102. The handle extension base 2850 has a bore 2852 that receives a first end 2862 of the connection arm 2860, and curved arm portions 2855 that partially surround the guide tube 2820, as shown in FIGS. 122 and 125. During assembly of the locking guide 2800, the compression sleeve 2870 is first placed over the guide tube 2820 before the guide tube 2820 is seated in the curved arm portions 2855. The handle extension base 2850 is then permanently bonded to the guide tube 2820 using, for example, laser welding. Intermediate sleeve apertures 2878 allow the compression sleeve 2870 to translate along the guide tube 2820 without interfering with the curved arm portions 2855. The handle extension base 2850 is also permanently bonded to a first end 2862 of the connection arm 2860 after the first end 2862 has been placed within the bore 2852. A pin 2886 connects the second end 2864 of the connection arm 2860 to the handle 2890.

Turning now to FIGS. 124 and 128, when the locking guide 2800 is in the unlocked configuration, the pivot base engagement arms 2846 have opposing pivot base engagement teeth 2842 that are separated by a spacing 2824 that is wider than the distance between impressions 1308 in the pivot base 1300. This allows the engagement teeth 2842 to be inserted between the forked projections 1306 in the unlocked configuration, and to grasp the pivot base 1300 when the locking guide 2800 is shifted to the locked position. Each pivot base engagement tooth 2842 has two contoured portions 2838 that are separated by a gap 2843, as shown in FIG. 123. The pivot base engagement arms 2846 are made from a resilient material that permits the contoured portions 2838 to move relative to one another. Each contoured portion 2838 has a radius profile 2848 that contacts a forked projection 1306 in the pivot base 1300 when the surgeon engages the locking guide 2800 onto the pivot base 1300. In an undeflected position, each pivot base engagement tooth 2842 has a width 2836 that is wider than the distance between forked projections 1306 of the pivot base 1300. Thus, when a surgeon engages the locking guide 2800 onto the pivot base 1300 and deflects the contoured portions 2838 toward each other, the resilient nature of each pivot base engagement arm 2846 causes the contoured portions 2838 to exert a force against the respective forked projection 1306 to create an interference fit between the contoured portions 2838 and the pivot base 1300. The surgeon continues to insert the engagement teeth 2842 into the pivot base impression 1308 until a portion of the bottom surfaces 2834 of the pivot base engagement arms 2846 contacts a top face 1314 of the pivot base 1300, as shown in FIG. 127. The surgeon then pulls the finger grip portion 2806 toward the handle 2890 to shift the locking guide 2800 into the locked configuration which releasably engages the pivot base, as described above.

While the invention has been described with respect to specific examples, including presently preferred modes of carrying out the invention, those skilled in the art will appreciate that there are numerous variations and permutations of the above described systems and techniques that fall within the spirit and scope of the invention. Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A spinal bone plate system comprising:
   an elongate plate member;
   a plurality of throughbores of the plate member each extending along a respective bore axis through the plate member;
   a plurality of bone anchor members each having a non-threaded head end for driving the bone anchor members into spinal bones and a threaded shank depending from the head end with the non-threaded head end being radially enlarged relative to the threaded shank;
   at least one rigid pivot base for being received in one of the throughbores and having a rigid non-threaded wall and a through opening about which the non-threaded rigid wall extends and which is configured to receive one of the bone anchor members extending therethrough with the non-threaded radially enlarged head end of the one bone anchor member seated against the non-threaded rigid wall in the through opening in non-threaded engagement therewith so that the non-threaded rigid wall extends about the head end and between the head end and the plate member to completely space the head end from the plate member;
   a through aperture in the wall of the pivot base extending laterally therethrough and aligned with the head end of the bone anchor when the head end is seated within the through opening of the pivot base;
   at least one pivot member extending in the through aperture of the pivot base wall such that the seated bone anchor head end blocks laterally inward movement of the at least one pivot member, the at least one pivot member extending between the pivot base and the plate member to pivotally mount the pivot base to the plate member for pivoting relative thereto to allow pivoting of the rigid pivot base and the associated bone anchor member relative to the plate member with the head end of the bone anchor member seated in the pivot base opening and the bone anchor member driven into a spinal bone;
   floor portions of the elongate plate member that extend laterally transverse to the bore axis inwardly into the one throughbore on either side thereof to define a narrow section of the throughbore;
   lower surface portions of the rigid pivot base configured for being supported on the inwardly extending floor portions of the plate member upon pivoting of the rigid pivot base in the one throughbore; and
   an inner side wall portion of the plate member extending along the throughbore adjacent to the through aperture of the pivot base wall such that the inner side wall portion blocks laterally outward movement of the pivot member.

2. The spinal bone plate system of claim 1 including wherein the at least one pivot member a pair of pivot members on opposite sides of the pivot base.

3. The spinal bone plate system of claim 1 wherein the elongate plate member has an elongate axis, and the plate member has a channel extending along the axis in which at least a portion of the pivot member is received to allow both pivoting and translation of the pivot member portion in the channel.

4. The spinal bone plate system of claim 3 wherein the pivot base and channel have surfaces configured to allow pivoting of the pivot base within a predetermined angular range, and the one throughbore is elongated and has end surfaces that allow translation of the pivot base within a predetermined linear range.

5. The spinal bone plate system of claim 1 wherein the throughbore has a cavity in which the pivot member is received.

6. The spinal bone plate system of claim 1 wherein the head end of the bone anchor member is generally resilient, and;
   a locking member configured to cooperate with the resilient head end of the bone anchor to expand the head end of the bone anchor against the rigid pivot base for locking the head end in the pivot base through opening.

7. The spinal bone plate system of claim 6 wherein the pivot member is a pin.

8. The spinal bone plate system of claim 7 wherein the pin has a central longitudinal axis and an enlarged portion sized to be received with an interference fit in the aperture.

9. The spinal plate system of claim 8 wherein the pivot base pivots about the central longitudinal axis of the pin for pivoting of the pivot base relative to the plate member.

10. The spinal bone plate system of claim 1 wherein the bone anchor member and pivot base are substantially fixed relative to one another when the head end of the bone anchor member is seated within the through opening of the pivot base and the bone anchor member is driven into a spinal bone.

11. The spinal bone plate system of claim 1 wherein the elongate plate member has an elongate axis and all of the throughbores are aligned in a single row along the elongate axis.

12. The spinal bone plate system of claim 1 further comprising:
    a cavity of the inner side wall portion of the plate member;
    the through aperture of the pivot base wall being in substantial alignment with the cavity; and
    the pivot member includes a pivot pin received in the through aperture and the cavity.

13. A spinal bone plate system comprising:
    an elongate bone plate member extending along a longitudinal axis thereof, the bone plate member having upper and lower surfaces;
    a plurality of throughbores of the bone plate member extending between the upper and lower surfaces of the bone plate member and each having a pair of opposite longitudinal sides;
    a plurality of bone anchor members each having a head end for driving the bone anchor member into spinal bone;
    a rigid base member separate and distinct from the bone plate member for being received in one of the throughbores of the separate and distinct bone plate member;
    a rigid body of the rigid base member having an opening therethrough configured to receive one of the bone anchor members extending therethrough with the head end of the bone anchor member seated in the opening, the rigid body not deforming as the head end of the bone anchor member is seated in the rigid body opening;
    an upper wide portion of the base member that includes a pair of longitudinal side wall portions of the base member extending along the opposite longitudinal sides of the one throughbore which generally define a width of the base member therebetween transverse to the longitudinal axis of the bone plate member;
    a lower narrower portion of the base member that is disposed under the upper wide portion so that the upper wide portion has a pair of opposite side overhang portions including the longitudinal side wall portions that extend beyond corresponding sides of the lower narrower portion;
    a pair of floor portions of the bone plate member extending inwardly into the one throughbore and along the opposite longitudinal sides of the one throughbore below the upper surface of the bone plate member to define a narrow section of the one throughbore that is narrower than the width of the base member such that the floor portions support the base member received in the throughbore and allow for controlled relative motion between the base member and the bone plate member on the floor portions thereof after the bone anchor member is driven into a spinal bone and the head end is seated in the opening formed in the rigid body of the base member;

a top surface portion of the rigid body of the base member extending about the opening thereof and about the head end of the bone anchor member when the head end is seated in the opening of the rigid body;

lower surface portions of the side overhang portions of the base member disposed below the top surface portion that are configured to be supported by the inwardly extending floor portions of the bone plate member;

an upper enlarged portion of the one throughbore that opens to the upper surface of the bone plate member to form a wide section of the one throughbore across the longitudinal sides thereof that is wider than the rigid base member width to allow the rigid base member to be inserted downwardly into the throughbore upper enlarged portion with the side wall portions of the rigid base member in clearance with the opposite longitudinal sides of the throughbore in the wide section thereof;

a pin for extending between the base member and the plate member and pivotally connecting the base member to the plate member in the one throughbore;

a wall of the base member body extending about the opening;

a through aperture in the wall of the base member extending laterally therethrough and aligned with the head end of the one bone anchor member when the head portion is seated in the opening such that the seated bone anchor member head end blocks laterally inward movement of the pin; and an inner side wall portion of the bone plate member extending along the one throughbore adjacent to the through aperture of the base member such that the side wall portion blocks laterally outward movement of the pin.

14. The spinal bone plate system of claim 13 wherein the one throughbore is axially elongated and the controlled relative motion is a translational motion of the base member in the elongated throughbore.

15. The spinal bone plate system of claim 13 wherein the one throughbore is axially elongated, the base member includes substantially straight axially extending sides and the bone plate member includes axially extending guide surfaces extending along the one throughbore.

16. The spinal bone plate system of claim 13 wherein the base member comprises a pivot base and the bone plate member includes a cavity which receives a portion of the pin with the controlled relative motion being a pivoting motion between the rigid base member and the bone plate member.

17. The spinal bone plate system of claim 13 wherein the one throughbore is axially elongated and the controlled relative motion is both a translational and a pivoting motion.

18. The spinal bone plate system of claim 13 wherein the bone anchor member is substantially fixed relative to the base member with the head end of the bone anchor member seated in the opening of the rigid body of the base member.

19. The spinal bone plate system of claim 13 wherein the controlled relative motion is a pivotal motion of the base member in the throughbore.

20. The spinal bone plate system of claim 19 wherein the one throughbore is axially elongated.

21. A spinal bone plate system comprising:

an elongate bone plate member extending along an axis thereof;

a plurality of throughbores of the bone plate member, at least one of the throughbores being axially elongated;

a plurality of bone anchor members each having a non-threaded head end for driving the bone anchor member into spinal bone and a threaded shank depending from the head end with the head end being radially enlarged relative to the shank;

a pivot base for being received in the one axially elongated throughbore;

floor portions of the plate member extending inwardly into the one throughbore along opposite sides of the throughbore to define a narrow section of the throughbore, the floor portions being configured to support the pivot base in the throughbore;

lower surface portions of the pivot base configured for being supported on the floor portions of the plate member upon pivoting of the pivot base in the one throughbore;

an opening of the pivot base configured to receive one of the bone anchor members extending therethrough with the head end thereof being seated in the opening of the pivot base;

a non-threaded wall of the pivot base extending about the opening thereof which the non-threaded head end of the one bone anchor engages as the head end is seated in the opening of the pivot base, the non-threaded pivot base wall being configured so that the wall extends about the head end of the bone anchor member and between the head end and the bone plate member to completely space the head end from the bone plate member with the head end seated in the opening of the pivot base;

a through aperture in the wall of the pivot base extending laterally therethrough and aligned with the head end of the bone anchor member when the head end is seated in the opening of the pivot base;

a pin extending in the through aperture of the pivot base wall such that the seated bone anchor head end blocks laterally inward movement of the pin;

an inner side wall portion of the plate member extending along the throughbore adjacent to the through aperture of the pivot base wall such that the side wall portion blocks laterally outward movement of the pin; and cooperating surfaces of the one throughbore and the pivot base that allow for both translation and pivoting of the pivot base relative to the bone plate member with the bone anchor member driven into spinal bone and the head end of the bone anchor member seated in the pivot base opening.

22. The spinal bone plate system of claim 21 wherein the cooperating surfaces generally extend axially along the bone plate member axis to allow axial translation along the bone plate member axis and to allow pivoting about at least one pivot axis.

23. The spinal bone plate system of claim 22 wherein the at least one pivot axis comprises a pivot axis extending orthogonally to the bone plate member axis.

24. The spinal bone plate system of claim 22 wherein the pin extends between the cooperating surfaces of the one throughbore and the pivot base along the pivot axis.

25. The spinal bone plate system of claim 24 wherein the cooperating surfaces of the throughbore has a cavity for mounting the pin therein.

26. The spinal bone plate system of claim 25 wherein the cavity is an elongated groove, the elongated groove allowing pivoting of the pivot base about the pin in the groove, and the elongated groove allowing guided translation of the pivot base with the pin shifting in the groove.

27. A spinal bone plate system comprising:
an elongate bone plate member extending along an axis thereof;
a plurality of throughbores of the bone plate member with at least one of the throughbores having substantially straight, axially extending surfaces;
a plurality of bone anchor members each having a head end for driving the bone anchor member into spinal bone;
a rigid base member separate from the bone plate member for being received in one of the throughbores and having a rigid wall and a through opening about which the rigid wall extends and which is configured to receive one of the bone anchor members extending therethrough with the head end of the one bone anchor member seated against the rigid wall in the opening in the base member so that the rigid wall extends about the head end and between the head end and the bone plate member to completely space the head end from the bone plate member;
opposite, straight sides of the base member in confronting relation with the substantially straight, axially extending surfaces of the throughbore to keep the base member and the bone anchor member head end seated therein from turning in the one throughbore due to torque applied to the base member via the seated head end of the bone anchor member;
a through aperture in the wall of the base member extending laterally therethrough, the through aperture being aligned with the head end of the bone anchor when the head end is seated within the through opening of the base member;
a pivot member extending in the through aperture of the base member wall such that the seated bone anchor head end blocks laterally inward movement of the pivot member, the pivot member extending outwardly beyond one of the straight sides of the base member between the base member and the bone plate member to pivotally mount the base member to the plate member for pivoting relative thereto to allow pivoting of the base member and the one bone anchor member relative to the plate member with the head end of the one bone anchor member seated in the base member opening and the bone anchor member driven into a spinal bone;
floor portions of the bone plate member extending inwardly into the throughbore along the substantially straight, axially extending surfaces of the throughbore to define a narrow section of the throughbore;
lower surface portions of the base member for being supported on the inwardly extending floor portions of the plate member;
a portion of the pivot member being pivotally supported by one of the floor portions of the bone plate member for pivoting of the base member in the throughbore; and
an inner side wall portion of the plate member extending along the throughbore adjacent to the through aperture of the base member wall such that the side wall portion blocks laterally outward movement of the pivot member.

28. The spinal bone plate system of claim 27 wherein the base member has sides including the straight sides that form a generally polygonal configuration for the base member.

29. The spinal bone plate system of claim 27 wherein the base member has interconnecting, generally straight sides that extend between the opposite straight sides generally orthogonal to the bone plate axis with the base member received in the one throughbore so that the base member has a generally rectangular configuration.

30. The spinal bone plate system of claim 27 wherein the one throughbore is axially elongated and the surfaces thereof are guide surfaces that allow for translation of the base member in the elongate throughbore after the bone anchor member is driven into a spinal bone with the head end thereof seated in the base member opening.

31. The spinal bone plate system of claim 27 wherein the base member is pivotal in the throughbore of the bone plate member along a pivot axis extending orthogonal to the bone plate member axis.

32. The spinal bone plate system of claim 31 wherein the pivot member extends along the pivot axis between one of the straight sides of the base member and one of the axially extending surfaces of the throughbore.

33. The spinal bone plate system of claim 32 wherein the substantially straight, axially extending surface of the throughbore has a cavity formed therein, and the pivot member extends from the base member into the cavity of the throughbore.

34. The spinal bone plate system of claim 33 wherein the cavity of the throughbore is elongated and allows pivoting and guided translation of the pivot base and associated bone anchor member with the head end thereof seated within the opening of the base member relative to the bone plate member.

35. The spinal bone plate system of claim 27 wherein the elongate plate member has a narrow width and all of the throughbores are aligned along a single row along the elongate axis of the narrow width plate member.

36. A bone plate system comprising:
a plate member;
at least one throughbore disposed within the plate member;
at least one bone anchor having a head portion and a shank portion, the head portion configured for driving the bone anchor shank portion into bone;
a base member separate from the plate member configured to be disposed within the throughbore, the base member having upper and lower surfaces and a through opening extending between the upper and lower surfaces sized and configured to receive the bone anchor shank portion extending therethough and to receive the bone anchor head portion seated therein;
a pin extending between the base member and the plate member which pivotally connects the base member to the plate member in the throughbore thereof so that the base member is pivotal relative to the plate member with the head portion of the bone anchor seated within the through opening of the base member;
a wall of the base member extending about the through opening;
a through aperture in the wall of the base member disposed between the upper and lower surfaces of the base member extending outward from the through opening of the base member through the base member wall to an outer surface thereof so that the through aperture has end openings that open to both the base member through opening and the base member outer surface for receiving the pin extending between the base member and the plate member, the through aperture being aligned with the head portion of the bone anchor when the head portion is seated within the through opening such that the seated bone anchor head portion blocks inward movement of the pin;

floor portions of the plate member extending inwardly into the throughbore along opposite sides of the throughbore to define a narrow section of the throughbore;

lower surface portions of the base member configured for being supported on the inwardly extending floor portions of the plate member upon pivoting of the base member in the throughbore; and an inner side wall portion of the bone plate extending along the throughbore adjacent to the through aperture of the base member wall such that the side wall portion blocks outward movement of the pin.

37. The spinal bone plate system of claim 1 wherein the rigid pivot base includes a pair of straight sides and the elongate plate member includes a pair of guide surfaces extending along the plate member on opposite sides of the one throughbore in confronting relation with the straight sides of the rigid pivot base which restrict pivoting of the rigid pivot base to pivoting about an axis transverse to the length of the plate member.

38. The spinal bone plate system of claim 1 wherein the lower surface portions of the rigid pivot base are disposed on opposite sides of the through opening thereof and each lower surface portion includes a pair of surfaces inclined relative to one another to provide clearance for pivoting of the pivot base on the floor portions.

39. The spinal bone plate system of claim 13 wherein the lower narrower portion of the base member is sized and configured to fit within the narrow section of the one throughbore between the floor portions of the bone plate member.

40. The bone plate system of claim 36 wherein the wall of the base member includes a lip configured to support the bone anchor head portion seated in the base member through opening and the through aperture is arranged and configured to include at least a portion thereof that extends above the lip.

41. The bone plate system of claim 36 wherein the pin includes a portion sized to have an interference fit in the aperture.

42. The bone plate system of claim 1 wherein the pivot member includes a rounded portion supported on one of the floor portions, the rounded portion being configured to pivot on the floor portion with pivoting of the pivot base and the associated bone anchor member in the one throughbore.

43. The bone plate system of claim 42 wherein the pivot base lower surface portions includes a pair of flat surfaces disposed above one of the floor portions on opposite sides of the pivot member rounded portion, the pair of flat surfaces being inclined relative to one another and configured to contact the floor portion and limit pivoting of the pivot base.

* * * * *